(12) United States Patent
Luo et al.

(10) Patent No.: US 10,378,052 B2
(45) Date of Patent: Aug. 13, 2019

(54) METHOD OF WHOLE-GENOME SEQUENCING

(71) Applicant: HUAZHONG AGRICULTURAL UNIVERSITY, Wuhan (CN)

(72) Inventors: Meizhong Luo, Wuhan (CN); Yonglong Pan, Wuhan (CN)

(73) Assignee: HUAZHONG AGRICULTURAL UNIVERSITY, Wuhan (CN)

( * ) Notice: Subject to any disclaimer, the term of this patent is extended or adjusted under 35 U.S.C. 154(b) by 268 days.

(21) Appl. No.: 14/990,825

(22) Filed: Jan. 8, 2016

(65) Prior Publication Data
US 2016/0194704 A1    Jul. 7, 2016

Related U.S. Application Data

(63) Continuation-in-part of application No. PCT/CN2013/082782, filed on Sep. 2, 2013.

(30) Foreign Application Priority Data

Jul. 10, 2013 (CN) .......................... 2013 1 0288791

(51) Int. Cl.
G01N 33/48 (2006.01)
C12Q 1/6874 (2018.01)
C12Q 1/6806 (2018.01)
G16B 30/00 (2019.01)

(52) U.S. Cl.
CPC ......... *C12Q 1/6874* (2013.01); *C12Q 1/6806* (2013.01); *G16B 30/00* (2019.02)

(58) Field of Classification Search
None
See application file for complete search history.

*Primary Examiner* — Larry D Riggs, II
(74) *Attorney, Agent, or Firm* — Matthias Scholl P.C.; Matthias Scholl

(57) ABSTRACT

A whole-genome sequencing method, including: 1) extracting a whole-genome DNA and constructing a BAC library; 2) constructing mixing pools; 3) extracting DNA of the mixing pools; 4) performing pair-end sequencing for the DNA from the mixing pools; 5) scanning sequences of each mixing pool to obtain a feature sequence set and a k-mer set of each mixing pool; 6) analyzing a corresponding feature sequence set and a corresponding k-mer set of each clone; 7) constructing clone contigs; 8) dividing the k-mer sets of the clones into small k-mer sets and positioning the small k-mer sets; 9) assembling the NGS sequences to yield sequence contigs; 10) positioning the sequence contigs, connecting the sequence contigs and determining directions thereof; and 11) determining relative positions and directions of the clone contigs, and connecting the sequences of clone contigs as whole stripe of chromosome sequences.

2 Claims, 10 Drawing Sheets

METHOD OF WHOLE-GENOME SEQUENCING

CROSS-REFERENCE TO RELATED APPLICATIONS

This application is a continuation-in-part of International Patent Application No. PCT/CN2013/082782 with an international filing date of Sep. 2, 2013, designating the United States, now pending, and further claims priority benefits to Chinese Patent Application No. 201310288791.8 filed Jul. 10, 2013. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, and Cambridge, Mass. 02142.

BACKGROUND OF THE INVENTION

1. Field of the Invention

The invention relates to field of whole-genome sequencing, and more particularly to a whole-genome sequencing method based on DNA cloning mixing pool.

2. Description of the Related Art

Currently, there are two types of whole-genome sequencing strategies: clone-by-clone (CBC) and whole-genome shotgun sequencing (WGS).

The strategy of CBC includes constructing Genetic Map and Physical Map. The constructing of physical map is time-consuming, laborsome, and requires a lot of materials. It is the most complicated step in the whole sequencing process. Therefore, the application of such a whole-genome sequencing strategy is greatly restricted.

The WGS is simple and rapid and does not need preparing physical map, especially with the continuous development of next-generation sequencing technologies (NGS), the method is increasingly popular. However, WGS method has the following disadvantages: the read length of the sequence is too short, the calculation during sequence assembly is too complex and difficult, and the assembled sequence contains lots of gaps which are very difficult to fill up. In addition, it is hard to position the obtained scaffold on chromosomes and determine the relative positions thereof in the absence of reference sequences.

To fully utilize the advantages and avoid disadvantages, other methods are developed based on the two strategies. For example, the Short-tag Pooled Genomic Indexing, ST-PGI, and the End-sequence profiling, ESP.

A common precondition for using ST-PGI and ESP is that a high quality whole-genome of the same or similar species is provided as a reference sequence to position sequences and clones. However, the fact is that: not all species have respective high quality whole-genome sequence as reference.

SUMMARY OF THE INVENTION

In view of the above-described problems, it is one objective of the invention to provide a whole-genome sequencing method. Based on clone DNA mixing pool, the method can rapidly and accurately accomplish whole-genome sequencing while reducing cost effective. The method comprises the following steps:

1) extracting a whole-genome DNA and constructing a BAC library;
2) constructing BAC clone mixing pools;
3) extracting DNA of the BAC clone mixing pools;
4) performing pair-end sequencing for the DNA extracted from the BAC clone mixing pools in 3) by NGS sequences;
5) scanning sequences of each of the mixing pools to obtain a feature sequence set and a k-mer set of each mixing pool;
6) analyzing a corresponding feature sequence set and a corresponding k-mer set of each clone according to the feature sequence set and the k-mer set of the mixing pools;
7) constructing clone contigs according to the feature sequence sets of the clones;
8) dividing the k-mer sets of the clones into small k-mer sets by the clone contigs and positioning the small k-mer sets onto the clone contigs;
9) assembling the NGS sequences in the mixing pool of 3) to yield sequence contigs;
10) positioning the sequence contigs onto the clone contigs, using sequenced paired-end information to connect the sequence contigs and determining directions thereof, to obtain sequences of the clone contigs; and
11) determining relative positions and directions of the clone contigs by molecular markers, and connecting the sequences of clone contigs as whole stripe of chromosome sequences to obtain whole-genome sequences;

in which, algorithms for analyzing the feature sequence sets and the k-mer sets of the clones are as follows:

a total number of clones of a BAC library of a certain species is defined as a, and a total number of the constructed mixing pools is defined x, then:

the k-mer set of the mixing pool at a κ-th dimension having an index of λ is expressed as: $P_{(\kappa,\lambda)}$;

the k-mer sets of the mixing pools comprising a given clone are expressed as: $\{P_{(\delta)}|\delta<m, P_{(\delta)} \in P\}$;

an intersection set of k-mer sets of the mixing pools comprising the give clone, namely an initial k-mer set of the given clone, is expressed as: $C_\tau = \cap_{\delta=1}^{x} P_{(\delta)}$;

an excluded union k-mer set (EUKS) of the given clone in the mixing pools is expressed as: $CU_{(\kappa,\tau)} = \cup_{v=0}^{a} (v \neq \tau, 0 < v \leq a)$;

an intersection set of all excluded union k-mer sets (EUKS) of the given clone is expressed as: $CI_\tau = \cap_{\kappa=0}^{x} CU_{(\kappa,\tau)}$; and a final k-mer set (FKS) of the given clone is: $CF = C_\tau - CI_\tau$.

More specifically, the detailed algorithm for k-mer set analysis is as follows: since the feature sequence set is a sub-set of the k-mer set, the following algorithm is totally suitable for the feature sequence set.

I. Basic Operation of Sets

For two sets A and B, basic operations concerned in this method include:

A∩B: its result set is the elements in both Set A and Set B, namely intercross set of A and B.

A∪B: its result set is the elements either in Set A or Set B, namely union of A and B;

A−B: its result set is the elements in Set A but not in Set B, namely difference set of A and B;

$\cup_{i=m}^{n} A_i$: it refers to $A_m \cup A_{m+1} \cup A_{m+2} \ldots A_{n-2} \cup A_{n-1} \cup A_n$;

$\cap_{i=m}^{n} A_i$: it refers to $A_m \cap A_{m+1} \cap A_{m+2} \ldots A_{n-2} \cap A_{n-1} \cap A_n$.

The above defined sets exclude repetitive elements, namely every element in the set only appears once. However, it still needs to observe the times of element appearing during the computing process. The set that can record appearing times at the same is defined as Frequency Set or Key-value Set (KV-set). For frequency sets A and B, basic operations thereof are as follows:

1. A+B: it represents a union for elements in both the frequency set A and the frequency set B; if an element appears in both A and B, its frequency shall be a sum of its frequency in A and B.

2. A−B: it represents elements in the frequency set A, but not in the frequency set B. If an element appears in both A and B, its frequency shall be a difference obtained by minus frequency in B from A; if this difference is smaller or equals to 0, the element shall be eliminated from a result frequency set.

3. Key (A): it represents all elements in the frequency set A.

II. Analysis of the Feature Sequence Sets and K-Mer Sets of Clones

After the mixing pools are sequenced, scan the sequence of the mixing pools to get the feature sequence set (the definition refers to detailed embodiments of the invention "scan sequencing results and get the feature sequence sets of the mixing pools") and the k-mer set (the definition refers to detailed embodiments of the invention "scan sequencing results and get the k-mer set of the mixing pools") of each mixing pool, then calculate the feature sequence and the k-mer set of each clone. Among them, the calculation of the feature sequence and the k-mer set of the clone is the core part of the whole method.

Taking the calculation of the k-mer sets of the clone as an example, assume that put all the clones into a cube and construct mixing pools of clones, the dimension of the mixing pools is x (x>0); the number of mixing pools of each dimension is n (n>0), the total number of clones is a (a>0). The k-mer set of the mixing pool at the κ-th dimension with the index of λ is expressed as $P_{(\kappa,\lambda)}$ (κ<x, λ<n), a set after combination of the k-mer sets in all the mixing pools is a complete set of k-mer set of the genome sequence, which is expressed as $P=\cup_{\kappa=1,\lambda=1}^{\kappa=x,\lambda=n} P(\kappa,\lambda)$, namely a union set of the k-mer seta of all the mixing pools.

For the x mixing pools, the same number of clones are contained. Assume that the k-mer set of a given mixing pool is $\{P_{(\delta)}|\delta<m, P_{(\delta)} \in P\}$, the k-mer set of a clone jointly confirmed by a plurality of mixing pools is $C_\tau = \cap_{\delta=1}^{x} P_{(\delta)}$ which is called the initial k-mer set (IKS) of the given clone. $C_\tau$ (0<τ<a) means the IKS of the clone with the index τ.

For a given clone in a certain mixing pool, calculate the union set of the IKS of all other clones excluded from the given clone in the mixing pool $CU_{(\kappa,\tau)} = \cup_{v=0}^{a} C_v$ (v≠τ, 0<v<a). CU(κ,τ) means the excluded union set of the clone with the index of τ in the clone mixing pool at κ—the dimension with the index τ. The resulted union set is called as an excluded union k-mer set (EUKS) of the given clone. Then calculate an intersection of all the EUKS of the given clone $CI_\tau = \cap_{\kappa=0}^{x} CU_{(\kappa,\tau)}$, and finally calculate the final k-mer set (FKS) of the certain clone $CF = C_\tau - CI_\tau$.

According to the definition of the feature sequence and the k-mer, it is known that in case of the same length, the feature sequence set is a subset of the k-mer set. Thus, the calculation of a final feature sequence set (FFS) is the same as that of the final k-mer set. As shown in FIG. 8, 8 clones are obtained in the same cube, which is the simplest case of the clone number.

For the simplest case considered here, assume that there are eight clones A1-A8 (the clone and the real k-mer set of the clone are represented by the same symbol, for example, A1 represents the clone A1 as well as the real k-mer set of A1), and put them in one cube (FIG. 8). Then construct three-dimensional clone mixing pool (namely PX, PY, PZ in the mixing pool construction strategy), so as to get 6 mixing pools as P1 TO P6. According to the position of clones in the cube, the clones included in each mixing pool are as follows:

P1={A1,A2,A5,A6} P2={A1,A2,A3,A4} P3={A3,A4,A7,A8}

P4={A5,A6,A7,A8} P5={A1,A3,A5,A7} P6={A2,A4,A6,A8}

The mixing pool P1 contains clones A1, A2, A5 and A6, similar to the other mixing pools.

Assume that in order to obtain the final k-mer set of clone A1, the following steps are conducted:

1. Carry out high throughput sequencing for all the mixing pools, scan the sequencing results to get the k-mer sets B1-B6 corresponding to P1-PP6.

2. According to the information of the mixing pools containing a certain clone, calculate the intersection of the mixing pools. If clone A1 is in P1, P2 and P5, the intersected k-mer set of A1 is A1=B1∩B2∩B5. Intersected k-mer set of other clones are calculated in the same way and listed as follows:

A1=B1∩B2∩B5 A2=B1∩B2∩B6 A3=B2∩B3∩B5 A4=B2∩B3∩B6

A5=B1∩B4∩B5 A6=B1∩B4∩B6 A7=B3∩B4∩B5 A8=B3∩B4∩B6

3. Calculate the union set of the intersected k-mer set of all clones in addition to A1 in each mixing pool A1 locates to get the excluded union k-mer set of clone A1 in each mixing pool:

B1'=A2∪A5∪A6 B2'=A2∪A3∪A4 B5'=A3∪A5∪A7

4. Calculate the intersection of the excluded union k-mer set of the clone A1 obtained from the last step:

A1⁻=B1'∩B2'∩B5'

5. The intersected k-mer set of A1 obtained in step 2 minuses the intersection of the last step, to get the final k-mer set of clone A1:

A1~=A1-A1⁻

The above process can be represented by graphs. Assume that the k-mer of all the clones A1-A8 (FIG. 9) is represented by a circle and the overlapped part represents the co-owned k-mer. Since all the clones come from the same BAC library, they all contain the k-mer which is a vector to construct the library, namely as the part of the center circle. The more overlap between the circle and the circle, the more same k-mer the two clones have.

The following uses the mutual overlap of figures or excluded calculation to explain how to calculate the final k-mer set of clone A1. 6 mixing pools constructed by 8 clones are shown FIG. 10A, and clones contained in each mixing pool are obtained correspondingly. Then calculate the intersection of the k-mer set of every three mixing pools, such as A1 is the intersection result of the mixing pool P1, P2 and P5, and all the calculation results of the 8 clones are illustrated in FIG. 10B. The part with the deepest color is the intersection part of three mixing pools. For clone A1 existed in the mixing pool P1, P2 and P5, respectively calculate the union of k-mer set of all the other clones in addition to A1 in P1, P2 and P5, to obtain union sets P1', P2' and P5' excluded from A1, as shown FIG. 10C. Then calculate the intersection A1' of P1', P2 and P5', as shown in FIG. 10D. Finally the original k-mer set of A1 minuses A1' to get the final k-mer set A1⁻ of A1, as shown in FIG. 10E. The dark color part in the figure is the final k-mer set of A1.

Through figure calculation, it can be directly seen that the final k-mer set of A1 is not the complete real k-mer set (RKS) of A1, some k-mers are excluded from the real k-mer set, but the retained k-mers are the elements in the real k-mer set.

After the above calculation, A1⁻ is the final k-mer set of clone A1, and calculation of the final k-mer set of clones A2-A8 are conducted in the same way.

In the above example, when calculating the intersection of the k-mer set of the mixing pool to obtain the k-mer set A1 of clone A1, if the real k-mer set of clone A6, A4 and A7 contains common k-mers, the mixing pool P1, P2 and P5 also contain the common k-mers. When computing A1, the k-mer will also be assigned to A1. But in fact, the common k-mers of the three clones does not belong to clone A1, which introduces the false k-mers in A1. The false k-mers need to be removed, so step 3-5 are needed. If the real k-mer set of A1 and the real k-mer sets of A6, A4 and A7 have the common k-mers, the common k-mer also will appear in B1', B2' and B5', namely A1—obtained by intersecting the three sets will also contain the k-mers. After the calculation of step 5, the k-mers will be removed from A1, that is, the real k-mers are removed from A1. Therefore from step 3-5, when removing the false k-mers, some real k-mers are also removed. Though the final k-mer set of clone obtained through the above calculation will lose some k-mers compared to the real k-mer set of clone, the elements in the final k-mer set all belong to the real k-mer set, that is, it does not contain the false elements.

The premise of the above derivation is in the ideal case that the sequence of all the clones in each pool can be detected, the k-mers of each clone can also be detected, and there is no sequence error. But in fact, due to the influence of the experimental conditions, sequencing errors and the randomness of sequencing, the ideal situation is impossible to achieve. So, A1 cannot contain all the real k-mers belonging to C1. Similarly, the k-mer set of other clones cannot contain all of their real k-mers. Therefore it will lead to that BP will lose some k-mers belonging to the mixing pool P1, and B2' and B5' in the same way will lose some k-mers belonging to P2 and P5 respectively. When compute the intersection of B1', B2' and B5' to get A1⁻¹, A1⁻ will lose some k-mers. When the missing k-mers belong to A1, but do not belong to the real k-mer of P1, these errors will be retained in the final k-mer set A1⁻ of P1, that is, the false positive is introduced in A1~. For the introduced false k-mer set due to sequencing errors, before analyze the k-mer set of clones, it is required to use the frequency of k-mer appeared in the k-mer set of the mixing pool to filter. That is, if the occurrence of a certain k-mer in the set is less than a certain value, it is considered that the k-mer is introduced due to sequencing errors, so as to remove most of the false k-mers in the k-mer set of the mixing pool. Filter frequency is related to sequencing depth and sequencing errors. The greater sequencing depth is, the more sequencing errors are, and the greater filter frequency is. If the sequencing error is less than 3%, the sequencing depth is 20 times, and the filter frequency selects 1, which can filter most of the false k-mer.

Taking into account the introduction of false positive of the final k-mer set of clones, it is needed to increase the sequencing depth in order to detect the real k-mer contained in each hybrid pool as much as possible. As far as possible exclude the false positive in the final k-mer set. When calculate the excluded union set of specific clones, balance the union set, which is called as balancing the k-mer set of mixing pools.

III. Balance the Feature Sequence Set and K-Mer Set of the Mixing Pool

Suppose that there are n clones in a mixing pool. Put the elements in the intersected set of all the clone k-mers in the mixing pool in one KV-set, the frequency of all the elements is 1. When calculate the union set of the intersected set of clone k-mers (step 3 in the above example), calculate the sum of the KV-set of all clones in the mixing pool to get the KV-set of the mixing pool. Then compare the key in KV-set of mixing pool and the elements in the original k-mer set of mixing pool, add the elements included in the original k-mer set but not in KV-set into KV-set, set the frequency of the newly added key as 2. The KV-set obtained in this way is called a sum KV-set of the mixing pool.

If one clone is in this mixing pool, construct a KV-set C according to the intersected set of the clone k-mers. The elements in C are the elements in the intersected set of clone k-mers. Set the frequency of all the elements as 1. Assume that the sum KV-set of the mixing pool is P, P minuses C, namely P'=P−C, then take the key set Key (P') from P' as the union set of the mixing pool to exclude the given clone. For the above example, that is B1', B2' and B5' of the k-mer set of B1, B2 and B5 after excluding A1.

On the integration of sequence positioning and physical map, more detailed algorithm is as follows:

1) Segmentation of the Clone Contigs

The k-mer sets of the clones are segmented into blocks according to relative positions of the clones in the clone contigs. Assuming that two clones belongs to a same contig and overlap with each other, set A represents the k-mer set of one clone, and set B represents the k-mer set of the other clone, then the two k-mer sets are divided into three sub sets, that is, a common k-mer set (A∩B), a specific k-mer set of A (A−B), and a specific k-mer of B(B−A). The relative position of the three k-mer sets are determined according that the common k-mer set is located between the two specific k-mer sets. According to this algorithm, it is possible to segment all the clone k-mer sets in each clone contig from the end into smaller sub sets according to their relative position, and the relative position of these sub sets is determined (As shown in FIG. 7).

2) Sequence Positioning and Integration

NGS sequences of the mixing pools are respectively assembled by a short sequence assembly software (such as velvet), assembly results are then merged and further assembled by a long sequence assembly software (such as PCAP) to get sequence contigs. Each sequence contig is divided into k-mer sets, intersection between the k-mer sets divided from the sequence contigs and the k-mer sets of all the blocks are computed, and blocks with a maximum number of intersection elements are obtained thereby locating the sequence contigs onto the blocks of the clone overlapping area (9 sequences from seq_1 to seq_9 shown in FIG. 7 are distributed to the relevant small blocks). In case the sequence located onto the same clone contig comprises multiple of overlapped regions, the overlapped sequences are required to be assembled and merged again, and a resulting sequence is then re-positioned.

Use double end comparison software (such as Bowtie2) to carry out double end comparison for NGS sequences of all the mixing pools and the positioned sequences (shown in FIG. 7, four pairs of double end from PE1 to PE4 are highly matched to the relative sequence). If the two sequences and the double end of a certain sequence are highly matched (such as identity value≥97%), the two sequences are positioned in the same clone contig and the positioned contig block is in a certain range, then it is considered that the two sequences can be connected together. According to the sequencing library fragment length and the comparison results of double end, calculate the gap length between them, and use "N" to fill the gap. Meanwhile according to the relative position of the block of two sequences, determine the direction of the sequence after connection (in FIG. 7, seq_4 and seq_5 can be connected by two ends of PE2, expressed as seq_4-seq_5. Seq_4 and seq_5 are positioned in block bin_4 bin_5 respectively, so the direction of the sequence seq_4-seq_5 after connection can be determined). If a connection and other sequences cannot be connected by double end sequence, then compare the decomposed k-mer set and the k-mer set of the adjacent block. If it has a certain intersection with the k-mer set of the adjacent block, it can position the junction of the two blocks so as to determine its direction (in FIG. 7, seq_3 is positioned in the small block bin_3, also has larger intersection with bin_4, so it can determine the direction of seq_3 according to its intersection with the k-mer set of the two small block). Finally, according to the relative position of these sequences in blocks, connect all the positioned sequences after the double end connection into the sequence of the whole clone contig. If several sequences after double end connection are positioned in the same block, the relative position and direction between them can be randomly selected (in FIG. 7, three sequences seq_6-seq_7-seq_9 connected by PE3, PE4 and seq_8 are all positioned in bin_6, so the sequence and direction between them are not determined. Randomly select their direction and position when connect).

Advantages of the whole-genome sequencing method according to embodiments of the invention are given below:

1) The method does not need to carry out the enzyme digestion and electrophoresis for each clone, and is able to construct the physical map according to the feature sequence. The number of available feature sequences can be selected according to the needs, and the number is large, no error in the length reading of the electrophoresis bands exists.

2) The method employs NGS high throughput sequencing technology and clone mixing pool to construct the physical map of the whole-genome as well as position the assembled sequences to the physical map. In addition, all the data come from the same sequencing data set.

3) The construction of physical map and sequence assembly can be carried out simultaneously. The large genome can be divided into many small projects which are then processed simultaneously, thus improving the efficiency.

4) The complete sequence of the genome has little error in the large framework due to the presence of physical maps. For the error in the small area, the clear position can be located during the sequence assembly process which is beneficial to the gap filling and error correction of the complete sequence of genome in the future.

5) The method has more general applicability and is applicable for the shotgun sequencing (WGS) of the complete genome, the second generation sequencing technology (NGS), or the third generation sequencing technology. In addition, these sequencing methods can be integrated to make full use of their advantages in order to improve the accuracy and integrity of the sequence.

6) The method has high flexibility, because the feature sequence is an absolute value. The feature sequences can be easily added and integrated to further improve the genome sequence.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a whole-genome sequencing method are described below. It should be noted that the following examples are intended to describe and not to limit the invention.

Complete genome sequencing is carried out on *Arabidopsis thaliana* ecotype Columbia. The species has a total of 5 chromosomes, the complete genome sequence of about 122 Mb. It should be noted that the data reproduced in this example is only used for the description of the implementation process of the invention.

Construct BAC Library

Use restriction endonuclease BamHI to carry out partial digestion too the complete genome DNA, construct the BAC library with about 5 times of complete genome coverage. The library is preserved in 11 blocks with each block containing 384 wells, a total of 4224 BAC clones are obtained. The average insert fragment size of BAC clones is 137 kb with fragment length of between 60 and 300 kb.

Number the BAC Clones from 0 to 4223.

Construct the Clone Mixing Pool

Figure 1:
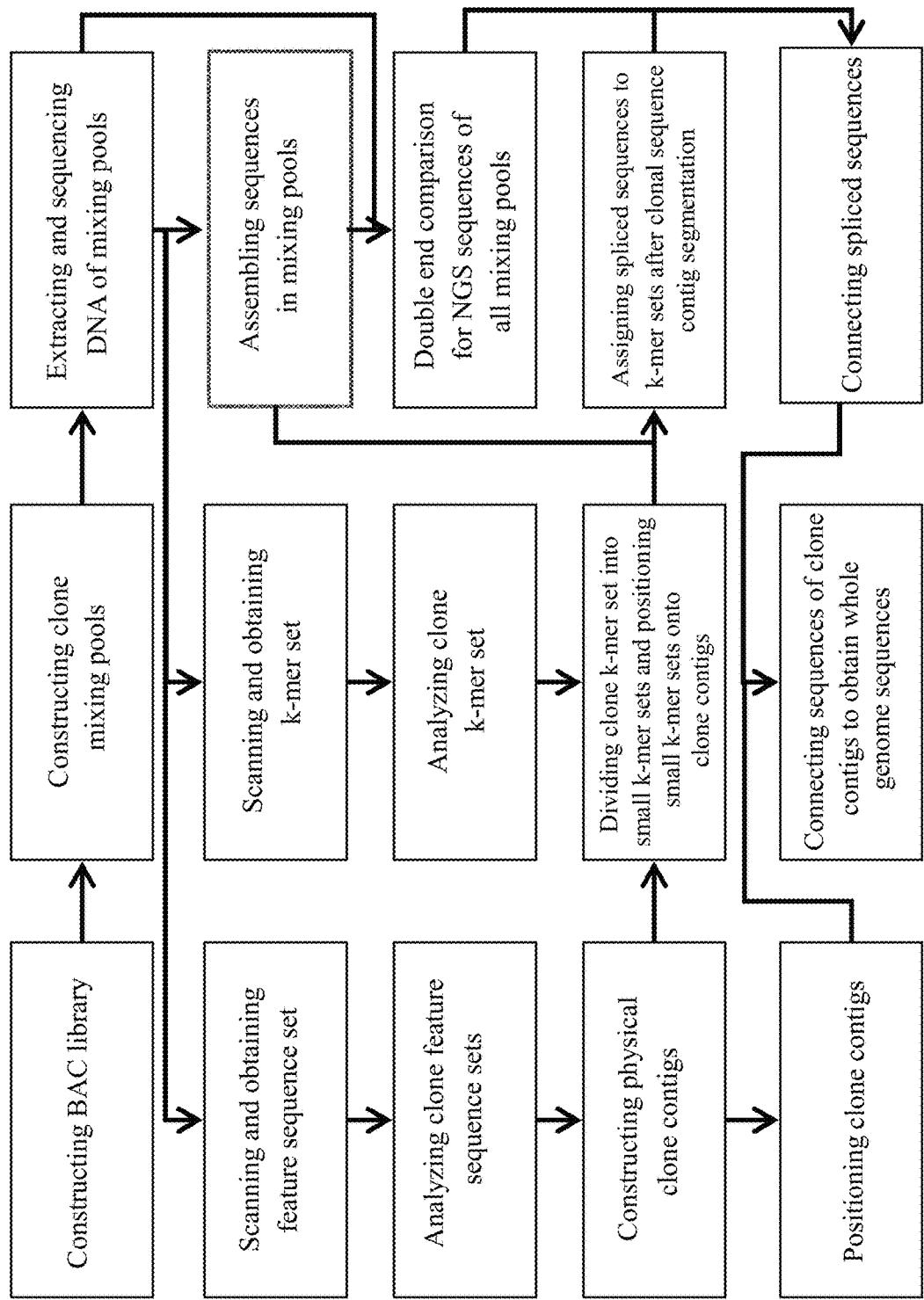
FIG. 1 is a flow chart of a whole-genome sequencing method in accordance with one embodiment of the invention.
Figure 2:
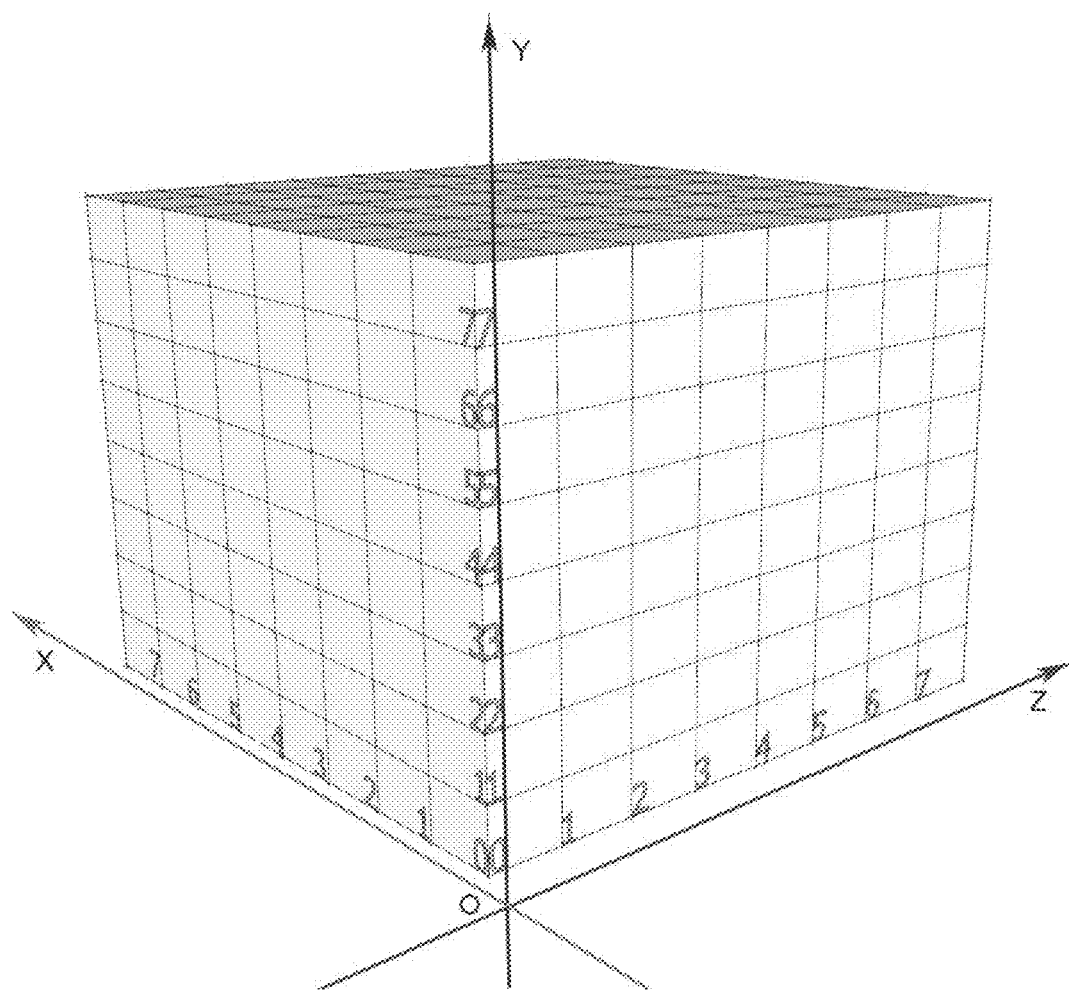
FIG. 2 is a rectangular coordinate system for mixing pool construction; each clone in the cube can be determined by three coordinate values (x, y, z)

N clones are selected from the BAC library, and the clones are arranged in an n×n×n cube. Then place this cube (FIG. 2) in the right-hand rectangular coordinate system, X, Y, Z are the coordinate axes, O is the origin. The position of each clone can be determined by three coordinate values (x, y, and z), and the position of the clone in the cube is represented by (x, y, z). Construct the clone mixing pool on the basis of cube constructed by BAC clone. The clone set in the same mixing pool can be represented by $\{(x1, y1, z1), (x2, y2, z2), (x3, y3, z3), \ldots, (xn, yn, zn)\}$.

Figure 3:
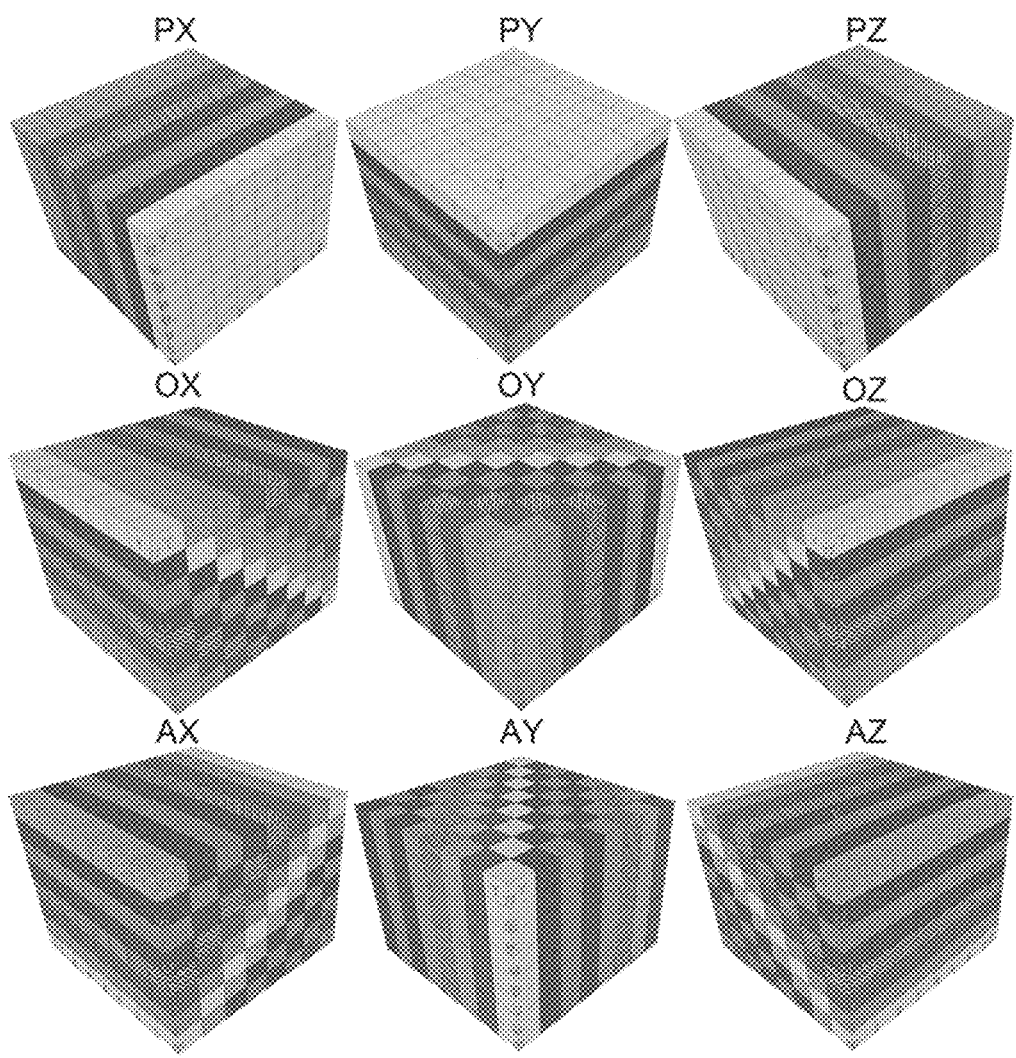
FIG. 3 is a construction strategy diagram of the fixed sequence mixing pool; in each cube in the figure, the clones with the same color or material mark belong to the same mixing pool.

When the position of all the clones in a cube is determined, no change is required. When construct a multidimensional mixing pool, just reassemble a new mixing pool (FIG. 3) through the clones from different dimensions. Taking into account the simplicity of the actual operation, the clones of the same column or the same row on each dimension belong to the same mixing pool. According to this principle, for a determined cube, there are 9 kinds of strategies of mixing pool construction, and the mixing pool constructed by each strategy is called 1 dimension. The 9 strategies are divided into three categories, respectively as perpendicular crossing pools (including PX, PY and PZ), oblique crossings pools (including OX, OY and OZ) and angle crossings pools (including AX, AY and AZ). In FIG. 3, a face and the cube intersect, the clones with same color or material mark belong to the same mixing pool.

In the PX, a face perpendicular to the X axis intersects with the cube, the clones on the same face belong to the same mixing pool, namely the clones with the same x value in all the clone position are in the same mixing pool, for instance, when x value is 0, the clones include:

$\{(0,0,0),(0,1,0),(0,2,0) \ldots (0,n-1,0),$ $(0,0,1),(0,1,1),(0,2,1) \ldots (0,n-1,1),$ $(0,0,2),(0,1,2),(0,2,2) \ldots (0,n-1,2),$ $(0,0,3),(0,1,3),(0,2,3) \ldots (0,n-1,3),$ $\ldots$ $(0,0,n-1),(0,1,n-1),(0,2,n-1) \ldots (0,n-1,n-1)\}$ A total of n×n clones are contained. When x is an arbitrary value, the clones belonging to the same mixing pool are:

$\{(x,0,0),(x,1,0),(x,2,0) \ldots (x,n-1,0),$ $(x,0,1),(x,1,1),(x,2,1) \ldots (x,n-1,1),$ $(x,0,2),(x,1,2),(x,2,2) \ldots (x,n-1,2),$ $(x,0,3),(x,1,3),(x,2,3) \ldots (x,n-1,3),$ $\ldots$ $(x,0,n-1),(x,1,n-1),(x,2,n-1) \ldots (x,n-1,n-1)\}$ In this way, n mixing pools can be obtained. Similar to PY, PX and PZ can also be constructed out of N mixing pool, respectively.

In OX, the plane intersected with the cube is perpendicular to the plane YOZ, and the slope of the projection line on the YOZ plane is −1. When the projection of the plane on the plane YOZ is a diagonal line (the white box line in OX in FIG. 3), then all the clones with white markers in the figure are the same mixing pool. When the projection of the plane on the plane YOZ is not a diagonal line, then the clones at the intersected position of the two planes and the cube are merged into one mixing pool. Such as the clones marked with black and white grid in the figure, the projection position of the corresponding two plates on plate YOX is linear y=−z+2 and linear y=−z+(2n+2). In the same way, it will get n mixing pools and each mixing pool contains n×n clones.

Similarly, n mixing pools are obtained in OY, OZ and OX, each mixing pool contains n×n clones.

AX can refer to the OX, but it is different from OX in that the slope of the projection line of the plane intersected with cube on the plane YOZ is 1. AY and AZ can refer to OY and OZ respectively.

Each strategy is to get n mixing pools, and each mixing pool contains n×n clones, so that the total length of the genome segment in each pool is as close as possible. The pool dimension refers to the total times of each clone appeared in all the mixing pools when construct mixing pools. For example, 3D pool can contain the mixing pools constructed by PX, PY and PZ or any other three cubes; 6D pool and 9D pool are similar to 3D pool. In order to position a clone, it needs three different dimension pools at least, but not 3 arbitrary mixing pools can position a clone. For instance, in 84 combination results of all the 3 arbitrary mixing pools listed in Table 1, 69 combinations can determine the clone position. Three mixing pools can position a clone, then 6 mixing pools can position the same clone for twice or 9 mixing pools can position the same clone for three times. If reorder the clone position in the cube, it can get a new cube, and the new cube can construct 9 pools, so as to get higher dimension pools to improve the accuracy and quality.

TABLE 1

Combination Results of Three Mixing Pools in 9 Clone Mixing Pools

| NO. | Pool 1 | Pool 2 | Pool 3 | Is Unique |
|---|---|---|---|---|
| 1 | AX | AY | AZ | FALSE |
| 2 | AX | AY | PX | TRUE |
| 3 | AX | AY | PY | TRUE |
| 4 | AX | AY | PZ | TRUE |
| 5 | AX | AY | OX | TRUE |
| 6 | AX | AY | OY | TRUE |
| 7 | AX | AY | OZ | TRUE |
| 8 | AX | AZ | PX | TRUE |
| 9 | AX | AZ | PY | TRUE |
| 10 | AX | AZ | PZ | TRUE |
| 11 | AX | AZ | OX | TRUE |
| 12 | AX | AZ | OY | TRUE |
| 13 | AX | AZ | OZ | TRUE |
| 14 | AX | PX | PY | TRUE |
| 15 | AX | PX | PZ | TRUE |
| 16 | AX | PX | OX | TRUE |
| 17 | AX | PX | OY | TRUE |
| 18 | AX | PX | OZ | TRUE |
| 19 | AX | PY | PZ | FALSE |
| 20 | AX | PY | OX | FALSE |
| 21 | AX | PY | OY | TRUE |

TABLE 1-continued

Combination Results of Three Mixing Pools in 9 Clone Mixing Pools

| NO. | Pool 1 | Pool 2 | Pool 3 | Is Unique |
|---|---|---|---|---|
| 22 | AX | PY | OZ | TRUE |
| 23 | AX | PZ | OX | FALSE |
| 24 | AX | PZ | OY | TRUE |
| 25 | AX | PZ | OZ | TRUE |
| 26 | AX | OX | OY | TRUE |
| 27 | AX | OX | OZ | TRUE |
| 28 | AX | OY | OZ | FALSE |
| 29 | AY | AZ | PX | TRUE |
| 30 | AY | AZ | PY | TRUE |
| 31 | AY | AZ | PZ | TRUE |
| 32 | AY | AZ | OX | TRUE |
| 33 | AY | AZ | OY | TRUE |
| 34 | AY | AZ | OZ | TRUE |
| 35 | AY | PX | PY | TRUE |
| 36 | AY | PX | PZ | FALSE |
| 37 | AY | PX | OX | TRUE |
| 38 | AY | PX | OY | FALSE |
| 39 | AY | PX | OZ | TRUE |
| 40 | AY | PY | PZ | TRUE |
| 41 | AY | PY | OX | TRUE |
| 42 | AY | PY | OY | TRUE |
| 43 | AY | PY | OZ | TRUE |
| 44 | AY | PZ | OX | TRUE |
| 45 | AY | PZ | OY | FALSE |
| 46 | AY | PZ | OZ | TRUE |
| 47 | AY | OX | OY | TRUE |
| 48 | AY | OX | OZ | FALSE |
| 49 | AY | OY | OZ | TRUE |
| 50 | AZ | PX | PY | FALSE |
| 51 | AZ | PX | PZ | TRUE |
| 52 | AZ | PX | OX | TRUE |
| 53 | AZ | PX | OY | TRUE |
| 54 | AZ | PX | OZ | FALSE |
| 55 | AZ | PY | PZ | TRUE |
| 56 | AZ | PY | OX | TRUE |
| 57 | AZ | PY | OY | TRUE |
| 58 | AZ | PY | OZ | FALSE |
| 59 | AZ | PZ | OX | TRUE |
| 60 | AZ | PZ | OY | TRUE |
| 61 | AZ | PZ | OZ | TRUE |
| 62 | AZ | OX | OY | FALSE |
| 63 | AZ | OX | OZ | TRUE |
| 64 | AZ | OY | OZ | TRUE |
| 65 | PX | PY | PZ | TRUE |
| 66 | PX | PY | OX | TRUE |
| 67 | PX | PY | OY | TRUE |
| 68 | PX | PY | OZ | FALSE |
| 69 | PX | PZ | OX | TRUE |
| 70 | PX | PZ | OY | FALSE |
| 71 | PX | PZ | OZ | TRUE |
| 72 | PX | OX | OY | TRUE |
| 73 | PX | OX | OZ | TRUE |
| 74 | PX | OY | OZ | TRUE |
| 75 | PY | PZ | OX | FALSE |
| 76 | PY | PZ | OY | TRUE |
| 77 | PY | PZ | OZ | TRUE |
| 78 | PY | OX | OY | TRUE |
| 79 | PY | OX | OZ | TRUE |
| 80 | PY | OY | OZ | TRUE |
| 81 | PZ | OX | OY | TRUE |
| 82 | PZ | OX | OZ | TRUE |
| 83 | PZ | OY | OZ | TRUE |
| 84 | OX | OY | OZ | TRUE |

"TRUE" in the table indicates that the intersection of the three mixing pools only has one clone, "FALSE" indicates that the intersection of these three mixing pools has more than 1 clone. When construct the mixing pool, it is best to choose the three mixing pools combination which can position one clone.

Select 4096 clones from the BAC library and put into a 16×16×16 cube. Select the PX, PY, PZ, OX, OY and OZ to construct 6 dimension mixing pool (if there are higher quality requirements, construct 9 dimension mixing pool, or higher dimension). Each dimension has 16 mixing pools, a total of 96 mixing pools, and each mixing pool contains 256 clones.

96 mixing pools with their clone number are as follows:

TABLE 2

Mixing Pool and Corresponding Clone Numbers contained therein

| | |
|---|---|
| PX0 | 1225, 68, 509, 3904, 1472, 651, 3210, 249, 1296, 2442, 3577, 3968, 1766, 3777, 1054, 4049, 1191, 3616, 3239, 3816, 3307, 1370, 3471, 3078, 3807, 3345, 4075, 1909, 1469, 665, 3243, 236, 3294, 217, 2104, 2738, 3708, 316, 3218, 3614, 2051, 2367, 3639, 2776, 3547, 780, 641, 2817, 2073, 3438, 3679, 3678, 4083, 3939, 2440, 1266, 543, 238, 1133, 1543, 1927, 3844, 806, 3355, 378, 3876, 2435, 3188, 1865, 193, 1451, 3985, 689, 1839, 825, 1590, 1836, 3919, 403, 334, 2652, 1889, 1768, 568, 3404, 3401, 3944, 2473, 55, 3494, 418, 227, 1846, 1038, 4036, 2084, 1950, 837, 1995, 4062, 1073, 455, 2450, 325, 1249, 371, 3922, 92, 935, 3032, 3026, 208, 1663, 3778, 3153, 2851, 658, 3036, 2934, 2097, 2746, 2908, 3684, 1920, 345, 3732, 1943, 1075, 3894, 1763, 823, 4127, 2936, 2265, 482, 1852, 964, 1261, 1829, 798, 2988, 1918, 3015, 2535, 1278, 583, 3418, 3209, 2491, 145, 3000, 1769, 3983, 3749, 2519, 939, 2855, 3273, 1365, 3425, 2314, 414, 2364, 3267, 3858, 1188, 2275, 3963, 1496, 3099, 3859, 190, 764, 36, 3446, 223, 3431, 2281, 1687, 1264, 3051, 3358, 2919, 3392, 2342, 2433, 3582, 1643, 1877, 2242, 2610, 2502, 2015, 1203, 1335, 513, 3747, 2465, 347, 235, 1826, 2865, 749, 726, 3499, 803, 1288, 3872, 41, 2730, 3837, 358, 3021, 2263, 794, 501, 535, 1338, 778, 1103, 1238, 4064, 943, 1799, 244, 2339, 1229, 1321, 3755, 1526, 1696, 3353, 3040, 173, 2873, 971, 1456, 631, 311, 2891, 2066, 3238, 2819, 450, 2850, 1723, 3824, 104, 3264, 618, 1998, 810, 3171, 3761, 3663, 3091 |
| PX1 | 2151, 2086, 3656, 2895, 2699, 226, 1757, 3580, 1315, 192, 1821, 2053, 4016, 2276, 1068, 382, 3597, 808, 95, 965, 2270, 968, 105, 1561, 2962, 3457, 70, 480, 4132, 1300, 813, 3105, 3333, 763, 2353, 1282, 1101, 2437, 3440, 1307, 169, 2893, 2771, 2061, 2516, 2791, 3350, 3716, 774, 3205, 2239, 3159, 4117, 1314, 1665, 3289, 784, 868, 1925, 1778, 2661, 3411, 3172, 3814, 1172, 1926, 2102, 572, 4172, 90, 4135, 2527, 4024, 1525, 1376, 2707, 3905, 4088, 1507, 562, 4171, 1137, 1044, 1599, 1597, 1734, 3351, 2044, 886, 731, 3506, 1104, 3893, 4176, 1649, 3875, 3866, 1474, 2063, 3097, 3862, 595, 3300, 1883, 830, 4179, 2479, 353, 491, 274, 2384, 2012, 2745, 3278, 3792, 134, 1063, 1176, 3016, 237, 876, 761, 2769, 2174, 1869, 2497, |

TABLE 2-continued

Mixing Pool and Corresponding Clone Numbers contained therein

|  |  |
|---|---|
|  | 3902, 851, 1209, 1969, 2579, 2766, 2573, 3050, 1980, 4013, 101, 2269, 2082, 3508, 4030, 2826, 2166, 1313, 904, 1654, 585, 850, 377, 1948, 2621, 2402, 2238, 3084, 1521, 2969, 1814, 2525, 3791, 567, 4010, 198, 2676, 2136, 1329, 2609, 3394, 1999, 642, 646, 3299, 3561, 2421, 2079, 2949, 4091, 2645, 1243, 361, 4057, 4129, 789, 843, 2282, 171, 2072, 189, 2671, 922, 3645, 986, 2303, 546, 3365, 2634, 3999, 199, 3012, 1040, 18, 1433, 3961, 3109, 9, 3279, 744, 3341, 2614, 2350, 1306, 2871, 2098, 1434, 2190, 2541, 1691, 3548, 2145, 1457, 335, 3108, 2288, 2312, 3403, 3285, 3044, 2921, 2784, 3302, 2149, 2379, 1686, 3123, 3033, 2022, 1823, 1379, 1142, 2646, 3253, 2834, 1079, 313, 4041, 3242, 3503, 1912, 1053, 2374, 187, 2408, 205, 1719, 2996, 2032, 1085 |
| PX2 | 44, 3810, 2152, 159, 317, 2567, 1443, 49, 2720, 3592, 2585, 630, 2744, 620, 3599, 2125, 1476, 3224, 2355, 2526, 395, 884, 77, 38, 3975, 81, 827, 4032, 1280, 2214, 3164, 606, 2907, 1146, 2424, 1358, 259, 3915, 2474, 2869, 3531, 333, 3874, 2555, 3173, 1655, 1050, 1417, 1973, 65, 166, 3911, 4139, 96, 3250, 3490, 1698, 379, 3135, 3045, 94, 2723, 10, 2584, 1904, 1259, 1092, 1131, 1961, 116, 1240, 2389, 518, 1954, 3705, 3827, 1996, 1174, 203, 648, 3870, 1928, 747, 2961, 1419, 3728, 1328, 221, 2222, 3342, 475, 5, 2092, 2003, 4063, 1124, 1942, 2878, 2223, 3710, 3074, 3598, 175, 2067, 506, 1594, 3721, 359, 411, 2216, 1494, 3184, 1166, 3982, 2623, 3720, 3479, 1454, 3637, 1486, 2679, 836, 2059, 2165, 3193, 1756, 1122, 2308, 1803, 1436, 3718, 2914, 3290, 2531, 2121, 923, 266, 653, 519, 776, 2430, 2268, 3422, 2701, 1630, 3497, 1190, 391, 3812, 604, 2926, 3376, 1854, 2091, 1985, 2396, 2033, 2898, 61, 751, 4000, 329, 3458, 1688, 4092, 389, 1736, 2752, 1355, 3602, 1397, 2007, 2078, 4061, 2862, 1790, 3524, 2316, 3154, 3707, 2590, 3879, 2974, 3346, 2096, 3632, 2219, 2917, 3313, 536, 3468, 1861, 3945, 481, 2398, 3191, 3677, 331, 1695, 777, 34, 3426, 430, 1029, 2414, 947, 3591, 3011, 3795, 280, 2099, 4126, 732, 1414, 2120, 2815, 479, 650, 3955, 880, 136, 1584, 1957, 4042, 3610, 58, 1604, 484, 677, 3609, 2880, 717, 3929, 2777, 3062, 1194, 1134, 28, 3917, 872, 582, 263, 2984, 1322, 133, 1088, 2894, 118, 2778, 1834, 1793, 720, 248, 1508, 804, 2870 |
| PX3 | 3661, 286, 2711, 1997, 3676, 2185, 578, 3578, 1827, 750, 2133, 3232, 1745, 64, 2835, 701, 2080, 3558, 2284, 1187, 1619, 2665, 2739, 2183, 1555, 2725, 2559, 2742, 346, 2320, 4086, 2754, 367, 1298, 1743, 2359, 2820, 1931, 1570, 785, 1175, 2403, 2005, 243, 2439, 4151, 3427, 2802, 1199, 1908, 492, 4095, 2283, 1714, 3842, 759, 3115, 1334, 627, 1381, 3070, 1380, 1244, 2542, 4008, 1519, 413, 3268, 3335, 781, 1612, 2130, 815, 30, 1822, 3094, 1550, 581, 3746, 2935, 574, 611, 3516, 2483, 2696, 152, 219, 1438, 3197, 3472, 113, 4087, 1541, 1583, 766, 871, 2653, 1108, 706, 3228, 3920, 449, 3552, 897, 12, 3775, 537, 3910, 1100, 1884, 3199, 2695, 99, 1886, 2867, 1820, 3314, 2568, 4029, 1539, 675, 1410, 637, 1581, 3283, 2806, 502, 3730, 3989, 156, 1552, 1179, 802, 1540, 1247, 1989, 1781, 2514, 2419, 2028, 2213, 3734, 710, 3714, 2812, 3991, 539, 215, 938, 2705, 937, 308, 2698, 700, 1230, 4054, 1585, 3460, 2586, 892, 3306, 440, 488, 2677, 4111, 580, 881, 987, 1732, 1195, 1361, 2300, 2843, 3793, 1009, 1701, 3801, 1114, 4143, 3056, 1530, 3535, 124, 2816, 1082, 3540, 3848, 596, 3890, 1241, 2684, 3398, 2588, 1915, 420, 768, 4152, 3071, 1697, 1169, 4113, 2666, 1536, 3198, 895, 2992, 3247, 3214, 3735, 3195, 858, 833, 1676, 3231, 4066, 2153, 1294, 1250, 4146, 2801, 4050, 3600, 2024, 2764, 1369, 2496, 3451, 716, 493, 782, 1946, 2400, 1200, 2456, 110, 2932, 3588, 2945, 3028, 926, 2507, 1705, 1012, 1270, 3840, 2376, 3774, 71, 3753, 4107, 1801, 4108, 2814, 2405, 3416, 3669 |
| PX4 | 1362, 356, 1372, 3147, 2846, 3941, 663, 1283, 1777, 3027, 262, 428, 239, 2790, 3918, 1093, 869, 911, 32, 3947, 4097, 1685, 2977, 3649, 1917, 1760, 1645, 1932, 982, 916, 2630, 1091, 1468, 990, 1185, 3943, 2548, 2920, 3113, 1637, 4084, 2013, 3817, 3309, 3254, 3075, 2566, 3681, 3266, 2127, 862, 1800, 3654, 2031, 1130, 330, 2228, 3927, 1740, 1083, 3800, 1776, 2184, 3347, 2095, 1424, 3052, 1515, 194, 4158, 3464, 4003, 1518, 1602, 3366, 929, 4124, 1930, 899, 2647, 2293, 1809, 1, 2887, 20, 4098, 2199, 628, 3201, 1983, 559, 1326, 832, 2107, 3493, 1730, 2957, 1202, 298, 1470, 4116, 2724, 3080, 1805, 718, 1449, 3363, 3339, 3860, 214, 3674, 1922, 999, 866, 2200, 753, 2280, 3158, 2889, 2277, 3125, 241, 3965, 2553, 2643, 2204, 2198, 4145, 1632, 2040, 799, 2909, 2763, 1959, 247, 2049, 410, 1748, 270, 681, 3564, 3841, 2461, 2944, 2710, 3039, 2361, 355, 2642, 3589, 3186, 2612, 1389, 1316, 339, 3532, 3257, 3496, 1039, 2782, 877, 3815, 2952, 1407, 2946, 3950, 1787, 3743, 3449, 874, 1631, 398, 1849, 3628, 3832, 499, 2860, 800, 287, 3138, 140, 1080, 1255, 1071, 647, 521, 2459, 2712, 2250, 621, 3854, 3946, 4047, 1546, 2775, 2597, 1841, 2143, 439, 1251, 2956, 1265, 3485, 2215, 50, 3139, 3900, 3671, 3888, 950, 2538, 3846, 406, 292, 3615, 755, 714, 1794, 2767, 3492, 914, 1798, 756, 2167, 3584, 1505, 2048, 342, 934, 3739, 4051, 1045, 1833, 609, 1403, 22, 3906, 1227, 1275, 85, 2240, 4121, 1795, 2195, 2550, 155, 2708, 1860, 2557, 3897, 556, 1586, 538, 1835, 4128, 1848 |
| PX5 | 122, 1974, 3510, 931, 3647, 1164, 3244, 2129, 4040, 984, 1421, 910, 2349, 3685, 2916, 2998, 3144, 3667, 2106, 1962, 3067, 2999, 1497, 831, 741, 89, 2672, 165, 97, 1652, 2824, 624, 1566, 2038, 1440, 416, 469, 1028, 366, 1402, 2244, 2702, 3940, 1301, 3152, 2004, 765, 2911, 3129, 2064, 2318, 715, 1467, 1774, 1894, 841, 1106, 1819, 2447, 3960, 3731, 2704, 3362, 1671, 854, 3733, 550, 245, 299, 4168, 4170, 350, 523, 3757, 45, 2781, 2965, 2863, 3435, 3804, 983, 2810, 3742, 969, 1674, 332, 3546, 3687, 1151, 3369, 3630, 3430, 2304, 3151, 460, 2828, 3925, 1201, 1831, 1034, 2890, 1426, 920, 3644, 3337, 2454, 3636, 1978, 1788, 1755, 3657, 1953, 1423, 2565, 3556, 915, 1487, 2923, 2734, 2186, 464, 1902, 2393, 962, 2017, 2942, 2482, 441, 1638, 2469, 1706, 4068, 3694, 117, 3260, 2648, 1735, 75, 3410, 157, 3041, 2830, 446, 120, 3185, 3066, 2475, 393, 3390, 211, 4089, 730, 384, 2877, |

TABLE 2-continued

Mixing Pool and Corresponding Clone Numbers contained therein

|  |  |
|---|---|
|  | 1844, 1832, 1125, 2882, 87, 3557, 79, 1374, 1231, 867, 1363, 3461, 3003, 2232, 471, 2800, 3131, 3585, 1807, 1635, 3133, 2416, 3121, 7, 1018, 957, 128, 4177, 1935, 592, 1758, 557, 2827, 3265, 1095, 597, 1462, 1567, 2587, 3312, 1319, 2109, 402, 2941, 3162, 2626, 2235, 1327, 3325, 51, 737, 474, 3323, 3441, 2629, 956, 932, 1885, 2943, 2522, 719, 2016, 3737, 3463, 1409, 1888, 3072, 2358, 875, 1215, 1718, 1126, 1659, 234, 4120, 294, 1976, 1299, 408, 1966, 3382, 2338, 222, 1667, 1375, 4166, 1498, 1492, 2925, 2119, 743, 1371, 374, 3124, 2838, 1163, 3650, 3428, 3933, 2249, 489, 2892 |
| PX6 | 255, 2658, 1944, 1991, 3593, 2904, 3754, 2841, 526, 1113, 438, 2853, 2918, 3293, 2861, 3568, 1704, 2733, 2202, 2251, 2002, 3029, 2426, 1772, 2521, 2328, 2924, 388, 3088, 2560, 473, 2356, 2428, 3227, 3202, 958, 106, 2884, 31, 826, 3146, 1855, 197, 3736, 2363, 495, 2569, 822, 3990, 301, 303, 1236, 369, 1568, 3601, 722, 645, 2029, 363, 1112, 3280, 1181, 1036, 3005, 524, 1979, 3618, 1933, 112, 4093, 1003, 2205, 959, 2929, 3216, 3149, 505, 3700, 154, 3719, 2650, 53, 2564, 1173, 1744, 218, 786, 4090, 1267, 319, 1905, 1162, 4025, 2116, 901, 2950, 1626, 2323, 1963, 1337, 1180, 1007, 2537, 1675, 1711, 1290, 195, 1863, 1025, 2460, 461, 1383, 3693, 2973, 2425, 3664, 997, 1639, 2311, 3102, 3972, 1210, 3820, 2930, 2124, 3406, 23, 1708, 2735, 1986, 57, 936, 1622, 3206, 269, 1563, 93, 2613, 2761, 2703, 1709, 3507, 151, 3402, 1184, 425, 896, 1668, 4059, 849, 3528, 150, 2196, 3025, 3912, 1538, 2252, 4001, 494, 143, 3808, 3466, 981, 1056, 2697, 3467, 1303, 158, 793, 1867, 63, 1171, 1754, 3523, 2218, 1350, 654, 1161, 917, 146, 3136, 4072, 3119, 2902, 3550, 2137, 1445, 3295, 3352, 3660, 2462, 478, 3996, 240, 2259, 3328, 3475, 912, 2305, 3059, 1147, 507, 47, 817, 3847, 3895, 2449, 2189, 2578, 3208, 629, 1856, 528, 1344, 4052, 2413, 100, 1105, 3276, 1871, 3413, 842, 246, 2686, 423, 1168, 3169, 2409, 3378, 252, 1872, 3357, 2822, 1144, 3318, 898, 2, 1274, 3514, 2727, 2261, 2678, 2390, 3284, 1178, 2334, 679, 1792, 1818, 2875, 1578, 3722, 1471, 3520, 1608, 3949 |
| PX7 | 608, 1868, 560, 102, 1235, 2233, 3167, 3336, 1461, 1385, 103, 612, 2495, 2415, 1666, 4142, 1223, 1952, 2852, 3456, 589, 2160, 3142, 1248, 2670, 1684, 3951, 1253, 4141, 27, 2635, 829, 1511, 2922, 3397, 444, 996, 847, 1272, 1366, 179, 364, 1084, 2985, 2131, 2976, 3751, 652, 3863, 2427, 1167, 2273, 913, 1656, 966, 769, 160, 2392, 91, 3014, 1572, 1353, 1919, 930, 2336, 2234, 2260, 2180, 1390, 188, 114, 2971, 1204, 918, 1573, 1617, 2333, 2500, 2140, 1069, 992, 2262, 2789, 2845, 127, 927, 182, 1727, 3505, 2169, 1347, 2958, 3442, 695, 598, 3780, 1907, 2955, 522, 1715, 1437, 1165, 1258, 1027, 1052, 613, 162, 67, 2229, 1627, 3555, 500, 291, 2100, 3018, 3619, 3437, 3830, 2150, 2594, 3680, 1254, 1061, 1681, 2423, 2968, 1537, 433, 2065, 1770, 407, 814, 1717, 3137, 253, 1359, 2504, 387, 3857, 1435, 1582, 993, 3835, 2547, 3296, 1808, 3269, 1160, 3474, 1019, 3148, 1116, 1517, 2088, 2335, 3502, 1513, 1903, 2069, 3263, 297, 2441, 1672, 703, 3937, 1213, 1291, 275, 1135, 2018, 3204, 1324, 2010, 1148, 527, 1138, 4079, 467, 3196, 1987, 748, 3901, 3631, 3058, 33, 3981, 2455, 2340, 1463, 1648, 3869, 278, 1413, 3683, 2401, 1699, 3270, 671, 477, 661, 1489, 1388, 448, 1523, 4114, 3608, 191, 1825, 445, 3486, 3887, 176, 2619, 3319, 3868, 2993, 368, 4104, 3913, 2994, 3698, 3261, 3984, 52, 401, 2649, 738, 3595, 490, 2144, 3622, 2369, 3212, 3695, 132, 2310, 1994, 1679, 2330, 3914, 3222, 855, 1485, 3988, 2154, 3217, 552, 2457, 2257, 566, 115, 1693, 3682, 809, 2446, 2313 |
| PX8 | 2740, 3049, 670, 3767, 2383, 3459, 2128, 2453, 3106, 758, 1446, 2132, 3594, 2042, 1047, 1783, 564, 4015, 2395, 1859, 853, 3970, 952, 2394, 213, 796, 2979, 4165, 1022, 3907, 2175, 3545, 1394, 1759, 3572, 1896, 835, 1352, 210, 2939, 3576, 2552, 2779, 60, 496, 1268, 531, 3453, 547, 1694, 4020, 1764, 3174, 4154, 277, 1955, 1232, 2574, 1680, 2874, 1252, 1661, 1673, 1837, 3332, 3539, 2345, 3786, 3769, 3259, 1295, 2636, 1064, 3407, 336, 1588, 2141, 4169, 3281, 1239, 682, 686, 767, 3729, 2192, 306, 1005, 2583, 1804, 4033, 3477, 1302, 3567, 3436, 2694, 2406, 614, 3931, 2077, 659, 1078, 625, 3203, 2589, 2518, 265, 1066, 1448, 1086, 2825, 3434, 2743, 1501, 2037, 2551, 3262, 1339, 811, 2458, 2995, 2809, 3838, 4056, 1544, 3010, 2660, 2654, 3828, 3004, 2382, 1600, 1571, 80, 1968, 713, 1870, 3326, 1738, 3001, 725, 2348, 1784, 1815, 2709, 2420, 1703, 1096, 508, 326, 1556, 1596, 1614, 558, 746, 1332, 3086, 2254, 1170, 2417, 3089, 2657, 1226, 1157, 3180, 4149, 442, 2682, 980, 2580, 3019, 1746, 3764, 1940, 2045, 3843, 1242, 3386, 2388, 1782, 1564, 2639, 664, 2287, 4077, 1937, 2523, 3575, 4028, 3277, 1465, 4159, 1524, 3500, 3967, 2274, 3501, 599, 3161, 3666, 985, 1824, 2271, 656, 3962, 357, 2008, 775, 3781, 3462, 3399, 1070, 6, 3823, 839, 109, 148, 1401, 2795, 3176, 3818, 323, 1558, 1129, 1534, 216, 2951, 121, 3574, 3303, 3559, 1277, 3150, 1993, 970, 3008, 1900, 4, 1411, 1677, 3583, 2785, 2290, 976, 2607, 3081, 1447, 3886, 3992, 2799, 1972, 2203, 2489, 2399, 242, 3635, 3634 |
| PX9 | 2593, 3659, 1444, 1611, 1495, 84, 2680, 2444, 3020, 1634, 2683, 565, 2749, 1728, 852, 399, 2126, 2387, 1657, 3409, 3385, 1899, 668, 2558, 3958, 3379, 1046, 1956, 1810, 1512, 2118, 2052, 1336, 787, 3625, 3942, 3867, 600, 2060, 690, 4082, 1024, 773, 3607, 2164, 454, 2879, 1081, 295, 1150, 4011, 178, 1796, 2631, 271, 3372, 2625, 998, 3423, 1618, 975, 2386, 1545, 3448, 385, 2794, 727, 1958, 883, 3802, 2039, 3527, 1500, 3301, 1320, 285, 3054, 2294, 2501, 3969, 250, 887, 588, 1761, 708, 2117, 2844, 4122, 3697, 903, 2391, 3690, 3359, 4037, 1121, 2722, 740, 3977, 3371, 1916, 1510, 1813, 4102, 1099, 4178, 1004, 180, 231, 4035, 1368, 2123, 4123, 3116, 177, 19, 3189, 2539, 2103, 3670, 3252, 3652, 905, 2599, 4065, 435, 623, 288, 3251, 1452, 3083, 1387, 3784, 4133, 2964, 1477, 2019, 462, 1514, 457, 2823, 2046, 2549, 3773, 4069, 2728, 4157, 3702, 451, 3772, 2058, 4100, 3450, 2267, 1090, 2640, 978, 2344, 206, 683, 1858, 561, 421, 3790, 3288, 1033, 2772, 3310, 2380, 605, 925, 1207, 1499, 3672, 548, 1420, 1690, 2341, 2520, 2897, 365, 3469, 86, |

TABLE 2-continued

Mixing Pool and Corresponding Clone Numbers contained therein

|  |  |
|---|---|
|  | 3973, 3976, 3322, 2954, 310, 4081, 4101, 762, 2470, 185, 3822, 2868, 2787, 1197, 2511, 289, 3948, 816, 1246, 2047, 900, 1109, 3658, 1364, 2208, 2142, 3569, 2747, 3831, 24, 2760, 383, 2786, 3344, 1503, 1216, 2113, 1592, 370, 2241, 3797, 907, 2157, 397, 3327, 1533, 4099, 1700, 3959, 3043, 1562, 2105, 963, 3, 4053, 328, 770, 1724, 2691, 2083, 2326, 225, 1898, 1842, 2194, 941, 828, 2616, 2090, 1205, 2940, 1404, 3364, 3998 |
| PX10 | 1089, 2302, 848, 3688, 2487, 56, 2477, 2135, 1532, 3643, 2054, 906, 1843, 1001, 1488, 1554, 1765, 1418, 2034, 3957, 3563, 338, 3219, 3611, 2980, 2253, 66, 3024, 1658, 40, 3183, 2468, 1975, 2603, 354, 891, 1660, 820, 2443, 1911, 783, 2486, 3145, 2849, 304, 3525, 3526, 3367, 161, 3013, 2983, 594, 1062, 1293, 1616, 2295, 1990, 1032, 3258, 615, 3864, 1431, 1118, 3160, 2036, 1153, 724, 2354, 1287, 2081, 687, 324, 3562, 2068, 924, 2681, 2554, 3412, 0, 3482, 2056, 2606, 2854, 2210, 2687, 893, 1484, 1502, 1077, 3454, 3229, 72, 2536, 2796, 2615, 2381, 2494, 2627, 3230, 4058, 396, 2006, 1623, 1415, 174, 1873, 1325, 3655, 2534, 3768, 3478, 4078, 3433, 4067, 3194, 35, 1048, 2488, 2161, 267, 3421, 3063, 4094, 4085, 1984, 3170, 1644, 1992, 4048, 1864, 2027, 3974, 3248, 3155, 3979, 2448, 3573, 228, 483, 3855, 3604, 1102, 2532, 2591, 2938, 264, 1464, 3085, 873, 1491, 3590, 1008, 698, 3954, 3473, 1816, 434, 337, 1041, 1015, 1621, 3009, 2451, 3885, 4009, 3571, 3798, 3686, 2883, 1177, 1305, 1143, 3165, 1615, 721, 2041, 232, 4060, 2168, 821, 4076, 1279, 771, 3419, 569, 545, 3581, 2888, 788, 3633, 422, 2187, 1721, 2014, 1713, 1260, 2915, 3122, 3282, 1262, 4115, 3665, 2289, 3271, 3849, 699, 807, 3542, 1055, 2236, 3738, 21, 657, 610, 2513, 3432, 1466, 3785, 2808, 1030, 1965, 2220, 2089, 1149, 3883, 520, 73, 3120, 2628, 4140, 712, 3642, 2372, 2362, 486, 3605, 1000, 376, 1367, 2478, 1343, 961, 3317, 1892, 818, 309, 2982, 1739, 3839, 3022, 1773, 3553, 2026, 2805, 2953, 3646 |
| PX11 | 201, 1910, 29, 1408, 3586, 320, 1351, 3549, 1624, 98, 2411, 2110, 3200, 2231, 351, 3640, 4136, 3127, 3320, 1753, 3447, 2509, 4071, 919, 1605, 3668, 1478, 3971, 254, 172, 3993, 3517, 1400, 3771, 1876, 3829, 693, 640, 1152, 2163, 3361, 2545, 3596, 3787, 2528, 2858, 3745, 4045, 1862, 273, 432, 3373, 139, 1589, 3483, 3871, 857, 4021, 3470, 2285, 1847, 3701, 2966, 1964, 2836, 593, 967, 167, 1432, 314, 164, 3551, 921, 1535, 1309, 3330, 2170, 757, 1023, 1159, 1669, 2803, 3519, 141, 1893, 2540, 1620, 2664, 2325, 3304, 3445, 2987, 622, 1111, 2368, 2837, 517, 2319, 315, 3175, 2592, 15, 704, 4162, 1960, 2864, 260, 2997, 4022, 3877, 3439, 78, 2770, 2147, 3324, 2112, 3620, 468, 2375, 694, 1340, 3126, 946, 1731, 2562, 1601, 1224, 1613, 4043, 1011, 183, 2070, 3565, 673, 3237, 2651, 3724, 2297, 908, 3613, 2412, 3498, 3852, 1123, 3291, 3069, 2797, 2517, 2177, 284, 649, 3298, 994, 3315, 1217, 3621, 1947, 380, 3889, 1218, 3225, 3924, 3098, 745, 2212, 1646, 1591, 3055, 130, 888, 107, 805, 2641, 3166, 3511, 3491, 3703, 281, 840, 83, 3930, 2206, 3709, 1360, 1806, 533, 2292, 2286, 2546, 2881, 2857, 163, 2418, 1186, 1548, 1356, 3717, 3380, 3093, 1628, 1606, 2668, 1560, 2466, 1771, 3826, 988, 272, 2508, 1967, 3966, 945, 1480, 119, 1493, 1779, 1609, 4002, 135, 2373, 795, 2429, 3758, 2885, 2663, 2700, 2191, 2050, 2352, 3587, 3952, 4074, 4055, 3220, 666, 1425, 692, 153, 3375, 1156, 2378, 2247, 1377, 300, 3112, 1042, 3292, 1057, 3308, 1458, 1670, 4155, 3061, 2227, 3249, 2750 |
| PX12 | 3130, 2023, 1982, 1906, 3980, 200, 2611, 144, 3964, 2644, 2237, 662, 16, 2172, 3343, 2217, 1520, 3782, 3134, 3287, 3179, 3235, 372, 2600, 74, 2937, 3926, 2410, 3340, 1879, 251, 2452, 1853, 3627, 2485, 3759, 1006, 4019, 1453, 4163, 2404, 59, 2713, 1642, 1528, 2347, 1812, 3689, 2148, 1221, 3141, 1021, 3103, 2179, 1913, 2248, 2434, 2601, 2255, 890, 3725, 626, 3117, 2490, 3513, 1002, 230, 283, 697, 678, 3997, 2737, 3420, 3443, 1789, 2445, 1971, 791, 3606, 2543, 3853, 2741, 3765, 2085, 2981, 3429, 1257, 318, 2736, 3178, 3415, 3095, 1292, 3851, 2256, 2370, 381, 3424, 4173, 390, 3986, 3334, 2197, 1416, 3017, 955, 392, 1775, 268, 1895, 1031, 497, 1331, 3544, 1192, 2689, 1720, 131, 1219, 735, 2598, 3215, 1222, 1692, 3381, 3177, 4156, 2309, 4039, 1072, 3819, 3087, 1304, 3053, 977, 3246, 3938, 3240, 170, 4164, 1341, 1479, 3311, 2866, 3699, 4109, 296, 790, 2211, 2114, 2596, 1094, 412, 1412, 2226, 3023, 3286, 1286, 972, 1551, 602, 570, 3241, 1689, 3836, 3766, 3987, 2991, 2765, 2272, 2758, 1406, 2582, 1013, 909, 586, 1234, 1060, 3082, 1565, 25, 619, 3641, 1875, 4105, 2331, 878, 3763, 2872, 960, 1297, 1762, 709, 1430, 1988, 3898, 1330, 1682, 3101, 2397, 1399, 846, 643, 344, 1196, 4147, 1312, 1742, 3092, 2638, 108, 2134, 2856, 554, 2719, 1838, 261, 1576, 2176, 1929, 1625, 3740, 3396, 26, 636, 3881, 1459, 404, 555, 4023, 3518, 2732, 1115, 3603, 1455, 1851, 341, 1712, 2959, 360, 933, 1587, 1482, 752, 3331, 1010, 1384, 644, 3806, 257, 3770, 2989, 470, 1598, 942, 541 |
| PX13 | 1059, 529, 3226, 1516, 1569, 2913, 1786, 638, 1014, 142, 1139, 429, 3047, 1107, 3756, 2757, 1382, 587, 2332, 1405, 3953, 3880, 1897, 1939, 3783, 476, 3190, 705, 639, 111, 1483, 3042, 2471, 4044, 954, 674, 129, 2360, 4012, 3538, 1710, 3037, 885, 1098, 1729, 736, 1357, 2178, 3809, 1527, 1269, 2225, 1722, 3712, 3560, 2011, 3691, 3522, 2571, 2903, 3762, 504, 2622, 2162, 2221, 1504, 1575, 2756, 1716, 2512, 220, 123, 779, 1653, 3480, 2960, 2716, 2899, 940, 466, 3921, 2464, 1640, 1349, 2690, 4131, 4073, 2298, 3234, 2327, 427, 2570, 1595, 1398, 204, 1140, 348, 3978, 3521, 4174, 3034, 48, 553, 894, 43, 459, 1058, 4103, 3128, 1580, 3221, 138, 2182, 3673, 1035, 3414, 3934, 3338, 2377, 2264, 711, 1924, 3114, 2146, 3624, 3408, 3132, 3861, 3484, 456, 2524, 207, 2910, 1333, 2751, 2900, 944, 1284, 2057, 2438, 3156, 2718, 2692, 2688, 928, 571, 2967, 685, 2595, 2076, 3662, 2798, 1934, 1373, 3833, 882, 2351, 974, 3865, 3711, 2605, 1141, 1067, 2357, 861, 3090, 2972, 3192, 2431, 2715, 3726, 2139, 4118, 386, 373, 4005, 844, 2436, 2515, 707, 125, 3356, 3570, 2990, 2055, 1529, 3064, 676, 417, 2818, 256, 2467, 3623, 1553, 3892, 3891, 2831, 1726, 498, 2463, 3370, 3065, 1281, 1845, 1097, 3534, 1182, 3579, |

TABLE 2-continued

Mixing Pool and Corresponding Clone Numbers contained therein

|      |                                                                                                                                                                                                                                                                                                                                                                                                                                                                                                                                                                                                                                                                                                                                                                                                                                                                                                                                                                                                                                                                                                                                                                                                                                                                                                                                                                  |
|------|------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------------|
|      | 3899, 3805, 530, 343, 742, 1208, 2721, 1651, 739, 2343, 902, 1938, 2912, 1901, 1393, 3936, 889, 2087, 772, 1026, 2385, 1378, 3255, 2472, 2624, 362, 202, 3794, 2667, 3444, 485, 1117, 3368, 2230, 3060, 838, 607, 2618, 1245, 1785, 1345, 1752, 634, 2632, 2905, 2207, 603, 436 |
| PX14 | 2155, 1128, 3104, 864, 3760, 1593, 3236, 3713, 2296, 702, 3653, 3873, 845, 680, 321, 2847, 1442, 2774, 819, 3612, 2266, 305, 633, 2307, 282, 2931, 2094, 1607, 3813, 2804, 728, 3903, 302, 1741, 426, 3882, 1874, 1392, 515, 2768, 2366, 544, 1110, 2346, 1887, 2544, 3896, 1206, 3079, 2662, 3157, 1662, 2821, 2324, 1891, 2927, 3504, 1074, 577, 3908, 3850, 4080, 870, 1214, 1750, 563, 3046, 3488, 258, 2122, 792, 1725, 1579, 4004, 1346, 2505, 3692, 181, 3799, 2840, 3207, 46, 419, 3543, 2896, 2025, 3706, 4006, 233, 4138, 4119, 1866, 3006, 1650, 667, 2780, 1354, 812, 684, 3405, 2158, 2859, 2493, 1574, 2577, 1183, 1636, 1549, 2101, 512, 4160, 1155, 2604, 3388, 2759, 137, 801, 2633, 1747, 1647, 2729, 2726, 979, 2617, 3383, 1945, 17, 3741, 3274, 3533, 1263, 1664, 4144, 1427, 635, 2714, 3476, 1610, 601, 1076, 375, 2506, 1531, 3213, 540, 3675, 3878, 1276, 2245, 405, 688, 1941, 229, 2321, 2301, 2322, 2602, 1395, 1490, 88, 437, 1914, 991, 2071, 989, 2291, 1460, 860, 453, 2876, 2279, 2906, 1880, 591, 126, 760, 1037, 3417, 2813, 669, 2901, 2608, 1127, 2970, 2717, 4038, 37, 734, 723, 754, 3704, 2043, 3452, 3515, 3481, 3256, 532, 2111, 2407, 3068, 1817, 352, 1473, 1506, 503, 3168, 3387, 797, 1878, 1198, 2001, 824, 1422, 1285, 168, 1396, 1119, 729, 2315, 3187, 1065, 660, 196, 2201, 1308, 1429, 76, 3223, 1289, 2755, 2181, 3512, 2492, 2278, 2422, 1629, 3305, 1557, 322, 2832, 184, 2093, 2829, 3048, 579, 2188, 834, 4112, 2246, 856, 2317, 2674, 3077, 2581, 2173, 3329 |
| PX15 | 1577, 3400, 617, 3035, 951, 2365, 3788, 1271, 1797, 2243, 463, 2673, 1559, 82, 3487, 1428, 514, 3389, 452, 1923, 2748, 3537, 1683, 3629, 3617, 2793, 1450, 1120, 1017, 1547, 1791, 973, 2659, 2481, 3163, 691, 2656, 3181, 2839, 879, 1828, 1951, 1391, 209, 2975, 2503, 2159, 3696, 1310, 2848, 4017, 4106, 632, 2432, 4014, 3384, 2669, 616, 1830, 3182, 1212, 1323, 1840, 4026, 2576, 1049, 2115, 1273, 1132, 443, 584, 2499, 2706, 2731, 2693, 3638, 2075, 525, 2224, 2533, 549, 4137, 2753, 2811, 3825, 4125, 3626, 4007, 655, 1237, 1890, 1633, 2928, 3038, 1043, 859, 3275, 42, 3073, 1949, 2000, 1881, 69, 3455, 2193, 2156, 3796, 3536, 8, 2948, 2886, 3648, 1311, 424, 1481, 1702, 3031, 3245, 2299, 3723, 3395, 3354, 276, 3744, 394, 2498, 4148, 3932, 3884, 733, 516, 1386, 62, 14, 1977, 2030, 2529, 2978, 1767, 147, 4046, 1780, 2062, 2021, 3143, 186, 3916, 534, 1441, 487, 149, 279, 409, 2620, 2655, 39, 510, 2561, 3928, 415, 1348, 3076, 2556, 3995, 3118, 3845, 863, 1189, 212, 590, 2783, 1136, 3391, 3096, 3321, 3779, 2510, 2480, 1051, 431, 2020, 3272, 2842, 1811, 2762, 447, 327, 293, 3100, 3377, 995, 3233, 2675, 3776, 4130, 4134, 3057, 1751, 4031, 3529, 1936, 3509, 3002, 2035, 465, 1850, 2575, 4110, 1158, 575, 3465, 1641, 312, 2476, 1970, 3715, 1020, 1707, 2833, 1509, 224, 4153, 3909, 3923, 1233, 2986, 2947, 3748, 3811, 511, 400, 4018, 1228, 1154, 1193, 2572, 1439, 1542, 4027, 3803, 3489, 2685, 3349, 2337, 3110, 696, 3935, 1475, 2171, 953, 1857, 2963, 472, 1921, 2792, 1981 |
| PY0  | 1577, 514, 2659, 1310, 2576, 549, 3275, 1311, 3884, 3143, 1348, 2510, 2675, 1158, 1233, 3489, 1128, 2774, 1741, 2662, 563, 46, 812, 3388, 3533, 3675, 1914, 3417, 3515, 1198, 1429, 2093, 3226, 2332, 954, 1269, 1575, 1640, 3521, 1035, 2524, 2967, 1067, 2515, 3892, 530, 772, 3060, 1906, 3287, 3759, 1021, 283, 2085, 390, 2689, 3087, 790, 1689, 1565, 3898, 2134, 404, 752, 3586, 3447, 693, 139, 1432, 1893, 2592, 3620, 3565, 2177, 2212, 3930, 3717, 1480, 2352, 3112, 56, 338, 820, 1293, 2081, 893, 2006, 2488, 3155, 1491, 3571, 1279, 3122, 610, 4140, 309, 2680, 668, 2060, 271, 2039, 2844, 4102, 3670, 1477, 4100, 3310, 3973, 3948, 2786, 3959, 2194, 2453, 2394, 2939, 1955, 2636, 2583, 2589, 2995, 1870, 1614, 980, 4077, 985, 148, 3150, 3992, 1461, 2670, 179, 160, 1204, 3505, 1052, 3680, 2504, 1517, 1135, 33, 1489, 368, 3212, 2257, 1113, 2328, 1855, 2029, 2929, 319, 1290, 1210, 2613, 3025, 1867, 2137, 507, 1105, 1144, 2875, 1421, 2672, 3940, 2447, 45, 3630, 3636, 2393, 3410, 1844, 3131, 2827, 3325, 1409, 3382, 3650, 428, 1932, 3309, 1083, 929, 1326, 3339, 2553, 681, 3532, 398, 2712, 2215, 3492, 22, 1586, 1745, 346, 2439, 3070, 1550, 1541, 1100, 3283, 2213, 1585, 2843, 3890, 895, 4050, 3588, 2814, 620, 2214, 1655, 2723, 1174, 2003, 2216, 1756, 2268, 2898, 4061, 536, 947, 1584, 28, 1508, 1068, 813, 3350, 3172, 1507, 1649, 2384, 3902, 2166, 3791, 2949, 986, 3341, 2312, 2646, 2032, 4049, 236, 2817, 3355, 334, 2084, 208, 1075, 2535, 3425, 223, 2502, 3872, 1799, 2891, 3091 |
| PY1  | 2155, 1442, 302, 3079, 1750, 3207, 1354, 2604, 3274, 540, 437, 1037, 3452, 1878, 1308, 184, 529, 587, 4044, 1527, 1504, 2464, 3978, 3673, 456, 571, 1141, 2436, 1553, 3805, 2087, 2230, 1982, 3134, 2485, 3141, 230, 3765, 4173, 1192, 3819, 296, 3241, 3082, 1988, 108, 1459, 1482, 1408, 1753, 3829, 3373, 167, 141, 3175, 2112, 2070, 2517, 745, 83, 1356, 945, 2050, 300, 2487, 3563, 1660, 1062, 1287, 2687, 396, 1048, 3248, 873, 4009, 4076, 2915, 657, 2628, 818, 84, 1899, 600, 2631, 3802, 2117, 1813, 2103, 2964, 2058, 2772, 86, 289, 383, 1700, 1842, 2128, 952, 210, 277, 1295, 1005, 3203, 2458, 713, 1596, 2682, 2287, 3666, 109, 1277, 3886, 3336, 1248, 1366, 769, 2971, 1727, 1027, 2594, 1359, 1116, 275, 3058, 661, 2993, 2369, 2457, 526, 2521, 3146, 645, 959, 1267, 1711, 3972, 93, 2196, 793, 3550, 1147, 100, 2822, 1818, 984, 89, 2702, 1819, 3757, 3369, 2454, 1902, 75, 2877, 2800, 557, 1327, 3463, 1966, 1163, 262, 1645, 3817, 1740, 3366, 559, 3363, 3965, 270, 339, 1631, 2459, 3485, 2767, 1403, 556, 3232, 2742, 243, 1381, 3094, 4087, 3910, 1581, 2028, 4054, 2300, 596, 3198, 2801, 2932, 4108, 2744, 1280, 3173, 94, 1996, 2092, 411, 3193, 2430, 2033, 2078, 3313, 2414, 136, 1134, 248, 2276, 1300, 2791, 3411, 4088, 4176, 274, 2497, 2826, 2525, 2079, 3645, 744, 2288, 1142, 2996, 1054, 3243, 641, 806, 403, 4036, 3026, 1943, 3015, 1365, 3446, 2610, 1288, 943, 311, 3663, 1428, |

TABLE 2-continued

Mixing Pool and Corresponding Clone Numbers contained therein

|     |     |
| --- | --- |
|     | 973, 3696, 4026, 2533, 859, 3648, 3932, 2021, 415, 3779, 3233, 4110, 3923, 3803, 1981 |
| PY2 | 1059, 1382, 2471, 3809, 2221, 3921, 348, 2182, 3484, 928, 2605, 844, 3623, 3899, 889, 3368, 2023, 3782, 3627, 1221, 1002, 2741, 3424, 3544, 1072, 4109, 570, 1060, 1430, 2638, 3881, 1587, 29, 3320, 1876, 432, 967, 3519, 315, 3324, 183, 2797, 3098, 840, 1548, 3966, 2191, 1377, 3688, 3957, 891, 594, 2354, 2210, 4058, 35, 3974, 3085, 3885, 821, 1260, 21, 3120, 1892, 1495, 3385, 3867, 1796, 883, 708, 1510, 2539, 4133, 3772, 1033, 3469, 2511, 2760, 4099, 1898, 3459, 3970, 1352, 4154, 3259, 306, 625, 811, 1968, 1556, 442, 664, 3161, 839, 3559, 1447, 3167, 3142, 1272, 966, 114, 182, 1258, 2150, 253, 3148, 1291, 3631, 477, 3868, 3622, 552, 2841, 1772, 826, 722, 2205, 4090, 1675, 3102, 1563, 150, 158, 2902, 3059, 2413, 3357, 1792, 4040, 741, 2244, 1106, 523, 1151, 3337, 464, 1735, 384, 471, 1758, 2235, 3737, 408, 2838, 3027, 1760, 2013, 3927, 1602, 1983, 1449, 241, 1748, 1316, 874, 521, 1265, 1794, 609, 3897, 2133, 2559, 2005, 627, 1822, 113, 537, 637, 2419, 1230, 1361, 3848, 1536, 4146, 110, 1801, 630, 4032, 2555, 3045, 3827, 5, 359, 2165, 776, 2396, 2007, 2917, 1029, 880, 1194, 720, 4016, 4132, 2516, 2661, 3905, 3893, 491, 1869, 4030, 1814, 2421, 922, 3279, 3108, 1379, 1719, 3777, 665, 780, 3844, 3919, 1038, 3032, 3732, 1918, 3273, 36, 2242, 803, 4064, 631, 3761, 3487, 1791, 2159, 1840, 2224, 1043, 2886, 4148, 2062, 3928, 3321, 995, 2575, 3909, 4027, 2792, 2847, 3903, 1206, 1214, 2840, 2780, 1155, 3741, 3213, 88, 760, 2043, 797, 2201, 2832, 3329 |
| PY3 | 3130, 1520, 1853, 2148, 3513, 3853, 381, 1331, 4039, 3699, 602, 1234, 709, 3092, 636, 933, 1910, 3127, 3771, 273, 593, 2803, 2319, 2147, 1011, 3069, 3924, 281, 1186, 1967, 2700, 2247, 848, 2034, 354, 2983, 724, 2854, 3230, 3194, 2027, 1464, 2451, 2168, 1713, 3738, 73, 3317, 1611, 3409, 3942, 178, 1958, 1761, 1916, 3189, 3784, 451, 3288, 365, 1197, 24, 1533, 225, 2383, 853, 835, 3174, 3769, 2192, 1078, 1339, 80, 326, 4149, 2639, 599, 3823, 3303, 3081, 2233, 2160, 847, 1656, 188, 927, 1165, 3830, 3137, 1019, 1213, 3901, 671, 3319, 2144, 3217, 3754, 2426, 31, 3601, 1003, 786, 2537, 2311, 269, 3528, 1303, 3119, 2305, 4052, 1872, 679, 2129, 831, 1402, 841, 350, 3687, 3644, 2186, 2648, 730, 2232, 592, 2626, 2016, 1299, 3124, 1777, 1917, 4084, 2228, 1518, 3201, 718, 3125, 410, 1389, 3449, 647, 2956, 714, 1833, 2557, 750, 2725, 2403, 1334, 30, 3472, 3775, 1410, 2514, 700, 1195, 3540, 2666, 1250, 2456, 4107, 2585, 827, 3874, 3135, 3705, 475, 3721, 2059, 519, 1985, 1397, 2219, 430, 3955, 3062, 1793, 2053, 480, 2061, 1778, 2707, 1104, 353, 2174, 3508, 2969, 3561, 2671, 9, 335, 1823, 205, 1766, 1469, 3547, 1927, 1836, 1846, 935, 345, 2988, 2855, 764, 1877, 3499, 1238, 1456, 3171, 82, 1547, 2503, 1323, 525, 3038, 2948, 2498, 1780, 2561, 3096, 3377, 1850, 4153, 1542, 1921, 321, 728, 3896, 870, 3799, 667, 4160, 17, 1531, 1490, 126, 3704, 3387, 196, 322, 2173, 2757, 3042, 2178, 2162, 466, 1140, 138, 3861, 2688, 3711, 4005, 2467, 3579, 3936, 1117, 436 |
| PY4 | 201, 4136, 1400, 1862, 2836, 1669, 517, 2770, 4043, 3291, 3225, 3703, 2418, 2508, 2663, 2378, 2302, 1418, 2603, 3013, 1153, 2606, 2627, 4067, 1864, 264, 3009, 4060, 2014, 2236, 520, 961, 1444, 1657, 3625, 4011, 727, 588, 3371, 19, 1387, 3702, 3790, 2897, 2787, 3831, 3327, 2326, 3767, 1859, 1896, 1764, 3786, 3729, 659, 3262, 1571, 508, 3180, 1564, 3501, 6, 3574, 2607, 1235, 589, 996, 913, 1390, 127, 1437, 3437, 1717, 3474, 3937, 748, 3270, 2619, 490, 2154, 2904, 3029, 2884, 1568, 4093, 218, 1007, 1639, 3206, 849, 3467, 4072, 912, 1344, 252, 2334, 3244, 1497, 366, 1894, 4170, 3546, 920, 2734, 3260, 4089, 3003, 1935, 3162, 719, 1976, 374, 1283, 3649, 1637, 330, 4003, 628, 1805, 2277, 2049, 2612, 3743, 1071, 1251, 755, 1045, 1860, 1827, 1555, 1175, 3115, 815, 3197, 12, 675, 1781, 2698, 1732, 1082, 4113, 1294, 1200, 3753, 3592, 81, 333, 379, 1954, 3342, 1594, 836, 653, 2091, 3602, 3632, 3426, 650, 2777, 1834, 1821, 70, 2771, 1925, 1376, 3506, 2479, 2769, 2082, 1521, 3299, 189, 3109, 1457, 2022, 2408, 3968, 1909, 2776, 1543, 1590, 227, 92, 1920, 798, 939, 190, 1643, 726, 1103, 971, 810, 1559, 1017, 2975, 1212, 2075, 2928, 8, 394, 4046, 510, 3391, 3100, 465, 224, 1439, 472, 680, 2804, 2544, 4080, 181, 1650, 512, 1945, 2506, 1395, 591, 754, 3168, 660, 1557, 2581, 3756, 1483, 1357, 2622, 940, 204, 3221, 3132, 2692, 3865, 373, 256, 1182, 1393, 485, 603, 2217, 2452, 3689, 2490, 2543, 2370, 497, 2309, 2866, 1551, 586, 1762, 1742, 26, 360, 541 |
| PY5 | 1089, 1765, 1975, 161, 2036, 2056, 2494, 3433, 4048, 2938, 1621, 232, 1721, 1055, 3883, 1343, 3659, 2387, 787, 1150, 2794, 887, 3977, 177, 3083, 4157, 421, 2520, 2868, 2747, 397, 2083, 670, 2395, 3572, 4020, 2345, 767, 2077, 2551, 1600, 1096, 1157, 1782, 2274, 1070, 121, 976, 102, 3456, 444, 2273, 2180, 2845, 1715, 3619, 814, 1160, 703, 1987, 1699, 176, 3595, 3988, 3593, 2002, 106, 369, 112, 1744, 1180, 997, 1622, 4059, 2697, 3136, 3475, 528, 3378, 1178, 1164, 2999, 1028, 1774, 4168, 332, 1426, 2923, 117, 211, 3461, 4177, 2941, 2522, 294, 1371, 663, 2977, 3113, 1130, 3464, 2199, 3080, 2889, 247, 3186, 1787, 1255, 439, 3615, 4051, 2708, 3578, 2183, 785, 759, 2130, 1438, 897, 1539, 1989, 308, 987, 2816, 1169, 2153, 2400, 71, 2720, 3975, 3531, 1698, 518, 2222, 506, 2679, 266, 1854, 1355, 2096, 34, 479, 3929, 2778, 192, 3457, 2893, 868, 1525, 731, 4179, 761, 2269, 3084, 646, 2072, 3961, 2145, 3033, 187, 3577, 4075, 3639, 1133, 825, 418, 3922, 3684, 1829, 2519, 3859, 3582, 749, 778, 2873, 1998, 2673, 1120, 209, 3182, 3638, 1633, 3536, 3744, 147, 39, 1136, 293, 2035, 1509, 2572, 2963, 845, 3813, 1887, 3850, 3692, 3006, 2101, 3383, 375, 2602, 1880, 723, 503, 1065, 3305, 3077, 1107, 111, 736, 504, 2899, 1398, 1580, 3408, 2718, 974, 386, 2818, 3534, 1901, 3444, 2207, 3343, 251, 1812, 3117, 3606, 2256, 1031, 4156, 3311, 972, 909, 1297, 1312, 3396, 2959, 942, 3640, 3517, 4045, 1964, 1159, 2837, 78, 1613, 1123, 1218, 3491, 163, 272, 2885, 1156, 2750 |

TABLE 2-continued

Mixing Pool and Corresponding Clone Numbers contained therein

| | |
|---|---|
| PY6 | 2593, 2126, 1336, 295, 385, 250, 740, 3116, 1452, 2728, 561, 2341, 3822, 3569, 2157, 2691, 3049, 4015, 1759, 1694, 3539, 686, 3931, 2037, 2382, 1703, 1226, 2388, 3967, 3399, 2951, 2290, 560, 2852, 3397, 1167, 2260, 2789, 522, 3018, 407, 3269, 1672, 3196, 2401, 3887, 738, 1485, 1991, 2251, 958, 1236, 1933, 1173, 1337, 3664, 936, 1668, 1056, 146, 3328, 1856, 2409, 3284, 3647, 3067, 469, 1467, 299, 1674, 2890, 1487, 3694, 3390, 1363, 128, 402, 2943, 4120, 743, 3941, 1685, 2920, 2031, 4158, 4098, 2724, 3158, 1959, 3589, 3950, 1080, 2143, 292, 3739, 155, 578, 2739, 1570, 3842, 1612, 219, 3552, 4029, 1247, 937, 881, 124, 1697, 4066, 1946, 3774, 49, 38, 2869, 3490, 2389, 221, 2067, 1486, 923, 3376, 2752, 3346, 777, 2815, 717, 118, 1315, 2962, 169, 784, 4024, 886, 830, 876, 101, 2238, 642, 171, 1433, 3548, 3123, 2374, 2442, 3345, 2367, 238, 1839, 3494, 371, 2908, 1261, 3749, 3099, 2433, 2865, 1338, 173, 618, 463, 1450, 1391, 1830, 2693, 1890, 3796, 276, 1767, 2655, 2783, 327, 3002, 2833, 1193, 1857, 3873, 1607, 2346, 3908, 2505, 1866, 1549, 2617, 1076, 2322, 2906, 734, 1506, 3187, 1629, 2674, 3047, 639, 1729, 3762, 2716, 1595, 3128, 3624, 3156, 2351, 4118, 417, 1097, 2912, 2667, 2905, 2172, 1879, 2347, 626, 791, 3851, 1895, 3177, 1479, 1286, 1013, 960, 4147, 3740, 1712, 1598, 351, 3993, 3745, 2966, 1023, 2368, 3439, 1224, 3852, 3889, 3511, 2857, 988, 3758, 3375, 3249, 1554, 2468, 3367, 3160, 3482, 2381, 4078, 1992, 2591, 1015, 2041, 2187, 3542, 1149, 2478, 3646 |
| PY7 | 2740, 564, 1394, 547, 3332, 682, 614, 1501, 3004, 2420, 2657, 3386, 3500, 3462, 216, 2785, 1868, 1952, 2922, 2427, 2234, 2262, 2955, 2100, 1770, 1808, 2441, 467, 3683, 3486, 2649, 855, 1944, 2202, 3202, 303, 3618, 2564, 1963, 2425, 57, 896, 981, 917, 2259, 629, 3169, 2390, 931, 1962, 416, 715, 245, 969, 1034, 915, 4068, 393, 867, 957, 2109, 1885, 234, 2119, 2846, 4097, 2548, 3654, 194, 20, 4116, 2280, 2763, 2642, 2946, 140, 1841, 406, 934, 2550, 2185, 2665, 1931, 1714, 781, 152, 449, 2568, 1540, 2705, 580, 3535, 3071, 3231, 782, 2376, 1443, 77, 2474, 3250, 1240, 1328, 175, 3637, 2121, 2926, 1736, 2974, 1695, 2120, 2880, 2894, 3580, 1561, 1307, 3289, 2527, 2044, 1883, 237, 4013, 2402, 1999, 2282, 18, 1691, 1686, 1053, 1296, 3807, 2051, 543, 689, 55, 1249, 2746, 964, 3983, 1496, 2342, 1826, 535, 3040, 3264, 2243, 2793, 1951, 616, 2731, 1237, 2156, 3354, 2978, 2620, 590, 447, 3509, 1707, 1154, 953, 3653, 2094, 1110, 577, 1346, 4119, 1636, 979, 601, 2301, 2279, 37, 1473, 2315, 2422, 2317, 429, 705, 1098, 2903, 2960, 2570, 4103, 2146, 2438, 882, 2139, 676, 1845, 1938, 3794, 2632, 16, 3340, 1528, 3725, 1971, 1292, 268, 3381, 1341, 3286, 2582, 2872, 1196, 1625, 341, 470, 2231, 172, 2858, 3701, 757, 1111, 3877, 1601, 3498, 380, 3166, 2881, 3826, 2429, 153, 2227, 1488, 3183, 3526, 1118, 0, 2615, 3478, 1644, 2532, 1041, 721, 422, 807, 2089, 1367, 2953, 399, 2052, 1081, 3448, 3969, 2722, 4123, 3251, 4069, 1858, 1690, 185, 2142, 907, 1724, 3998 |
| PY8 | 608, 1223, 1511, 3863, 2336, 992, 1907, 291, 2065, 3296, 297, 4079, 1413, 445, 401, 3222, 2658, 2733, 3227, 301, 1979, 53, 2323, 2973, 1986, 425, 3466, 1161, 240, 3208, 1168, 2678, 3510, 2106, 1440, 2318, 550, 3742, 1831, 3556, 1706, 2475, 1231, 1018, 1319, 932, 1659, 2925, 3147, 3947, 3943, 1800, 1515, 2887, 1470, 753, 2909, 355, 1407, 3138, 2597, 3846, 342, 2195, 3676, 1619, 2820, 2283, 3335, 2696, 3920, 3314, 802, 938, 4111, 1530, 4152, 1676, 493, 3840, 2567, 884, 3915, 96, 116, 3728, 3598, 1454, 2531, 604, 389, 3879, 331, 1414, 3609, 1088, 1757, 105, 3440, 1665, 4135, 3351, 3300, 3016, 1980, 2621, 3394, 843, 1040, 2541, 2379, 1912, 249, 3078, 3614, 1266, 3985, 2473, 325, 2097, 1852, 1769, 3963, 3392, 235, 501, 3353, 104, 1797, 3617, 1828, 2669, 2706, 655, 2193, 3395, 2529, 409, 212, 2762, 1936, 1020, 1228, 2171, 702, 2931, 544, 1074, 4004, 4138, 1183, 2726, 1610, 2321, 2876, 4038, 352, 729, 2278, 856, 1139, 3190, 885, 2571, 3480, 427, 1058, 3114, 2057, 3833, 3726, 3064, 1281, 902, 202, 634, 662, 2410, 1642, 890, 2445, 3095, 1775, 1692, 4164, 3023, 1406, 3763, 344, 1929, 1851, 2989, 3200, 254, 2528, 1847, 2170, 622, 4022, 2562, 2412, 1947, 2641, 2546, 1771, 795, 692, 3061, 1001, 40, 3525, 1431, 3412, 2796, 3768, 3170, 1102, 337, 1615, 3633, 699, 2220, 376, 2805, 852, 2118, 2879, 1545, 2501, 1121, 2123, 288, 3773, 683, 1420, 2470, 2208, 3797, 770, 3364, 1783, 3545, 3453, 1837, 1239, 2406, 2743, 3828, 2709, 3089, 1242, 1524, 3781, 1534, 3583, 3634 |
| PY9 | 255, 1704, 2428, 3990, 524, 2650, 1626, 3693, 2735, 1184, 3808, 654, 3996, 2578, 423, 2261, 1974, 3667, 2038, 2064, 3733, 2810, 1201, 2565, 2469, 3066, 1374, 7, 3312, 956, 1126, 1492, 1372, 32, 1185, 862, 3052, 1, 298, 2200, 799, 2361, 2952, 287, 2775, 2538, 2048, 1795, 1997, 1187, 2359, 4095, 3268, 2483, 3228, 1820, 1179, 215, 2677, 3056, 768, 833, 716, 1270, 317, 395, 259, 4139, 1961, 1419, 3074, 3479, 3290, 3812, 4092, 2590, 3677, 732, 677, 133, 226, 968, 2437, 1314, 90, 1734, 595, 1176, 3050, 1948, 2609, 789, 3012, 2190, 2149, 3503, 3210, 3471, 3218, 2440, 1451, 3944, 2450, 2934, 482, 3000, 2275, 2919, 347, 794, 1696, 3824, 1271, 3629, 879, 3384, 2499, 4007, 3455, 3723, 2030, 279, 1189, 1811, 3529, 3715, 4018, 1475, 2296, 282, 2366, 3504, 1579, 233, 2577, 2729, 3476, 229, 453, 2717, 1817, 1119, 2492, 2246, 142, 476, 3037, 3522, 1653, 2327, 459, 1924, 1284, 1373, 2715, 1529, 3065, 2343, 362, 1752, 2237, 3926, 2713, 2255, 1789, 3415, 392, 1222, 170, 2226, 2758, 878, 643, 2176, 1455, 3770, 2110, 3971, 3787, 2285, 3330, 2987, 2997, 1731, 3613, 3621, 805, 2286, 2466, 2373, 1425, 4155, 1843, 1658, 304, 3864, 2554, 2536, 2534, 1984, 3604, 434, 3165, 788, 3849, 1965, 1000, 2026, 1728, 1512, 454, 2386, 2294, 4037, 1368, 623, 2549, 206, 548, 762, 1364, 2241, 328, 1404, 1047, 2175, 531, 1673, 3281, 2694, 3434, 2654, 1815, 2417, 3843, 4159, 775, 1129, 1677, 3635, 4142, 829, 652, 930, 1069, 3780, 500, 433, 2547, 3263, 1138, 278, 1825, 52, 3914, 2313 |
| PY10 | 122, 3144, 1566, 3129, 854, 983, 3925, 1423, 1638, 3185, 79, 3121, 2587, 2629, 1718, 1498, 356, 911, 990, 2127, 1424, 1809, 1202, 866, 2040, 3039, 3815, 800, |

TABLE 2-continued

Mixing Pool and Corresponding Clone Numbers contained therein

|      |      |
| ---- | ---- |
|      | 1546, 950, 1505, 4121, 2711, 2284, 1743, 492, 413, 3516, 706, 2867, 1552, 539, 488, 4143, 420, 858, 3451, 1012, 159, 2526, 1358, 3911, 1131, 2961, 3710, 3720, 2914, 391, 1688, 3707, 3191, 4126, 484, 1322, 2699, 2270, 1101, 4117, 4172, 1597, 3862, 1063, 2573, 377, 1329, 4129, 199, 1434, 3302, 3242, 651, 1370, 316, 3939, 193, 3401, 455, 3036, 2265, 145, 1188, 3358, 2465, 2263, 1526, 1723, 3788, 1683, 2839, 4014, 584, 3626, 69, 2299, 1977, 149, 863, 2842, 4031, 1970, 400, 3935, 3713, 2307, 2768, 2927, 1725, 4006, 1574, 1647, 2714, 1941, 860, 2970, 3068, 1396, 3512, 4112, 1014, 3783, 1710, 3691, 779, 3234, 43, 711, 944, 1934, 2431, 2055, 3370, 739, 2624, 1345, 2644, 2937, 59, 2601, 3443, 3178, 955, 3215, 3240, 1412, 2272, 2331, 846, 1576, 3603, 257, 2411, 1478, 3596, 3470, 1309, 3445, 260, 946, 908, 1217, 107, 2292, 1560, 135, 666, 1670, 906, 3024, 2849, 615, 2681, 72, 3655, 4085, 3855, 1816, 1143, 2888, 3271, 1030, 3605, 3553, 2749, 1810, 2164, 975, 3054, 3359, 4035, 435, 2046, 2344, 3672, 4101, 3658, 370, 4053, 2940, 2042, 3907, 1268, 1661, 4169, 3436, 2825, 2660, 1784, 1170, 2045, 1465, 2008, 1558, 1411, 242, 1666, 2635, 3751, 1919, 2140, 598, 3555, 1537, 3835, 2069, 527, 3869, 191, 3984, 2330, 2446, 3568, 2356, 822, 3005, 3719, 2950, 1383, 1708, 3402, 143, 1350, 478, 2189, 2686, 2727, 3949 |
| PY11 | 1362, 869, 1468, 3266, 2095, 2293, 2957, 999, 1632, 2710, 877, 2860, 4047, 3888, 3584, 2240, 286, 3558, 1298, 1908, 1519, 611, 1108, 1886, 156, 3991, 440, 1114, 1915, 3195, 2496, 1705, 2152, 2355, 2424, 166, 1092, 747, 2223, 2623, 3718, 1190, 3458, 3154, 2398, 2099, 1604, 2984, 2895, 965, 1282, 3159, 572, 1599, 3097, 134, 2766, 850, 2136, 4057, 3999, 2098, 2784, 4041, 1472, 3307, 3708, 4083, 1865, 3404, 1073, 658, 2936, 2491, 3858, 3051, 3747, 3021, 3755, 2850, 2365, 3537, 3181, 2432, 443, 4125, 1881, 3245, 14, 487, 3845, 3272, 1751, 2476, 511, 696, 3236, 633, 515, 1891, 792, 3706, 2493, 1747, 635, 688, 1460, 1127, 2407, 168, 2181, 834, 638, 1939, 3538, 2011, 123, 2298, 894, 2264, 2900, 2798, 3192, 2990, 2463, 1651, 2472, 1785, 3964, 74, 2404, 2434, 3420, 2736, 3017, 2598, 3938, 412, 2765, 4105, 1399, 261, 1115, 3806, 98, 3668, 2545, 4021, 1535, 3304, 2864, 3126, 2297, 3315, 888, 533, 2668, 4002, 3220, 1458, 2054, 66, 3145, 3258, 924, 3229, 1325, 4094, 483, 3473, 1305, 3581, 2289, 2808, 486, 1773, 565, 1956, 3607, 1618, 285, 3690, 231, 4065, 2823, 978, 1499, 4081, 1109, 1592, 3, 1205, 3594, 1022, 496, 1252, 2141, 3567, 1086, 3010, 2348, 2254, 1940, 3277, 357, 323, 4, 2399, 2415, 27, 2976, 1353, 2500, 695, 1627, 2968, 993, 1903, 1148, 1648, 3608, 3261, 1679, 809, 2861, 473, 2569, 1036, 154, 901, 461, 23, 151, 494, 2218, 2462, 2449, 246, 3514, 1608, 2998, 624, 2911, 1671, 3804, 2828, 1953, 441, 120, 3557, 2416, 1567, 3441, 1215, 4166, 2892 |
| PY12 | 3661, 2080, 367, 1199, 4008, 574, 2653, 99, 3989, 2812, 3306, 3801, 2588, 3735, 1369, 2507, 3810, 3224, 1146, 65, 1259, 1928, 2878, 3982, 1436, 3497, 329, 2316, 481, 280, 58, 263, 3656, 95, 2353, 2239, 2102, 1044, 2063, 3792, 2579, 585, 2676, 361, 2634, 2871, 2921, 313, 3904, 3816, 2738, 3678, 3188, 568, 4062, 2851, 4127, 3209, 3267, 1264, 513, 358, 1321, 450, 951, 2748, 2656, 632, 1132, 3825, 2000, 3031, 62, 1441, 3118, 2020, 3057, 312, 3811, 3110, 1593, 305, 1392, 2324, 2122, 2025, 2859, 2633, 1427, 405, 2291, 2608, 2111, 1285, 2755, 2188, 1786, 1897, 4012, 3560, 220, 4073, 553, 2377, 2751, 3662, 2972, 3570, 498, 2721, 3255, 1245, 144, 2600, 4163, 2248, 2737, 318, 1416, 735, 3246, 1094, 2991, 1875, 2397, 1838, 2732, 644, 1624, 1605, 3361, 857, 921, 2325, 1960, 1340, 3724, 994, 130, 1806, 1606, 1609, 4055, 3308, 3643, 2253, 2486, 1032, 2068, 3454, 1873, 3063, 228, 3954, 1177, 545, 3665, 3785, 2362, 3022, 2683, 1046, 773, 3423, 1320, 2391, 180, 2599, 457, 2640, 1207, 310, 900, 2113, 963, 2090, 2132, 4165, 60, 2874, 1588, 1302, 1448, 1544, 725, 3086, 3764, 4028, 3962, 3818, 1900, 2489, 2495, 4141, 2131, 1572, 2333, 3442, 2229, 2423, 1582, 1513, 2010, 1463, 4114, 3698, 1994, 3682, 3293, 2560, 495, 1181, 3700, 2116, 2460, 3406, 3507, 4001, 3523, 3660, 3895, 842, 1274, 3520, 2916, 2824, 765, 3362, 3435, 460, 3657, 2482, 446, 87, 3133, 1462, 3323, 875, 1375, 489, 1093, 1091, 3681, 3347, 2647, 1730, 1922, 4145, 2944, 2782, 499, 3946, 3671, 2167, 85, 1848 |
| PY13 | 44, 1476, 2907, 1973, 1904, 3870, 1942, 1166, 1803, 1630, 4000, 3524, 3945, 3795, 3610, 582, 2086, 808, 763, 3205, 1926, 1137, 1474, 3278, 1969, 1654, 198, 1243, 3365, 1306, 3044, 1079, 509, 3239, 2104, 3679, 2435, 1768, 1995, 3153, 823, 3418, 2364, 1687, 1335, 3837, 1229, 2819, 3035, 1923, 691, 4106, 1273, 2811, 1949, 1702, 1386, 534, 3995, 431, 4134, 1641, 3748, 2337, 3760, 2266, 1874, 2821, 258, 2896, 2158, 801, 4144, 2245, 989, 2901, 532, 1422, 1289, 579, 2913, 3880, 2360, 3712, 2512, 4131, 48, 3338, 1333, 2076, 3090, 3356, 1726, 1208, 1378, 2618, 2611, 372, 1453, 1913, 3997, 1257, 2197, 1219, 977, 2596, 3987, 3641, 3101, 2719, 3518, 1384, 3549, 919, 2163, 3871, 3551, 2664, 4162, 694, 2651, 3298, 3055, 1360, 1628, 1779, 4074, 1057, 1532, 2980, 783, 1990, 3562, 1077, 174, 3421, 3573, 698, 2883, 569, 4115, 1466, 2372, 3839, 1634, 3379, 1024, 998, 3301, 903, 1004, 905, 1514, 1090, 925, 2954, 2047, 1216, 2105, 2616, 1446, 2979, 2779, 1680, 336, 3477, 1066, 4056, 3001, 1332, 1746, 3575, 656, 3176, 3008, 2203, 612, 1253, 2985, 3014, 1617, 2958, 67, 1681, 1435, 3502, 1324, 2340, 1523, 2994, 2310, 1693, 2918, 3088, 2363, 3280, 505, 4025, 1025, 2124, 1709, 2252, 1754, 3352, 3847, 3413, 2, 1471, 3685, 1652, 2004, 2704, 2863, 3151, 1755, 2942, 2830, 2882, 1635, 597, 474, 2358, 1667, 2249, 3918, 2630, 2566, 2184, 899, 3493, 3674, 2198, 2461, 1039, 3832, 3854, 3900, 756, 1275, 4128, 701, 2754, 2802, 2542, 2935, 871, 2695, 3730, 3714, 892, 1701, 3398, 3214, 2764, 926, 3669 |
| PY14 | 2151, 3597, 3333, 774, 1172, 4171, 3866, 2745, 1209, 904, 4010, 2645, 546, 2350, 3285, 2834, 68, 3616, 217, 3438, 3876, 1889, 837, 3778, 1763, 583, 414, 2281, 1203, 2730, 2339, 3238, 617, 452, 3163, 4017, 2115, 2753, 3073, 1481, 516, 3916, 2556, 1051, 4130, 3465, 2947, 3349, 864, 3612, 3882, 1662, 3488, 3543, 3405, 137, |

TABLE 2-continued

Mixing Pool and Corresponding Clone Numbers contained therein

| | |
|---|---|
| | 1664, 1276, 2071, 669, 3256, 824, 3223, 3048, 1569, 3953, 129, 1722, 1716, 2690, 3034, 3934, 2910, 2595, 861, 125, 2831, 742, 2385, 607, 200, 3235, 4019, 2179, 678, 3429, 3334, 131, 3053, 2114, 3766, 619, 1682, 554, 4023, 1010, 1351, 4071, 1152, 3483, 164, 1620, 704, 2375, 3237, 649, 1591, 3709, 3093, 1493, 3952, 3292, 2135, 3611, 1911, 2295, 324, 1502, 1415, 267, 2448, 1008, 3686, 3419, 1262, 3432, 3642, 1739, 3020, 3958, 4082, 2625, 1500, 3697, 4178, 3652, 462, 2267, 605, 3322, 1246, 1503, 1562, 828, 758, 796, 2552, 2574, 3407, 4033, 265, 3838, 1738, 746, 3019, 2523, 2271, 2795, 970, 1972, 103, 3951, 1084, 91, 1573, 1347, 162, 1061, 3857, 2335, 3204, 2455, 448, 3913, 132, 115, 2853, 388, 3736, 1112, 3149, 1162, 1863, 2930, 2703, 1538, 1171, 3295, 817, 1871, 898, 3722, 2349, 97, 3152, 3731, 2965, 2304, 1788, 2017, 3041, 1125, 1807, 1095, 737, 3072, 222, 3933, 2790, 916, 3075, 1776, 1930, 2107, 214, 2204, 3841, 3496, 3628, 621, 3139, 1798, 1227, 1835, 2835, 4086, 3427, 1244, 3746, 766, 3199, 502, 710, 2586, 1009, 2684, 3247, 2024, 3028, 3416, 2125, 606, 1417, 2584, 648, 1124, 3184, 2308, 2701, 751, 1790, 1861, 3011, 4042, 872, 2870 |
| PY15 | 1225, 1191, 3294, 2073, 378, 2652, 1950, 1663, 3894, 1278, 2314, 3431, 2015, 41, 244, 2066, 3400, 3389, 2481, 2848, 1049, 4137, 42, 424, 733, 186, 3076, 2480, 3776, 575, 2986, 2685, 3104, 819, 426, 3157, 3046, 419, 684, 2759, 1263, 3878, 991, 2813, 3481, 2001, 76, 2829, 1516, 1405, 674, 2225, 2756, 1349, 4174, 3414, 207, 685, 2357, 707, 3891, 343, 1026, 838, 3980, 3179, 1006, 3103, 697, 2981, 3986, 1720, 1304, 2211, 3836, 25, 1330, 2856, 555, 3331, 320, 2509, 640, 1589, 314, 2540, 15, 468, 673, 284, 1646, 2206, 3380, 119, 3587, 1042, 2477, 3219, 2443, 1616, 687, 1484, 1623, 2161, 3979, 3590, 3798, 771, 3282, 2513, 712, 2982, 2444, 2558, 690, 3372, 3527, 4122, 1099, 3252, 2019, 3450, 2380, 3976, 816, 3344, 3043, 941, 3106, 213, 3576, 1232, 1064, 1804, 2518, 2809, 3326, 558, 2580, 1937, 1824, 1401, 1993, 2799, 1385, 1684, 364, 2392, 918, 2169, 613, 1254, 387, 2088, 2018, 3981, 1388, 4104, 3695, 566, 438, 2924, 197, 363, 3216, 1905, 195, 3820, 2761, 3912, 63, 1445, 47, 3276, 3318, 1578, 910, 165, 1301, 3960, 2781, 3430, 1978, 962, 157, 1832, 3585, 3265, 51, 1888, 2338, 3428, 239, 982, 3254, 3800, 4124, 832, 3860, 2643, 3564, 3257, 1849, 2250, 50, 914, 3906, 538, 64, 2320, 4151, 1380, 581, 1583, 1884, 2806, 3734, 3460, 3793, 1241, 2992, 3600, 2945, 2405, 3599, 3164, 1050, 10, 203, 4063, 1494, 1122, 3422, 61, 2862, 3468, 3591, 1957, 3917, 804, 382, 3105, 3716, 3814, 562, 3875, 2012, 851, 1313, 567, 4091, 2303, 2614, 3403, 3253, 1085 |
| PZ0 | 1225, 2151, 44, 3661, 1362, 122, 255, 608, 2740, 2593, 1089, 201, 3130, 1059, 2155, 1577, 3616, 808, 3224, 3558, 911, 3667, 2733, 1952, 4015, 2387, 1418, 3127, 3782, 587, 2774, 3389, 2104, 2353, 2424, 1743, 1185, 1440, 3202, 3397, 3572, 3625, 354, 1876, 2485, 954, 426, 3163, 3678, 3159, 3911, 4095, 1800, 715, 1236, 2273, 1764, 178, 594, 3373, 1021, 2225, 1662, 4106, 1865, 4172, 1961, 3335, 194, 299, 112, 1390, 3769, 883, 1287, 1432, 697, 1716, 258, 1132, 3401, 1734, 3728, 152, 4098, 332, 218, 927, 306, 2117, 893, 2540, 3429, 4131, 2025, 4125, 2450, 3300, 175, 3552, 3080, 920, 2537, 1258, 3203, 4102, 1623, 704, 2197, 553, 2493, 69, 2097, 237, 1486, 1539, 2277, 2186, 3102, 2594, 2995, 3252, 267, 694, 735, 2264, 1647, 3723, 964, 101, 266, 1781, 410, 1735, 93, 2504, 3326, 462, 3573, 3724, 3938, 944, 3476, 2529, 3749, 3084, 2091, 700, 1316, 2877, 3025, 2088, 746, 1090, 3954, 3315, 1412, 1373, 2321, 2620, 3859, 3299, 1397, 1361, 1631, 3131, 63, 3204, 1746, 1207, 1305, 107, 2758, 3726, 2279, 2783, 1643, 2671, 2917, 596, 2712, 3265, 3295, 2340, 4028, 4081, 2888, 2286, 3763, 676, 734, 293, 3499, 3279, 2414, 895, 50, 737, 3847, 4114, 357, 3658, 3849, 1771, 1196, 1097, 503, 465, 4064, 2288, 1584, 3600, 1798, 2358, 842, 3261, 1558, 2241, 2220, 2429, 3740, 1901, 660, 4153, 311, 2646, 3917, 3028, 1275, 1375, 3514, 2330, 1677, 770, 1367, 3375, 2959, 485, 322, 4027, 3091, 1085, 2870, 3669, 1848, 2892, 3949, 2313, 3634, 3998, 3646, 2750, 541, 436, 3329, 1981 |
| PZ1 | 1191, 3597, 1476, 2080, 869, 3144, 1704, 1223, 564, 2126, 1765, 4136, 1520, 1382, 1442, 514, 217, 763, 1146, 1298, 990, 2038, 3227, 2922, 1759, 787, 2603, 3771, 3627, 4044, 1741, 2481, 3679, 2239, 166, 492, 862, 2318, 303, 1167, 4020, 4011, 2983, 432, 3141, 1269, 3157, 4017, 3188, 572, 1131, 3268, 1515, 245, 1933, 2180, 3786, 1958, 2354, 167, 283, 2756, 3488, 1273, 3404, 1597, 1419, 2696, 20, 1674, 1744, 127, 2192, 708, 2687, 1893, 2981, 2690, 2896, 3825, 455, 595, 3598, 449, 2724, 1426, 1007, 1165, 625, 1813, 2006, 15, 3334, 48, 2859, 1881, 2934, 3016, 3637, 4029, 2889, 2734, 2311, 2150, 2458, 3670, 2161, 2375, 1219, 2377, 1747, 2299, 1852, 4013, 923, 1989, 2049, 2648, 1563, 1359, 1870, 2019, 2448, 2651, 3246, 2900, 2714, 2030, 3983, 2238, 1854, 2698, 1389, 384, 2196, 1517, 558, 2267, 698, 994, 412, 1934, 229, 409, 3099, 646, 3602, 1195, 874, 2800, 1867, 2018, 3019, 925, 1177, 888, 2272, 2715, 2876, 590, 3582, 189, 2219, 3848, 2459, 2377, 1445, 2455, 3575, 310, 3581, 2292, 878, 3064, 37, 327, 726, 9, 1029, 3198, 2215, 51, 817, 1523, 3962, 1109, 3271, 2466, 344, 1845, 1506, 2035, 1238, 3108, 136, 4050, 914, 3072, 3413, 3698, 323, 370, 1965, 795, 1625, 2912, 1065, 224, 631, 1142, 28, 2945, 1227, 1667, 1274, 1679, 1411, 328, 376, 153, 1712, 3444, 1557, 1542, 3663, 2032, 804, 3416, 4128, 489, 1608, 2446, 3635, 3364, 2953, 3249, 942, 603, 2173, 2792, 4049, 382, 2125, 701, 1093, 2998, 3568, 4142, 1783, 399, 1554, 3640, 2217, 2757, 2847, 1428 |
| PZ2 | 3294, 3333, 2907, 367, 1468, 1566, 2428, 1511, 1394, 1336, 1975, 1400, 1853, 2471, 302, 2659, 3438, 3205, 65, 1908, 2127, 2064, 301, 2427, 1694, 1150, 3013, 273, 1221, 1527, 2662, 2848, 2435, 2102, 1092, 413, 3052, 550, 3618, 2260, 2345, 727, 724, 967, 230, 1575, 3046, 2115, 568, 1599, 2961, 2483, 2887, 969, 1173, 2845, 3729, 1761, 2210, 141, 2085, 1349, 3543, 2811, 1073, 3862, 3074, 3920, 4116, 2890, 1180, 1437, 1078, 1510, 396, 2592, 3986, 3034, 2158, 2000, 3036, |

TABLE 2-continued

Mixing Pool and Corresponding Clone Numbers contained therein

|     |     |
| --- | --- |
|     | 1176, 1454, 2568, 3158, 2923, 1639, 3830, 811, 2103, 2488, 468, 131, 3338, 2633, 3245, 482, 1980, 2121, 1247, 247, 3260, 269, 253, 713, 1477, 3979, 3237, 977, 2751, 635, 1977, 1769, 2402, 3376, 308, 2612, 730, 150, 1116, 1614, 3450, 1008, 3298, 1094, 2798, 1941, 279, 1496, 642, 1355, 1732, 3449, 471, 793, 1135, 2580, 605, 2883, 130, 2765, 2431, 453, 212, 2433, 2072, 3632, 3540, 521, 557, 2137, 3981, 2523, 2954, 545, 533, 2331, 1529, 4038, 447, 749, 3109, 430, 1536, 3485, 3325, 47, 448, 656, 900, 2289, 1560, 643, 1281, 1473, 3002, 1103, 335, 880, 2801, 3492, 1888, 1871, 2994, 3818, 1592, 1030, 2373, 1929, 1938, 3187, 1509, 1456, 1379, 1134, 3588, 3906, 222, 2, 1994, 4, 4053, 1000, 692, 341, 2667, 3305, 1439, 3761, 2996, 1508, 2405, 1835, 2249, 3520, 809, 242, 1404, 2805, 2227, 1598, 2207, 2581, 1921, 1054, 1068, 3599, 2835, 3918, 2916, 2861, 1666, 1047, 852, 1488, 351, 3343, 3756, 321, 3487, 236, 3105, 606, 2754, 1091, 624, 2356, 829, 3545, 2052, 2468, 3517, 2452, 3042, 3903, 973 |
| PZ3 | 2073, 774, 1973, 1199, 3266, 3129, 3990, 3863, 547, 295, 161, 1862, 2148, 3809, 3079, 1310, 3876, 1926, 1259, 1519, 1424, 3733, 1979, 2234, 3539, 2794, 1153, 593, 1002, 1504, 563, 1049, 1768, 1044, 747, 3516, 1, 3742, 2564, 2789, 767, 588, 2854, 3519, 3765, 1640, 419, 2753, 4062, 3097, 3710, 3228, 1470, 1034, 1337, 1715, 659, 1916, 4058, 3175, 390, 4174, 3405, 1949, 658, 1063, 3479, 3314, 2280, 1487, 997, 3437, 1339, 2539, 1048, 3620, 1720, 3934, 801, 3031, 2265, 3050, 2531, 1540, 1959, 117, 3206, 3137, 1968, 2964, 3155, 673, 3053, 1333, 1427, 14, 3000, 2621, 2926, 937, 3186, 4089, 3528, 3148, 1596, 4100, 3590, 649, 2596, 3662, 688, 149, 3963, 1999, 2752, 987, 3743, 2232, 158, 275, 980, 2380, 3686, 3055, 2991, 3192, 860, 1189, 2342, 171, 2096, 1082, 647, 1758, 3550, 33, 1937, 3322, 569, 1806, 4105, 2055, 2717, 2762, 2865, 3961, 3426, 2666, 1265, 1327, 507, 1388, 2271, 2047, 3665, 2668, 846, 3065, 352, 3509, 778, 1457, 3955, 4146, 2767, 1409, 3276, 3913, 3176, 2113, 2808, 135, 2176, 902, 2315, 2833, 971, 1823, 1194, 2932, 22, 2338, 898, 2310, 1900, 3, 3605, 1425, 1851, 3794, 1629, 2572, 371, 1719, 248, 2814, 538, 3933, 1471, 3682, 2399, 2940, 2026, 3061, 470, 2905, 3077, 472, 3777, 2276, 620, 64, 2790, 3685, 3293, 2415, 2042, 1728, 1001, 2231, 2172, 1107, 680, 82, 3243, 813, 3164, 4086, 2630, 2824, 473, 2635, 2175, 2118, 3183, 3993, 251, 1483, 728, 1791, 2817, 3716, 1417, 2802, 3681, 2911, 822, 652, 3453, 1081, 3367, 4045, 3689, 2178, 1206, 3696 |
| PZ4 | 378, 1172, 1904, 4008, 2095, 854, 524, 2336, 3332, 385, 2036, 2836, 3513, 2221, 1750, 2576, 1889, 1137, 1928, 611, 1809, 2810, 53, 2262, 686, 887, 2606, 2803, 2741, 2464, 46, 4137, 1995, 2063, 2223, 706, 298, 1831, 1963, 522, 2077, 3371, 3230, 315, 4173, 3521, 684, 3073, 2851, 134, 3720, 1820, 753, 915, 3664, 3619, 3262, 3189, 35, 2112, 2689, 3414, 137, 1702, 2936, 2573, 3290, 802, 2763, 3694, 1622, 1717, 80, 4133, 3248, 3565, 1304, 2910, 4144, 62, 145, 1948, 604, 2705, 3589, 211, 849, 1019, 1556, 2058, 1491, 284, 2114, 2076, 405, 487, 2275, 3394, 1736, 881, 1787, 3003, 1303, 1291, 2682, 3310, 3798, 1591, 3987, 2972, 1460, 863, 3392, 2282, 3346, 2816, 1071, 592, 2902, 3058, 4077, 3976, 3419, 1360, 1875, 2990, 2970, 1811, 1826, 1433, 34, 4113, 2956, 2235, 1147, 1489, 1824, 1246, 4115, 1606, 1399, 3370, 1817, 1936, 1338, 2145, 650, 1250, 1794, 3463, 1105, 4104, 2795, 1216, 3785, 4002, 1576, 2343, 729, 1707, 2873, 2022, 3062, 110, 1403, 3382, 3318, 132, 3008, 963, 486, 666, 1455, 202, 2422, 1193, 810, 205, 720, 4108, 1586, 3428, 3722, 1693, 2489, 1205, 3553, 4155, 2989, 2632, 2674, 2963, 1766, 4016, 2744, 1745, 239, 2349, 2918, 2495, 3594, 2749, 1843, 3200, 16, 3047, 845, 1559, 665, 1300, 2214, 2320, 916, 1652, 2560, 27, 3907, 1512, 40, 172, 1879, 111, 2804, 1547, 641, 3350, 1050, 3427, 2566, 765, 2569, 3751, 531, 2879, 3526, 3745, 1812, 1357, 3896, 2159, 3355, 3814, 2584, 2542, 3347, 1671, 3005, 930, 1837, 3448, 3160, 1964, 2490, 2162, 1214, 4026 |
| PZ5 | 2652, 4171, 3870, 574, 2293, 983, 2650, 992, 682, 250, 2056, 1669, 3853, 3921, 3207, 549, 837, 1474, 2878, 1108, 1202, 1201, 2323, 2955, 3931, 3977, 2627, 2319, 3424, 3978, 812, 42, 3153, 3792, 2623, 2867, 2200, 3556, 2425, 3018, 2551, 19, 3194, 3324, 1192, 1035, 2759, 1481, 4127, 2766, 2914, 1179, 2909, 4068, 936, 814, 1571, 3784, 3974, 2070, 3087, 207, 1664, 1386, 2491, 377, 3812, 938, 2642, 3390, 4059, 3474, 326, 3772, 873, 2177, 2211, 2595, 2245, 1441, 1188, 2609, 389, 580, 3950, 3461, 3467, 1213, 442, 2772, 3571, 1646, 3766, 3090, 2291, 3845, 2919, 843, 2974, 124, 1255, 1935, 3119, 3631, 2287, 3973, 771, 3709, 3641, 3570, 1127, 2842, 235, 18, 777, 1169, 1251, 2626, 3059, 661, 985, 816, 1262, 1628, 2397, 2463, 3068, 3529, 535, 3548, 479, 1294, 714, 3737, 100, 368, 1401, 1503, 1466, 1609, 261, 739, 1119, 1020, 173, 3033, 2777, 2456, 609, 1966, 1144, 3695, 970, 2105, 2362, 3220, 3603, 362, 2278, 1154, 1998, 2408, 1793, 1801, 556, 3650, 1578, 115, 2203, 2090, 1773, 1670, 3770, 634, 2317, 1857, 3968, 2053, 630, 3232, 428, 910, 2853, 612, 2132, 565, 906, 2110, 662, 429, 3873, 2673, 1469, 4132, 1280, 346, 982, 97, 3088, 4141, 1022, 1810, 1658, 254, 3340, 639, 3813, 1017, 780, 2791, 1655, 4151, 3075, 2004, 495, 2976, 1268, 454, 3525, 2858, 2347, 736, 2544, 2503, 806, 3172, 10, 1244, 2184, 3362, 1036, 1919, 1673, 1545, 1118, 2966, 3117, 2622, 870, 1840, 334, 562, 648, 2935, 2647, 3804, 3719, 1069, 1239, 3969, 3482, 1159, 2543, 466, 2840, 2533 |
| PZ6 | 1950, 3866, 1942, 2653, 2957, 3925, 1626, 1907, 614, 740, 2494, 517, 381, 348, 1354, 3275, 3778, 3278, 3982, 1886, 866, 2565, 2973, 2100, 2037, 177, 4067, 2147, 3544, 3673, 3388, 424, 823, 2579, 3718, 1552, 799, 1706, 57, 407, 1600, 1387, 2027, 183, 3819, 2524, 1263, 516, 3209, 850, 391, 215, 355, 393, 1668, 1160, 508, 451, 3085, 2517, 790, 685, 1276, 534, 3858, 1329, 4092, 4111, 2946, 1363, 2697, 3937, 4149, 1033, 4009, 2212, 3836, 861, 989, 3118, 3358, 789, 3879, 3535, 1080, 4177, 4072, 3901, 664, 86, 1279, 2206, 619, 3356, 2608, 3272, 347, 1040, 1695, 1697, 439, 3162, 2305, 477, 3666, 3948, 3282, 3093, 3101, 498, 2407, 4031, 501, |

TABLE 2-continued

| | Mixing Pool and Corresponding Clone Numbers contained therein |
|---|---|
| | 1691, 2815, 2153, 755, 2016, 2413, 2993, 148, 3344, 3432, 1779, 1838, 1651, 1396, 3715, 3040, 3123, 3929, 1200, 1833, 408, 2822, 3212, 1993, 1562, 2372, 4055, 1115, 2624, 2492, 1228, 618, 187, 1834, 4107, 3897, 1163, 2875, 566, 1972, 2616, 3022, 1458, 257, 1752, 856, 953, 3577, 1821, 2585, 2133, 262, 1421, 438, 103, 1446, 2683, 2054, 2411, 2237, 1139, 3653, 463, 1909, 480, 4032, 2742, 1932, 165, 388, 1253, 4165, 1956, 3024, 3971, 2410, 705, 1607, 1120, 3547, 2516, 3173, 2439, 3254, 3152, 2363, 2131, 496, 2164, 304, 2528, 1528, 1729, 1887, 2975, 3844, 3411, 2723, 1380, 1776, 2704, 1181, 1353, 1661, 2386, 1431, 3701, 626, 504, 4080, 1323, 403, 1507, 203, 3746, 899, 3435, 154, 2140, 3281, 2501, 0, 1023, 3606, 940, 3799, 2224, 2084, 3875, 1124, 871, 1730, 2828, 2950, 3780, 2406, 2722, 2381, 2837, 2370, 1140, 2780, 859 |
| PZ7 | 1663, 2745, 1166, 99, 999, 1423, 3693, 291, 1501, 3116, 3433, 2770, 1331, 2182, 2604, 1311, 1763, 1969, 1436, 156, 2040, 2469, 1986, 1770, 2382, 3083, 1864, 1011, 1072, 456, 3533, 733, 3418, 585, 1190, 539, 2361, 2475, 896, 3269, 1096, 3702, 1464, 2797, 296, 2967, 3878, 3916, 3267, 2136, 1688, 2677, 1407, 867, 1056, 703, 3180, 3288, 3885, 745, 1689, 2357, 2071, 3995, 3051, 4129, 2590, 1530, 140, 128, 3136, 748, 2639, 3469, 4076, 3930, 25, 125, 2901, 2020, 2465, 3012, 331, 3071, 2143, 2941, 912, 671, 3161, 289, 3122, 3380, 1682, 1726, 2111, 1751, 794, 2541, 2120, 4066, 3615, 719, 4052, 3868, 109, 2786, 2513, 1493, 2719, 2721, 168, 1970, 3353, 1686, 717, 2400, 1045, 1299, 3357, 2369, 3150, 3043, 3642, 4074, 2732, 2472, 3512, 4018, 3264, 2374, 2778, 3753, 2557, 2838, 1818, 2257, 2799, 828, 3839, 3308, 3806, 1345, 2246, 2171, 2442, 192, 3592, 750, 3027, 984, 1113, 1385, 758, 1634, 3643, 98, 2644, 142, 702, 2243, 4075, 70, 827, 2559, 1645, 2672, 2924, 3951, 2979, 1046, 66, 1478, 3926, 3190, 2094, 1450, 2776, 2061, 2555, 243, 3309, 1301, 3736, 2985, 60, 3607, 2849, 3787, 1642, 1098, 2346, 209, 1927, 2661, 94, 3070, 3800, 3731, 3280, 1572, 1252, 975, 3864, 1847, 3725, 3762, 3850, 1212, 3919, 4088, 1174, 581, 1930, 2863, 3700, 2500, 4169, 2294, 3412, 757, 791, 2899, 181, 525, 4036, 1649, 4063, 766, 3493, 460, 901, 598, 2694, 1121, 2615, 2368, 2256, 204, 667, 1043, 208, 2012, 3184, 2695, 1922, 1953, 1383, 500, 2743, 4123, 4078, 78, 497, 138, 1155, 3648 |
| PZ8 | 3894, 1209, 1803, 3989, 1632, 1638, 2735, 2065, 3004, 1452, 4048, 4043, 4039, 3484, 3274, 3884, 583, 1654, 3497, 3991, 3039, 3066, 425, 1808, 1703, 4157, 264, 3069, 4109, 571, 3675, 186, 2364, 2676, 3458, 488, 2952, 1231, 981, 1672, 1157, 3790, 2451, 3098, 3241, 1067, 991, 2556, 1264, 4057, 3707, 3056, 3138, 957, 146, 1987, 1564, 365, 821, 83, 1565, 707, 669, 431, 3747, 199, 3677, 4152, 1841, 402, 3475, 3270, 599, 2511, 2915, 3717, 1330, 2831, 532, 3057, 2263, 2190, 1414, 3231, 292, 2522, 1344, 3319, 839, 383, 610, 119, 554, 1208, 1285, 2476, 1696, 2379, 2880, 1946, 4051, 1976, 1872, 3622, 1277, 3959, 712, 3952, 3518, 3255, 2181, 400, 104, 1053, 118, 71, 1860, 3124, 1792, 2457, 3992, 941, 1739, 1057, 644, 1785, 4112, 1475, 1296, 1315, 2720, 1827, 1777, 4040, 526, 1461, 3106, 3020, 1532, 1624, 3964, 1014, 2296, 1797, 3345, 3457, 81, 2725, 1760, 89, 2328, 1684, 796, 3379, 2253, 3668, 2937, 476, 2931, 2793, 3639, 2771, 3874, 2005, 3817, 3940, 197, 1084, 2779, 773, 3145, 3596, 2713, 885, 1110, 1391, 1543, 1778, 3045, 1381, 1083, 3960, 1112, 3014, 2874, 1618, 615, 2285, 890, 2903, 3908, 3182, 1836, 3905, 1996, 1550, 4124, 2965, 505, 2333, 2141, 3054, 2554, 2170, 1971, 2716, 3692, 2075, 1038, 4176, 2003, 1583, 2107, 3151, 2116, 695, 3436, 4037, 2796, 1111, 3851, 1398, 1650, 3038, 3026, 2384, 1494, 3199, 3674, 3657, 461, 3555, 3434, 2123, 3478, 3439, 1031, 3221, 4160, 2886, 1075, 851, 2308, 3730, 4145, 441, 1708, 433, 3828, 3251, 1992, 1613, 2309, 3861, 3741, 3932 |
| PZ9 | 1278, 904, 1630, 2812, 2710, 3185, 1184, 3296, 2420, 2728, 2938, 3291, 3699, 928, 540, 3143, 414, 198, 329, 440, 3815, 1374, 3466, 2441, 1226, 421, 3009, 3924, 570, 1141, 1914, 3076, 1687, 361, 3154, 4143, 287, 1018, 917, 3196, 1782, 2897, 2168, 840, 3082, 2515, 2813, 1051, 513, 3999, 3191, 768, 2597, 2109, 3328, 1699, 3501, 1197, 1260, 1356, 3898, 3891, 3256, 4134, 3021, 1434, 732, 1676, 406, 2943, 528, 2619, 3823, 2760, 657, 1480, 2856, 742, 1422, 312, 1526, 2149, 3609, 782, 3739, 294, 252, 2144, 3559, 1700, 4140, 3587, 4023, 1378, 2755, 511, 3824, 1912, 2894, 3774, 2708, 374, 679, 552, 3886, 2194, 2982, 3292, 1384, 1245, 834, 3935, 249, 3580, 49, 3578, 1283, 2129, 2841, 3336, 2453, 2444, 2135, 3549, 144, 638, 3713, 1271, 3807, 2962, 3975, 1555, 1917, 741, 2521, 2670, 213, 3958, 2980, 1605, 74, 3783, 282, 3617, 2367, 2893, 333, 2403, 2013, 2702, 1855, 364, 2552, 1024, 2486, 2545, 59, 3037, 544, 1951, 1133, 1925, 3135, 627, 1740, 2447, 363, 91, 1680, 3423, 3258, 3470, 2255, 2571, 577, 1830, 1590, 2707, 3827, 3094, 929, 2781, 3149, 1617, 1588, 285, 2681, 3330, 2445, 2960, 2505, 3638, 1846, 3893, 2092, 1541, 832, 2304, 4025, 3442, 3567, 3359, 2536, 622, 1292, 1595, 3006, 2928, 3032, 274, 2216, 1884, 214, 1755, 2460, 1627, 2825, 1368, 3768, 3877, 1895, 1580, 512, 2948, 1943, 3902, 1122, 502, 2198, 2482, 23, 1537, 2654, 288, 1644, 1224, 4156, 3132, 17, 4148, 2535, 1313, 2701, 3714, 2944, 120, 3402, 2547, 2709, 4069, 2591, 1123, 2866, 2688, 3213, 2021 |
| PZ10 | 2314, 4010, 4000, 3306, 877, 79, 3808, 297, 2657, 561, 1621, 3225, 602, 2605, 437, 1348, 2281, 1243, 2316, 1114, 800, 7, 1161, 467, 2388, 2520, 4060, 281, 1060, 2436, 3417, 2480, 1335, 2634, 2398, 420, 2775, 1319, 2259, 2401, 2274, 2787, 1713, 1548, 1988, 3892, 3481, 4130, 358, 2098, 4126, 833, 3846, 1885, 1856, 176, 6, 24, 21, 945, 2134, 343, 824, 1641, 3755, 3302, 677, 493, 934, 4120, 3378, 490, 3303, 4099, 2628, 2352, 555, 2385, 1289, 3811, 1723, 3503, 1088, 2376, 155, 1371, 2334, 3217, 1447, 1842, 309, 1042, 1010, 2618, 2188, 696, 3210, 1757, 1443, 578, 663, 3244, 3754, 3167, 2128, 2680, 2477, 1351, 2611, 1786, 3236, 3788, 3078, 1561, 38, 2183, 3649, 831, 1772, 1248, 2394, 2558, 3611, 919, 2600, 1939, 2307, 3629, 2051, 169, 3531, 1175, 4084, 2244, 3146, 179, 3576, 4082, 783, 3361, 2404, |

TABLE 2-continued

Mixing Pool and Corresponding Clone Numbers contained therein

|      | |
|------|---|
|      | 1710, 2366, 1828, 238, 868, 379, 1334, 3927, 1819, 2029, 2392, 2574, 998, 1032, 4021, 2601, 3522, 1074, 616, 825, 1376, 3705, 1822, 3366, 45, 3216, 1573, 336, 1320, 924, 1309, 1789, 3480, 1346, 2693, 227, 1104, 5, 4087, 1326, 3430, 1162, 2958, 1302, 3690, 72, 2987, 3095, 2570, 1866, 1633, 935, 491, 411, 1100, 3860, 1788, 1025, 2229, 1086, 4035, 2534, 4022, 268, 3128, 2101, 8, 3732, 2497, 1756, 2806, 2204, 2942, 3406, 2968, 2660, 623, 3170, 1601, 3177, 3408, 1945, 2498, 3015, 2166, 3422, 710, 2461, 446, 151, 3835, 1815, 3773, 2532, 3852, 3311, 2692, 1531, 2062, 3425, 567, 751, 892, 2782, 3557, 143, 3263, 3089, 1858, 1015, 1218, 1551, 3711, 88, 415 |
| PZ11 | 3431, 2645, 3524, 3801, 2860, 3121, 654, 4079, 3386, 2341, 232, 3703, 1234, 844, 1037, 2510, 1203, 3365, 481, 1915, 1546, 3312, 240, 3683, 3967, 2868, 2014, 1186, 1430, 1553, 3515, 3776, 3837, 2871, 2099, 858, 2538, 932, 629, 3887, 1070, 3831, 3738, 3966, 108, 530, 2001, 3465, 1321, 2784, 484, 716, 342, 234, 2409, 3595, 3574, 1533, 3120, 2050, 404, 1026, 3223, 3748, 2850, 3242, 133, 3840, 2550, 743, 1178, 2154, 3081, 1898, 818, 3112, 3331, 607, 579, 3110, 651, 226, 2567, 2185, 3941, 1164, 2904, 2233, 3459, 84, 56, 320, 200, 2913, 1593, 2365, 3471, 105, 77, 2739, 2977, 1497, 2426, 3142, 952, 668, 3219, 4071, 372, 1897, 633, 1683, 3614, 1307, 2869, 785, 1637, 1402, 826, 1366, 2939, 690, 1911, 2163, 4163, 3538, 2768, 879, 543, 784, 1698, 3115, 2228, 1106, 645, 160, 1232, 2625, 1990, 857, 2434, 3691, 3504, 2669, 1839, 1525, 1954, 30, 1602, 3757, 2929, 918, 3407, 3301, 2068, 1535, 3443, 1653, 4004, 2731, 418, 3506, 475, 113, 559, 3630, 1905, 1347, 3477, 2391, 3229, 3445, 3415, 427, 4119, 1890, 92, 353, 359, 3910, 3339, 1978, 1863, 67, 1448, 231, 3655, 2997, 1775, 4103, 1549, 3536, 345, 1869, 3193, 3283, 2643, 2017, 2124, 2423, 3010, 435, 1984, 2562, 3381, 3624, 3383, 394, 1918, 2826, 2268, 3734, 3841, 2830, 3507, 993, 1784, 2549, 1102, 3498, 1479, 2718, 2506, 1780, 1365, 3791, 61, 2586, 1039, 87, 494, 2069, 2417, 683, 1041, 3889, 972, 3865, 1490, 3928, 223, 4091, 1790, 1701, 499, 2416, 1350, 1138, 1242, 1690, 2041, 3491, 586, 4005, 760, 3779 |
| PZ12 | 2015, 546, 3945, 2588, 4047, 2587, 3996, 1413, 3500, 3822, 1721, 2418, 709, 3623, 3452, 2675, 2730, 1306, 280, 3195, 950, 956, 3208, 3486, 3399, 2747, 2236, 1967, 2638, 3805, 1198, 575, 1229, 2921, 1604, 3451, 2048, 1659, 3169, 738, 121, 3327, 73, 2191, 1459, 772, 76, 2947, 450, 4041, 1322, 1270, 2195, 2119, 3284, 3988, 2607, 225, 1892, 300, 752, 838, 3048, 2337, 1472, 2699, 317, 3676, 2846, 3647, 3593, 1235, 2383, 1495, 2487, 3586, 3980, 1569, 3760, 951, 1370, 968, 884, 2665, 1685, 2999, 3029, 2160, 3970, 1899, 338, 2509, 3235, 3880, 305, 3537, 3218, 3440, 2474, 1570, 3113, 366, 31, 1272, 210, 2060, 2443, 1152, 1453, 4012, 515, 2839, 1266, 3289, 3490, 759, 330, 841, 722, 769, 1955, 3372, 2295, 3871, 2248, 2011, 2927, 3384, 689, 4024, 518, 815, 1518, 523, 959, 1204, 1064, 1500, 3562, 921, 3420, 779, 1579, 2706, 3494, 731, 3342, 3472, 1983, 3369, 319, 2169, 4033, 903, 3454, 3304, 3178, 2327, 4138, 1237, 3922, 2479, 3721, 537, 3363, 3636, 195, 162, 1066, 180, 1325, 260, 392, 1058, 1636, 3796, 1920, 2174, 2165, 1581, 2553, 962, 2930, 1681, 1544, 4065, 4085, 1731, 1692, 2146, 2617, 3744, 2988, 4030, 2430, 2213, 3564, 3041, 1709, 1582, 2348, 2046, 3604, 2412, 1341, 3156, 375, 4046, 3273, 2525, 2898, 3460, 3496, 2882, 4001, 1903, 1170, 206, 337, 380, 1286, 974, 1395, 2561, 3446, 2949, 2862, 1009, 3832, 3133, 2218, 527, 3843, 1420, 721, 3511, 909, 373, 126, 3321, 2502, 2303, 1861, 3398, 3946, 1567, 478, 278, 1524, 185, 2187, 163, 1762, 2467, 2043, 3233 |
| PZ13 | 41, 2350, 3795, 3735, 3888, 2629, 2578, 445, 3462, 3569, 1055, 2508, 3092, 3899, 1878, 1158, 2339, 3044, 58, 2496, 1505, 1126, 1168, 2649, 2951, 397, 520, 2700, 3881, 2087, 1429, 2986, 2819, 313, 2984, 1012, 1795, 2925, 2390, 1485, 976, 2326, 3317, 1377, 1482, 3060, 2829, 3349, 3904, 2895, 159, 1997, 3147, 931, 1991, 102, 3767, 1611, 3688, 1408, 1906, 1516, 864, 3035, 3307, 2270, 395, 1619, 4097, 3067, 2002, 589, 853, 3385, 3563, 3447, 3179, 3953, 2266, 2748, 316, 2437, 3915, 1931, 2920, 1028, 2884, 847, 1352, 600, 820, 640, 4019, 2360, 1392, 3181, 2440, 1665, 3250, 3842, 1130, 1894, 3601, 966, 277, 271, 1616, 3483, 1913, 3560, 1891, 4014, 3985, 2527, 2389, 2130, 4003, 350, 2205, 2971, 2636, 3527, 324, 3551, 2737, 123, 1725, 2499, 55, 886, 2222, 3197, 3201, 1151, 1267, 3505, 1804, 3697, 1077, 2325, 2736, 3234, 233, 655, 371, 4179, 1594, 3775, 1449, 2454, 1290, 613, 265, 1004, 1873, 2864, 955, 459, 1183, 2156, 3684, 2769, 2059, 637, 3965, 2393, 3820, 1061, 4056, 2599, 4094, 946, 1222, 3114, 979, 276, 798, 3508, 776, 2028, 681, 157, 2703, 1435, 725, 2823, 3855, 3613, 4164, 2438, 1076, 147, 2855, 1814, 2033, 1585, 3257, 1125, 2252, 1513, 2254, 2344, 434, 1947, 3286, 2351, 2602, 510, 36, 2079, 4061, 3793, 3628, 1635, 3523, 1148, 2045, 548, 1615, 3166, 1013, 386, 591, 3096, 2610, 986, 3468, 2684, 3854, 1462, 2462, 3869, 4159, 2470, 422, 2857, 1297, 256, 3704, 995, 3872, 2614, 3011, 3214, 3671, 3441, 2189, 1825, 3781, 2142, 3542, 272, 1742, 3579, 797, 4110 |
| PZ14 | 244, 3285, 3610, 1369, 3584, 1718, 423, 401, 216, 2157, 3883, 2663, 636, 889, 1308, 1233, 3238, 1079, 263, 1705, 4121, 1492, 2678, 855, 2290, 2083, 961, 2247, 1587, 2230, 2093, 2685, 509, 3656, 2152, 2711, 1372, 3510, 1944, 560, 670, 1444, 848, 29, 1982, 3226, 3104, 617, 3816, 965, 2526, 1187, 3947, 1962, 2251, 3456, 1859, 3409, 3957, 1753, 3287, 1405, 3612, 1923, 3708, 1101, 259, 2820, 2548, 469, 106, 996, 835, 3867, 1660, 693, 1006, 129, 1874, 2656, 3939, 1314, 96, 1714, 2031, 1774, 1568, 1656, 4154, 2631, 1293, 1589, 2179, 3712, 2324, 2432, 1451, 4135, 1240, 1612, 3464, 4170, 1003, 114, 1295, 2039, 687, 164, 3997, 220, 792, 584, 2473, 2044, 221, 1438, 628, 3687, 4090, 1727, 2583, 4122, 1502, 2664, 318, 2298, 4006, 4007, 1249, 830, 506, 12, 718, 3337, 1711, 1052, 2518, 4178, 174, 1960, 3017, 43, 2577, 2193, 2908, 761, 836, 1410, 241, 1902, 1210, 1254, 3838, 905, 3063, 3126, 3215, 1924, 2726, 3354, 1829, 2082, 519, 2419, 270, 3410, 2761, 3857, |

TABLE 2-continued

Mixing Pool and Corresponding Clone Numbers contained therein

| | |
|---|---|
| | 3001, 457, 483, 908, 170, 2057, 601, 1767, 939, 2969, 2396, 4054, 3532, 1832, 1538, 3502, 3086, 978, 1816, 3621, 3023, 882, 2322, 39, 764, 2421, 2078, 2843, 1849, 1807, 1754, 2010, 1940, 3672, 3165, 2641, 2582, 4118, 1880, 3391, 2242, 3645, 536, 1241, 621, 597, 3660, 1648, 1465, 762, 3633, 2881, 960, 2818, 754, 3377, 1288, 3341, 3591, 3247, 3900, 3323, 2449, 191, 775, 2208, 807, 988, 1312, 1182, 3387, 2575, 1799, 3403, 4042, 2764, 2167, 1215, 2686, 52, 1534, 907, 1149, 2885, 26, 3936, 2201, 3923 |
| PZ15 | 2066, 2834, 582, 2507, 2240, 1498, 2261, 3222, 2785, 2691, 1343, 2378, 933, 3368, 184, 3489, 68, 2086, 3810, 286, 356, 1974, 2658, 1868, 3049, 3659, 2302, 1910, 2023, 529, 1128, 3400, 3239, 95, 2355, 2284, 32, 2106, 2202, 2852, 2395, 1657, 2034, 3320, 3134, 2332, 819, 452, 2738, 1282, 1358, 2359, 3943, 416, 958, 444, 1896, 3942, 891, 3829, 3759, 674, 3882, 691, 4083, 4117, 2283, 3654, 1467, 369, 913, 3174, 1796, 1062, 139, 3103, 1722, 2821, 632, 193, 90, 116, 781, 4158, 4168, 4093, 188, 3259, 3802, 2081, 314, 678, 2512, 2122, 443, 3944, 3351, 1328, 219, 2199, 3546, 786, 182, 1005, 2844, 1484, 1620, 1257, 4073, 3706, 3626, 325, 1883, 2067, 897, 1805, 3644, 1675, 1027, 2589, 1099, 1415, 4162, 1416, 894, 1574, 3455, 2746, 876, 2679, 675, 3125, 464, 3972, 3680, 2809, 3652, 3421, 1340, 2598, 711, 2729, 3395, 1261, 2269, 653, 2514, 1748, 75, 2613, 387, 1738, 1514, 228, 2297, 3240, 1284, 1610, 2978, 2519, 1521, 1985, 1230, 339, 1844, 3912, 2335, 1332, 2640, 3473, 1217, 2226, 3833, 2301, 2655, 190, 3561, 2007, 2300, 398, 3585, 1171, 1324, 3764, 1499, 1143, 805, 1406, 2139, 2906, 1136, 1877, 922, 3313, 3890, 2250, 1095, 3352, 1463, 3277, 4101, 788, 2546, 2872, 417, 723, 3100, 803, 744, 947, 2992, 3139, 474, 3895, 3608, 2008, 1364, 699, 3826, 4147, 3534, 3168, 1850, 943, 2312, 1957, 2024, 756, 875, 246, 3984, 1129, 3797, 2089, 3758, 3396, 1393, 196, 3909, 2891, 3253, 872, 926, 85, 4166, 2727, 3914, 3583, 1724, 2478, 1156, 360, 1117, 2832, 3803 |
| OX0 | 1225, 68, 509, 3904, 1472, 651, 3210, 249, 1296, 2442, 3577, 3968, 1766, 3777, 1054, 4049, 2151, 2086, 3656, 2895, 2699, 226, 1757, 3580, 1315, 192, 1821, 2053, 4016, 2276, 1068, 382, 44, 3810, 2152, 159, 317, 2567, 1443, 49, 2720, 3592, 2585, 630, 2744, 620, 3599, 2125, 3661, 286, 2711, 1997, 3676, 2185, 578, 3578, 1827, 750, 2133, 3232, 1745, 64, 2835, 701, 1362, 356, 1372, 3147, 2846, 3941, 663, 1283, 1777, 3027, 262, 428, 239, 2790, 3918, 1093, 122, 1974, 3510, 931, 3647, 1164, 3244, 2129, 4040, 984, 1421, 910, 2349, 3685, 2916, 2998, 255, 2658, 1944, 1991, 3593, 2904, 3754, 2841, 526, 1113, 438, 2853, 2918, 3293, 2861, 3568, 608, 1868, 560, 102, 1235, 2233, 3167, 3336, 1461, 1385, 103, 612, 2495, 2415, 1666, 4142, 2740, 3049, 670, 3767, 2383, 3459, 2128, 2453, 3106, 758, 1446, 2132, 3594, 2042, 1047, 1783, 2593, 3659, 1444, 1611, 1495, 84, 2680, 2444, 3020, 1634, 2683, 565, 2749, 1728, 852, 399, 1089, 2302, 848, 3688, 2487, 56, 2477, 2135, 1532, 3643, 2054, 906, 1843, 1001, 1488, 1554, 201, 1910, 29, 1408, 3586, 320, 1351, 3549, 1624, 98, 2411, 2110, 3200, 2231, 351, 3640, 3130, 2023, 1982, 1906, 3980, 200, 2611, 144, 3964, 2644, 2237, 662, 16, 2172, 3343, 2217, 1059, 529, 3226, 1516, 1569, 2913, 1786, 638, 1014, 142, 1139, 429, 3047, 1107, 3756, 2757, 2155, 1128, 3104, 864, 3760, 1593, 3236, 3713, 2296, 702, 3653, 3873, 845, 680, 321, 2847, 1577, 3400, 617, 3035, 951, 2365, 3788, 1271, 1797, 2243, 463, 2673, 1559, 82, 3487, 1428 |
| OX1 | 1191, 3616, 3239, 3816, 3307, 1370, 3471, 3078, 3807, 3345, 4075, 1909, 1469, 665, 3243, 236, 3597, 808, 95, 965, 2270, 968, 105, 1561, 2962, 3457, 70, 480, 4132, 1300, 813, 3105, 1476, 3224, 2355, 2526, 395, 884, 77, 38, 3975, 81, 827, 4032, 1280, 2214, 3164, 606, 2080, 3558, 2284, 1187, 1619, 2665, 2739, 2183, 1555, 2725, 2559, 2742, 346, 2320, 4086, 2754, 869, 911, 32, 3947, 4097, 1685, 2977, 3649, 1917, 1760, 1645, 1932, 982, 916, 2630, 1091, 3144, 3667, 2106, 1962, 3067, 2999, 1497, 831, 741, 89, 2672, 165, 97, 1652, 2824, 624, 1704, 2733, 2202, 2251, 2002, 3029, 2426, 1772, 2521, 2328, 2924, 388, 3088, 2560, 473, 2356, 1223, 1952, 2852, 3456, 589, 2160, 3142, 1248, 2670, 1684, 3951, 1253, 4141, 27, 2635, 829, 564, 4015, 2395, 1859, 853, 3970, 952, 2394, 213, 796, 2979, 4165, 1022, 3907, 2175, 3545, 2126, 2387, 1657, 3409, 3385, 1899, 668, 2558, 3958, 3379, 1046, 1956, 1810, 1512, 2118, 2052, 1765, 1418, 2034, 3957, 3563, 338, 3219, 3611, 2980, 2253, 66, 3024, 1658, 40, 3183, 2468, 4136, 3127, 3320, 1753, 3447, 2509, 4071, 919, 1605, 3668, 1478, 3971, 254, 172, 3993, 3517, 1520, 3782, 3134, 3287, 3179, 3235, 372, 2600, 74, 2937, 3926, 2410, 3340, 1879, 251, 2452, 1382, 587, 2332, 1405, 3953, 3880, 1897, 1939, 3783, 476, 3190, 705, 639, 111, 1483, 3042, 1442, 2774, 819, 3612, 2266, 305, 633, 2307, 282, 2931, 2094, 1607, 3813, 2804, 728, 3903, 514, 3389, 452, 1923, 2748, 3537, 1683, 3629, 3617, 2793, 1450, 1120, 1017, 1547, 1791, 973 |
| OX2 | 3294, 217, 2104, 2738, 3708, 316, 3218, 3614, 2051, 2367, 3639, 2776, 3547, 780, 641, 2817, 3333, 763, 2353, 1282, 1101, 2437, 3440, 1307, 169, 2893, 2771, 2061, 2516, 2791, 3350, 3716, 2907, 1146, 2424, 1358, 259, 3915, 2474, 2869, 3531, 333, 3874, 2555, 3173, 1655, 1050, 1417, 367, 1298, 1743, 2359, 2820, 1931, 1570, 785, 1175, 2403, 2005, 243, 2439, 4151, 3427, 2802, 1468, 990, 1185, 3943, 2548, 2920, 3113, 1637, 4084, 2013, 3817, 3309, 3254, 3075, 2566, 3681, 1566, 2038, 1440, 416, 469, 1028, 366, 1402, 2244, 2702, 3940, 1301, 3152, 2004, 765, 2911, 2428, 3227, 3202, 958, 106, 2884, 31, 826, 3146, 1855, 197, 3736, 2363, 495, 2569, 822, 1511, 2922, 3397, 444, 996, 847, 1272, 1366, 179, 364, 1084, 2291, 2131, 2976, 3751, 652, 1394, 1759, 3572, 1896, 835, 1352, 210, 2939, 3576, 2552, 2779, 60, 496, 1268, 531, 3453, 1336, 787, 3625, 3942, 3867, 600, 2060, 690, 4082, 1024, 773, 3607, 2164, 454, 2879, 1081, 1975, 2603, 354, 891, 1660, 820, 2443, 1911, 783, 2486, 3145, 2849, 304, 3525, 3526, 3367, 1400, 3771, 1876, 3829, 693, 640, 1152, 2163, 3361, 2545, 3596, 3787, 2528, 2858, 3745, 4045, 1853, 3627, 2485, |

TABLE 2-continued

| | Mixing Pool and Corresponding Clone Numbers contained therein |
|---|---|
| | 3759, 1006, 4019, 1453, 4163, 2404, 59, 2713, 1642, 1528, 2347, 1812, 3689, 2471, 4044, 954, 674, 129, 2360, 4012, 3538, 1710, 3037, 885, 1098, 1729, 736, 1357, 2178, 302, 1741, 426, 3882, 1874, 1392, 515, 2768, 2366, 544, 1110, 2346, 1887, 2544, 3896, 1206, 2659, 2481, 3163, 691, 2656, 3181, 2839, 879, 1828, 1951, 1391, 209, 2975, 2503, 2159, 3696 |
| OX3 | 2073, 3438, 3679, 3678, 4083, 3939, 2440, 1266, 543, 238, 1133, 1543, 1927, 3844, 806, 3355, 774, 3205, 2239, 3159, 4117, 1314, 1665, 3289, 784, 868, 1925, 1778, 2661, 3411, 3172, 3814, 1973, 65, 166, 3911, 4139, 96, 3250, 3490, 1698, 379, 3135, 3045, 94, 2723, 10, 2584, 1199, 1908, 492, 4095, 2283, 1714, 3842, 759, 3115, 1334, 627, 1381, 3070, 1380, 1244, 2542, 3266, 2127, 862, 1800, 3654, 2031, 1130, 330, 2228, 3927, 1740, 1083, 3800, 1776, 2184, 3347, 3129, 2064, 2318, 715, 1467, 1774, 1894, 841, 1106, 1819, 2447, 3960, 3731, 2704, 3362, 1671, 3990, 301, 303, 1236, 369, 1568, 3601, 722, 645, 2029, 363, 1112, 3280, 1181, 1036, 3005, 3863, 2427, 1167, 2273, 913, 1656, 966, 769, 160, 2392, 91, 3014, 1572, 1353, 1919, 930, 547, 1694, 4020, 1764, 3174, 4154, 277, 1955, 1232, 2574, 1680, 2874, 1252, 1661, 1673, 1837, 295, 1150, 4011, 178, 1796, 2631, 271, 3372, 2625, 998, 3423, 1618, 975, 2386, 1545, 3448, 161, 3013, 2983, 594, 1062, 1293, 1616, 2295, 1990, 1032, 3258, 615, 3864, 1431, 1118, 3160, 1862, 273, 432, 3373, 139, 1589, 3483, 3871, 857, 4021, 3470, 2285, 1847, 3701, 2966, 1964, 2148, 1221, 3141, 1021, 3103, 2179, 1913, 2248, 2434, 2601, 2255, 890, 3725, 626, 3117, 2490, 3809, 1527, 1269, 2225, 1722, 3712, 3560, 2011, 3691, 3522, 2571, 2903, 3762, 504, 2622, 2162, 3079, 2662, 3157, 1662, 2821, 2324, 1891, 2927, 3504, 1074, 577, 3908, 3850, 4080, 870, 1214, 1310, 2848, 4017, 4106, 632, 2432, 4014, 3384, 2669, 616, 1830, 3182, 1212, 1323, 1840, 4026 |
| OX4 | 378, 3876, 2435, 3188, 1865, 193, 1451, 3985, 689, 1839, 825, 1590, 1836, 3919, 403, 334, 1172, 1926, 2102, 572, 4172, 90, 4135, 2527, 4024, 1525, 1376, 2707, 3905, 4088, 1507, 562, 1904, 1259, 1092, 1131, 1961, 116, 1240, 2389, 518, 1954, 3705, 3827, 1996, 1174, 203, 648, 4008, 1519, 413, 3268, 3335, 781, 1612, 2130, 815, 30, 1822, 3094, 1550, 581, 3746, 2935, 2095, 1424, 3052, 1515, 194, 4158, 3464, 4003, 1518, 1602, 3366, 929, 4124, 1930, 899, 2647, 854, 3733, 550, 245, 299, 4168, 4170, 350, 523, 3757, 45, 2781, 2965, 2863, 3435, 3804, 524, 1979, 3618, 1933, 112, 4093, 1003, 2205, 959, 2929, 3216, 3149, 505, 3700, 154, 3719, 2336, 2234, 2260, 2180, 1390, 188, 114, 2971, 1204, 918, 1573, 1617, 2333, 2500, 2140, 1069, 3332, 3539, 2345, 3786, 3769, 3259, 1295, 2636, 1064, 3407, 336, 1588, 2141, 4169, 3281, 1239, 385, 2794, 727, 1958, 883, 3802, 2039, 3527, 1500, 3301, 1320, 285, 3054, 2294, 2501, 3969, 2036, 1153, 724, 2354, 1287, 2081, 687, 324, 3562, 2068, 924, 2681, 2554, 3412, 0, 3482, 2836, 593, 967, 167, 1432, 314, 164, 3551, 921, 1535, 1309, 3330, 2170, 757, 1023, 1159, 3513, 1002, 230, 283, 697, 678, 3997, 2737, 3420, 3443, 1789, 2445, 1971, 791, 3606, 2543, 2221, 1504, 1575, 2756, 1716, 2512, 220, 123, 779, 1653, 3480, 2960, 2716, 2899, 940, 466, 1750, 563, 3046, 3488, 258, 2122, 792, 1725, 1579, 4004, 1346, 2505, 3692, 181, 3799, 2840, 2576, 1049, 2115, 1273, 1132, 443, 584, 2499, 2706, 2731, 2693, 3638, 2075, 525, 2224, 2533 |
| OX5 | 2652, 1889, 1768, 568, 3404, 3401, 3944, 2473, 55, 3494, 418, 227, 1846, 1038, 4036, 2084, 4171, 1137, 1044, 1599, 1597, 1734, 3351, 2044, 886, 731, 3506, 1104, 3893, 4176, 1649, 3875, 3870, 1928, 747, 2961, 1419, 3728, 1328, 221, 2222, 3342, 475, 5, 2092, 2003, 4063, 1124, 574, 611, 3516, 2483, 2696, 152, 219, 1438, 3197, 3472, 113, 4087, 1541, 1583, 766, 871, 2293, 1809, 1, 2887, 20, 4098, 2199, 628, 3201, 1983, 559, 1326, 832, 2107, 3493, 1730, 983, 2810, 3742, 969, 1674, 332, 3546, 3687, 1151, 3369, 3630, 3430, 2304, 3151, 460, 2828, 2650, 53, 2564, 1173, 1744, 218, 786, 4090, 1267, 319, 1905, 1162, 4025, 2116, 901, 2950, 992, 2262, 2789, 2845, 127, 927, 182, 1727, 3505, 2169, 1347, 2958, 3442, 695, 598, 3780, 682, 686, 767, 3729, 2192, 306, 1005, 2583, 1804, 4033, 3477, 1302, 3567, 3436, 2694, 2406, 250, 887, 588, 1761, 708, 2117, 2844, 4122, 3697, 903, 2391, 3690, 3359, 4037, 1121, 2722, 2056, 2606, 2854, 2210, 2687, 893, 1484, 1502, 1077, 3454, 3229, 72, 2536, 2796, 2615, 2381, 1669, 2803, 3519, 141, 1893, 2540, 1620, 2664, 2325, 3304, 3445, 2987, 622, 1111, 2368, 2837, 3853, 2741, 3765, 2085, 2981, 3429, 1257, 318, 2736, 3178, 3415, 3095, 1292, 3851, 2256, 2370, 3921, 2464, 1640, 1349, 2690, 4131, 4073, 2298, 3234, 2327, 427, 2570, 1595, 1398, 204, 1140, 3207, 46, 419, 3543, 2896, 2025, 3706, 4006, 233, 4138, 4119, 1866, 3006, 1650, 667, 2780, 549, 4137, 2753, 2811, 3825, 4125, 3626, 4007, 655, 1237, 1890, 1633, 2928, 3038, 1043, 859 |
| OX6 | 1950, 837, 1995, 4062, 1073, 455, 2450, 325, 1249, 371, 3922, 92, 935, 3032, 3026, 208, 3866, 1474, 2063, 3097, 3862, 595, 3300, 1883, 830, 4179, 2479, 353, 491, 274, 2384, 2012, 1942, 2878, 2223, 3710, 3074, 3598, 175, 2067, 506, 1594, 3721, 359, 411, 2216, 1494, 3184, 2653, 1108, 706, 3228, 3920, 449, 3552, 897, 12, 3775, 537, 3910, 1100, 1884, 3199, 2695, 2957, 1202, 298, 1470, 4116, 2724, 3080, 1805, 718, 1449, 3363, 3339, 3860, 214, 3674, 1922, 3925, 1201, 1831, 1034, 2890, 1426, 920, 3644, 3337, 2454, 3636, 1978, 1788, 1755, 3657, 1953, 1626, 2323, 1963, 1337, 1180, 1007, 2537, 1675, 1711, 1290, 195, 1863, 1025, 2460, 461, 1383, 1907, 2955, 522, 1715, 1437, 1165, 1258, 1027, 1052, 613, 162, 67, 2229, 1627, 3555, 500, 614, 3931, 2077, 659, 1078, 625, 3203, 2589, 2518, 265, 1066, 1448, 1086, 2825, 3434, 2743, 740, 3977, 3371, 1916, 1510, 1813, 4102, 1099, 4178, 1004, 180, 231, 4035, 1368, 2123, 4123, 2494, 2627, 3230, 4058, 396, 2006, 1623, 1415, 174, 1873, 1325, 3655, 2534, 3768, 3478, 4078, 517, 2319, 315, 3175, 2592, 15, 704, 4162, 1960, 2864, 260, 2997, 4022, 3877, 3439, 78, 381, 3424, 4173, 390, 3986, 3334, 2197, 1416, 3017, 955, 392, 1775, 268, 1895, 1031, 497, 348, 3978, 3521, 4174, 3034, 48, 553, 894, 43, 459, 1058, 4103, 3128, 1580, 3221, 138, 1354, 812, |

TABLE 2-continued

Mixing Pool and Corresponding Clone Numbers contained therein

|     |     |
| --- | --- |
|     | 684, 3405, 2158, 2859, 2493, 1574, 2577, 1183, 1636, 1549, 2101, 512, 4160, 1155, 3275, 42, 3073, 1949, 2000, 1881, 69, 3455, 2193, 2156, 3796, 3536, 8, 2948, 2886, 3648 |
| OX7 | 1663, 3778, 3153, 2851, 658, 3036, 2934, 2097, 2746, 2908, 3684, 1920, 345, 3732, 1943, 1075, 2745, 3278, 3792, 134, 1063, 1176, 3016, 237, 876, 761, 2769, 2174, 1869, 2497, 3902, 851, 1166, 3982, 2623, 3720, 3479, 1454, 3637, 1486, 2679, 836, 2059, 2165, 3193, 1756, 1122, 2308, 99, 1886, 2867, 1820, 3314, 2568, 4029, 1539, 675, 1410, 637, 1581, 3283, 2806, 502, 3730, 999, 866, 2200, 753, 2280, 3158, 2889, 2277, 3125, 241, 3965, 2553, 2643, 2204, 2198, 4145, 1423, 2565, 3556, 915, 1487, 2923, 2734, 2186, 464, 1902, 2393, 962, 2017, 2942, 2482, 441, 3693, 2973, 2425, 3664, 997, 1639, 2311, 3102, 3972, 1210, 3820, 2930, 2124, 3406, 23, 1708, 291, 2100, 3018, 3619, 3437, 3830, 2150, 2594, 3680, 1254, 1061, 1681, 2423, 2968, 1537, 433, 1501, 2037, 2551, 3262, 1339, 811, 2458, 2995, 2809, 3838, 4056, 1544, 3010, 2660, 2654, 3828, 3116, 177, 19, 3189, 2539, 2103, 3670, 3252, 3652, 905, 2599, 4065, 435, 623, 288, 3251, 3433, 4067, 3194, 35, 1048, 2488, 2161, 267, 3421, 3063, 4094, 4085, 1984, 3170, 1644, 1992, 2770, 2147, 3324, 2112, 3620, 468, 2375, 694, 1340, 3126, 946, 1731, 2562, 1601, 1224, 1613, 1331, 3544, 1192, 2689, 1720, 131, 1219, 735, 2598, 3215, 1222, 1692, 3381, 3177, 4156, 2309, 2182, 3673, 1035, 3414, 3934, 3338, 2377, 2264, 711, 1924, 3114, 2146, 3624, 3408, 3132, 3861, 2604, 3388, 2759, 137, 801, 2633, 1747, 1647, 2729, 2726, 979, 2617, 3383, 1945, 17, 3741, 1311, 424, 1481, 1702, 3031, 3245, 2299, 3723, 3395, 3354, 276, 3744, 394, 2498, 4148, 3932 |
| OX8 | 3894, 1763, 823, 4127, 2936, 2265, 482, 1852, 964, 1261, 1829, 798, 2988, 1918, 3015, 2535, 1209, 1969, 2579, 2766, 2573, 3050, 1980, 4013, 101, 2269, 2082, 3508, 4030, 2826, 2166, 1313, 1803, 1436, 3718, 2914, 3290, 2531, 2121, 923, 266, 653, 519, 776, 2430, 2268, 3422, 2701, 3989, 156, 1552, 1179, 802, 1540, 1247, 1989, 1781, 2514, 2419, 2028, 2213, 3734, 710, 3714, 1632, 2040, 799, 2909, 2763, 1959, 247, 2049, 410, 1748, 270, 681, 3564, 3841, 2461, 2944, 1638, 2469, 1706, 4068, 3694, 117, 3260, 2648, 1735, 75, 3410, 157, 3041, 2830, 446, 120, 2735, 1986, 57, 936, 1622, 3206, 269, 1563, 93, 2613, 2761, 2703, 1709, 3507, 151, 3402, 2065, 1770, 407, 814, 1717, 3137, 253, 1359, 2504, 387, 3857, 1435, 1582, 993, 3835, 2547, 3004, 2382, 1600, 1571, 80, 1968, 713, 1870, 3326, 1738, 3001, 725, 2348, 1784, 1815, 2709, 1452, 3083, 1387, 3784, 4133, 2964, 1477, 2019, 462, 1514, 457, 2823, 2046, 2549, 3773, 4069, 4048, 1864, 2027, 3974, 3248, 3155, 3979, 2448, 3573, 228, 483, 3855, 3604, 1102, 2532, 2591, 4043, 1011, 183, 2070, 3565, 673, 3237, 2651, 3724, 2297, 908, 3613, 2412, 3498, 3852, 1123, 4039, 1072, 3819, 3087, 1304, 3053, 977, 3246, 3938, 3240, 170, 4164, 1341, 1479, 3311, 2866, 3484, 456, 2524, 207, 2910, 1333, 2751, 2900, 944, 1284, 2057, 2438, 3156, 2718, 2692, 2688, 3274, 3533, 1263, 1664, 4144, 1427, 635, 2714, 3476, 1610, 601, 1076, 375, 2506, 1531, 3213, 3884, 733, 516, 1386, 62, 14, 1977, 2030, 2529, 2978, 1767, 147, 4046, 1780, 2062, 2021 |
| OX9 | 1278, 583, 3418, 3209, 2491, 145, 3000, 1769, 3983, 3749, 2519, 939, 2855, 3273, 1365, 3425, 904, 1654, 585, 850, 377, 1948, 2621, 2402, 2238, 3084, 1521, 2969, 1814, 2525, 3791, 567, 1630, 3497, 1190, 391, 3812, 604, 2926, 3376, 1854, 2091, 1985, 2396, 2033, 2898, 61, 751, 2812, 3991, 539, 215, 938, 2705, 937, 308, 2698, 700, 1230, 4054, 1585, 3460, 2586, 892, 2710, 3039, 2361, 355, 2642, 3589, 3186, 2612, 1389, 1316, 339, 3532, 3257, 3496, 1039, 2782, 3185, 3066, 2475, 393, 3390, 211, 4089, 730, 384, 2877, 1844, 1832, 1125, 2882, 87, 3557, 1184, 425, 896, 1668, 4059, 849, 3528, 150, 2196, 3025, 3912, 1538, 2252, 4001, 494, 143, 3296, 1808, 3269, 1160, 3474, 1019, 3148, 1116, 1517, 2088, 2335, 3502, 1513, 1903, 2069, 3263, 2420, 1703, 1096, 508, 326, 1556, 1596, 1614, 558, 746, 1332, 3086, 2254, 1170, 2417, 3089, 2728, 4157, 3702, 451, 3772, 2058, 4100, 3450, 2267, 1090, 2640, 978, 2344, 206, 683, 1858, 2938, 264, 1464, 3085, 873, 1491, 3590, 1008, 698, 3954, 3473, 1816, 434, 337, 1041, 1015, 3291, 3069, 2797, 2517, 2177, 284, 649, 3298, 994, 3315, 1217, 3621, 1947, 380, 3889, 1218, 3699, 4109, 296, 790, 2211, 2114, 2596, 1094, 412, 1412, 2226, 3023, 3286, 1286, 972, 1551, 928, 571, 2967, 685, 2595, 2076, 3662, 2798, 1934, 1373, 3833, 882, 2351, 974, 3865, 3711, 540, 3675, 3878, 1276, 2245, 405, 688, 1941, 229, 2321, 2301, 2322, 2602, 1395, 1490, 88, 3143, 186, 3916, 534, 1441, 487, 149, 279, 409, 2620, 2655, 39, 510, 2561, 3928, 415 |
| OX10 | 2314, 414, 2364, 3267, 3858, 1188, 2275, 3963, 1496, 3099, 3859, 190, 764, 36, 3446, 223, 4010, 198, 2676, 2136, 1329, 2609, 3394, 1999, 642, 646, 3299, 3561, 2421, 2079, 2949, 4091, 4000, 329, 3458, 1688, 4092, 389, 1736, 2752, 1355, 3602, 1397, 2007, 2078, 4061, 2862, 1790, 3306, 440, 488, 2677, 4111, 580, 881, 987, 1732, 1195, 1361, 2300, 2843, 3793, 1009, 1701, 877, 3815, 2952, 1407, 2946, 3950, 1787, 3743, 3449, 874, 1631, 398, 1849, 3628, 3832, 499, 79, 1374, 1231, 867, 1363, 3461, 3003, 2232, 471, 2800, 3131, 3585, 1807, 1635, 3133, 2416, 3808, 3466, 981, 1056, 2697, 3467, 1303, 158, 793, 1867, 63, 1171, 1754, 3523, 2218, 1350, 297, 2441, 1672, 703, 3937, 1213, 1291, 275, 1135, 2018, 3204, 1324, 2010, 1148, 527, 1138, 2657, 1226, 1157, 3180, 4149, 442, 2682, 980, 2580, 3019, 1746, 3764, 1940, 2045, 3843, 1242, 561, 421, 3790, 3288, 1033, 2772, 3310, 2380, 605, 925, 1207, 1499, 3672, 548, 1420, 1690, 1621, 3009, 2451, 3885, 4009, 3571, 3798, 3686, 2883, 1177, 1305, 1143, 3165, 1615, 721, 2041, 3225, 3924, 3098, 745, 2212, 1646, 1591, 3055, 130, 888, 107, 805, 2641, 3166, 3511, 3491, 602, 570, 3241, 1689, 3836, 3766, 3987, 2991, 2765, 2272, 2758, 1406, 2582, 1013, 909, 586, 2605, 1141, 1067, 2357, 861, 3090, 2972, 3192, 2431, 2715, 3726, 2139, 4118, 386, 373, 4005, 437, 1914, 991, 2071, 989, 2291, 1460, 860, 453, 2876, 2279, 2906, 1880, |

TABLE 2-continued

Mixing Pool and Corresponding Clone Numbers contained therein

|  |  |
|---|---|
|  | 591, 126, 760, 1348, 3076, 2556, 3995, 3118, 3845, 863, 1189, 212, 590, 2783, 1136, 3391, 3096, 3321, 3779 |
| OX11 | 3431, 2281, 1687, 1264, 3051, 3358, 2919, 3392, 2342, 2433, 3582, 1643, 1877, 2242, 2610, 2502, 2645, 1243, 361, 4057, 4129, 789, 843, 2282, 171, 2072, 189, 2671, 922, 3645, 986, 2303, 3524, 2316, 3154, 3707, 2590, 3879, 2974, 3346, 2096, 3632, 2219, 2917, 3313, 536, 3468, 1861, 3801, 1114, 4143, 3056, 1530, 3535, 124, 2816, 1082, 3540, 3848, 596, 3890, 1241, 2684, 3398, 2860, 800, 287, 3138, 140, 1080, 1255, 1071, 647, 521, 2459, 2712, 2250, 621, 3854, 3946, 3121, 7, 1018, 957, 128, 4177, 1935, 592, 1758, 557, 2827, 3265, 1095, 597, 1462, 1567, 654, 1161, 917, 146, 3136, 4072, 3119, 2902, 3550, 2137, 1445, 3295, 3352, 3660, 2462, 478, 4079, 467, 3196, 1987, 748, 3901, 3631, 3058, 33, 3981, 2455, 2340, 1463, 1648, 3869, 278, 3386, 2388, 1782, 1564, 2639, 664, 2287, 4077, 1937, 2523, 3575, 4028, 3277, 1465, 4159, 1524, 2341, 2520, 2897, 365, 3469, 86, 3973, 3976, 3322, 2954, 310, 4081, 4101, 762, 2470, 185, 232, 4060, 2168, 821, 4076, 1279, 771, 3419, 569, 545, 3581, 2888, 788, 3633, 422, 2187, 3703, 281, 840, 83, 3930, 2206, 3709, 1360, 1806, 533, 2292, 2286, 2546, 2881, 2857, 163, 1234, 1060, 3082, 1565, 25, 619, 3641, 1875, 4105, 2331, 878, 3763, 2872, 960, 1297, 1762, 844, 2436, 2515, 707, 125, 3356, 3570, 2990, 2055, 1529, 3064, 676, 417, 2818, 256, 2467, 1037, 3417, 2813, 669, 2901, 2608, 1127, 2970, 2717, 4038, 37, 734, 723, 754, 3704, 2043, 2510, 2480, 1051, 431, 2020, 3272, 2842, 1811, 2762, 447, 327, 293, 3100, 3377, 995, 3233 |
| OX12 | 2015, 1203, 1335, 513, 3747, 2465, 347, 235, 1826, 2865, 749, 726, 3499, 803, 1288, 3872, 546, 3365, 2634, 3999, 199, 3012, 1040, 18, 1433, 3961, 3109, 9, 3279, 744, 3341, 2614, 3945, 481, 2398, 3191, 3677, 331, 1695, 777, 34, 3426, 430, 1029, 2414, 947, 3591, 3011, 2588, 1915, 420, 768, 4152, 3071, 1697, 1169, 4113, 2666, 1536, 3198, 895, 2992, 3247, 3214, 4047, 1546, 2775, 2597, 1841, 2143, 439, 1251, 2956, 1265, 3485, 2215, 50, 3139, 3900, 3671, 2587, 3312, 1319, 2109, 402, 2941, 3162, 2626, 2235, 1327, 3325, 51, 737, 474, 3323, 3441, 3996, 240, 2259, 3328, 3475, 912, 2305, 3059, 1147, 507, 47, 817, 3847, 3895, 2449, 2189, 1413, 3683, 2401, 1699, 3270, 671, 477, 661, 1489, 1388, 448, 1523, 4114, 3608, 191, 1825, 3500, 3967, 2274, 3501, 599, 3161, 3666, 985, 1824, 2271, 656, 3962, 357, 2008, 775, 3781, 3822, 2868, 2787, 1197, 2511, 289, 3948, 816, 1246, 2047, 900, 1109, 3658, 1364, 2208, 2142, 1721, 2014, 1713, 1260, 2915, 3122, 3282, 1262, 4115, 3665, 2289, 3271, 3849, 699, 807, 3542, 2418, 1186, 1548, 1356, 3717, 3380, 3093, 1628, 1606, 2668, 1560, 2466, 1771, 3826, 988, 272, 709, 1430, 1988, 3898, 1330, 1682, 3101, 2397, 1399, 846, 643, 344, 1196, 4147, 1312, 1742, 3623, 1553, 3892, 3891, 2831, 1726, 498, 2463, 3370, 3065, 1281, 1845, 1097, 3534, 1182, 3579, 3452, 3515, 3481, 3256, 532, 2111, 2407, 3068, 1817, 352, 1473, 1506, 503, 3168, 3387, 797, 2675, 3776, 4130, 4134, 3057, 1751, 4031, 3529, 1936, 3509, 3002, 2035, 465, 1850, 2575, 4110 |
| OX13 | 41, 2730, 3837, 358, 3021, 2263, 794, 501, 535, 1338, 778, 1103, 1238, 4064, 943, 1799, 2350, 1306, 2871, 2098, 1434, 2190, 2541, 1691, 3548, 2145, 1457, 335, 3108, 2288, 2312, 3403, 3795, 280, 2099, 4126, 732, 1414, 2120, 2815, 479, 650, 3955, 880, 136, 1584, 1957, 4042, 3735, 3195, 858, 833, 1676, 3231, 4066, 2153, 1294, 1250, 4146, 2801, 4050, 3600, 2024, 2764, 3888, 950, 2538, 3846, 406, 292, 3615, 755, 714, 1794, 2767, 3492, 914, 1798, 756, 2167, 2629, 956, 932, 1885, 2943, 2522, 719, 2016, 3737, 3463, 1409, 1888, 3072, 2358, 875, 1215, 2578, 3208, 629, 1856, 528, 1344, 4052, 2413, 100, 1105, 3276, 1871, 3413, 842, 246, 2686, 445, 3486, 3887, 176, 2619, 3319, 3868, 2993, 368, 4104, 3913, 2994, 3698, 3261, 3984, 52, 3462, 3399, 1070, 6, 3823, 839, 109, 148, 1401, 2795, 3176, 3818, 323, 1558, 1129, 1534, 3569, 2747, 3831, 24, 2760, 383, 2786, 3344, 1503, 1216, 2113, 1592, 370, 2241, 3797, 907, 1055, 2236, 3738, 21, 657, 610, 2513, 3432, 1466, 3785, 2808, 1030, 1965, 2220, 2089, 1149, 2508, 1967, 3966, 945, 1480, 119, 1493, 1779, 1609, 4002, 135, 2373, 795, 2429, 3758, 2885, 3092, 2638, 108, 2134, 2856, 554, 2719, 1838, 261, 1576, 2176, 1929, 1625, 3740, 3396, 26, 3899, 3805, 530, 343, 742, 1208, 2721, 1651, 739, 2343, 902, 1938, 2912, 1901, 1393, 3936, 1878, 1198, 2001, 824, 1422, 1285, 168, 1396, 1119, 729, 2315, 3187, 1065, 660, 196, 2201, 1158, 575, 3465, 1641, 312, 2476, 1970, 3715, 1020, 1707, 2833, 1509, 224, 4153, 3909, 3923 |
| OX14 | 244, 2339, 1229, 1321, 3755, 1526, 1696, 3353, 3040, 173, 2873, 971, 1456, 631, 311, 2891, 3285, 3044, 2921, 2784, 3302, 2149, 2379, 1686, 3123, 3033, 2022, 1823, 1379, 1142, 2646, 3253, 3610, 58, 1604, 484, 677, 3609, 2880, 717, 3929, 2777, 3062, 1194, 1134, 28, 3917, 872, 1369, 2496, 3451, 716, 493, 782, 1946, 2400, 1200, 2456, 110, 2932, 3588, 2945, 3028, 926, 3584, 1505, 2048, 342, 934, 3739, 4051, 1045, 1833, 609, 1403, 22, 3906, 1227, 1275, 85, 1718, 1126, 1659, 234, 4120, 294, 1976, 1299, 408, 1966, 3382, 2338, 222, 1667, 1375, 4166, 423, 1168, 3169, 2409, 3378, 252, 1872, 3357, 2822, 1144, 3318, 898, 2, 1274, 3514, 2727, 401, 2649, 738, 3595, 490, 2144, 3622, 2369, 3212, 3695, 132, 2310, 1994, 1679, 2330, 3914, 216, 2951, 121, 3574, 3303, 3559, 1277, 3150, 1993, 970, 3008, 1900, 4, 1411, 1677, 3583, 2157, 397, 3327, 1533, 4099, 1700, 3959, 3043, 1562, 2105, 963, 3, 4053, 328, 770, 1724, 3883, 520, 73, 3120, 2628, 4140, 712, 3642, 2372, 2362, 486, 3605, 1000, 376, 1367, 2478, 2663, 2700, 2191, 2050, 2352, 3587, 3952, 4074, 4055, 3220, 666, 1425, 692, 153, 3375, 1156, 636, 3881, 1459, 404, 555, 4023, 3518, 2732, 1115, 3603, 1455, 1851, 341, 1712, 2959, 360, 889, 2087, 772, 1026, 2385, 1378, 3255, 2472, 2624, 362, 202, 3794, 2667, 3444, 485, 1117, 1308, 1429, 76, 3223, 1289, 2755, 2181, 3512, 2492, 2278, 2422, 1629, 3305, 1557, 322, 2832, 1233, 2986, 2947, 3748, 3811, 511, 400, 4018, 1228, 1154, 1193, 2572, 1439, 1542, 4027, 3803 |

TABLE 2-continued

| Mixing Pool and Corresponding Clone Numbers contained therein | |
|---|---|
| OX15 | 2066, 3238, 2819, 450, 2850, 1723, 3824, 104, 3264, 618, 1998, 810, 3171, 3761, 3663, 3091, 2834, 1079, 313, 4041, 3242, 3503, 1912, 1053, 2374, 187, 2408, 205, 1719, 2996, 2032, 1085, 582, 263, 2984, 1322, 133, 1088, 2894, 118, 2778, 1834, 1793, 720, 248, 1508, 804, 2870, 2507, 1705, 1012, 1270, 3840, 2376, 3774, 71, 3753, 4107, 1801, 4108, 2814, 2405, 3416, 3669, 2240, 4121, 1795, 2195, 2550, 155, 2708, 1860, 2557, 3897, 556, 1586, 538, 1835, 4128, 1848, 1498, 1492, 2925, 2119, 743, 1371, 374, 3124, 2838, 1163, 3650, 3428, 3933, 2249, 489, 2892, 2261, 2678, 2390, 3284, 1178, 2334, 679, 1792, 1818, 2875, 1578, 3722, 1471, 3520, 1608, 3949, 3222, 855, 1485, 3988, 2154, 3217, 552, 2457, 2257, 566, 115, 1693, 3682, 809, 2446, 2313, 2785, 2290, 976, 2607, 3081, 1447, 3886, 3992, 2799, 1972, 2203, 2489, 2399, 242, 3635, 3634, 2691, 2083, 2326, 225, 1898, 1842, 2194, 941, 828, 2616, 2090, 1205, 2940, 1404, 3364, 3998, 1343, 961, 3317, 1892, 818, 309, 2982, 1739, 3839, 3022, 1773, 3553, 2026, 2805, 2953, 3646, 2378, 2247, 1377, 300, 3112, 1042, 3292, 1057, 3308, 1458, 1670, 4155, 3061, 2227, 3249, 2750, 933, 1587, 1482, 752, 3331, 1010, 1384, 644, 3806, 257, 3770, 2989, 470, 1598, 942, 541, 3368, 2230, 3060, 838, 607, 2618, 1245, 1785, 1345, 1752, 634, 2632, 2905, 2207, 603, 436, 184, 2093, 2829, 3048, 579, 2188, 834, 4112, 2246, 856, 2317, 2674, 3077, 2581, 2173, 3329, 3489, 2685, 3349, 2337, 3110, 696, 3935, 1475, 2171, 953, 1857, 2963, 472, 1921, 2792, 1981 |
| OY0 | 2066, 3238, 2819, 450, 2850, 1723, 3824, 104, 3264, 618, 1998, 810, 3171, 3761, 3663, 3091, 3285, 3044, 2921, 2784, 3302, 2149, 2379, 1686, 3123, 3033, 2022, 1823, 1379, 1142, 2646, 3253, 3795, 280, 2099, 4126, 732, 1414, 2120, 2815, 479, 650, 3955, 880, 136, 1584, 1957, 4042, 2588, 1915, 420, 768, 4152, 3071, 1697, 1169, 4113, 2666, 1536, 3198, 895, 2992, 3247, 3214, 2860, 800, 287, 3138, 140, 1080, 1255, 1071, 647, 521, 2459, 2712, 2250, 621, 3854, 3946, 79, 1374, 1231, 867, 1363, 3461, 3003, 2232, 471, 2800, 3131, 3585, 1807, 1635, 3133, 2416, 1184, 425, 896, 1668, 4059, 849, 3528, 150, 2196, 3025, 3912, 1538, 2252, 4001, 494, 143, 2065, 1770, 407, 814, 1717, 3137, 253, 1359, 2504, 387, 3857, 1435, 1582, 993, 3835, 2547, 1501, 2037, 2551, 3262, 1339, 811, 2458, 2995, 2809, 3838, 4056, 1544, 3010, 2660, 2654, 3828, 740, 3977, 3371, 1916, 1510, 1813, 4102, 1099, 4178, 1004, 180, 231, 4035, 1368, 2123, 4123, 2056, 2606, 2854, 2210, 2687, 893, 1484, 1502, 1077, 3454, 3229, 72, 2536, 2796, 2615, 2381, 2836, 593, 967, 167, 1432, 314, 164, 3551, 921, 1535, 1309, 3330, 2170, 757, 1023, 1159, 2148, 1221, 3141, 1021, 3103, 2179, 1913, 2248, 2434, 2601, 2255, 890, 3725, 626, 3117, 2490, 2471, 4044, 954, 674, 129, 2360, 4012, 3538, 1710, 3037, 885, 1098, 1729, 736, 1357, 2178, 1442, 2774, 819, 3612, 2266, 305, 633, 2307, 282, 2931, 2094, 1607, 3813, 2804, 728, 3903, 1577, 3400, 617, 3035, 951, 2365, 3788, 1271, 1797, 2243, 463, 2673, 1559, 82, 3487, 1428 |
| OY1 | 244, 2339, 1229, 1321, 3755, 1526, 1696, 3353, 3040, 173, 2873, 971, 1456, 631, 311, 2891, 2350, 1306, 2871, 2098, 1434, 2190, 2541, 1691, 3548, 2145, 1457, 335, 3108, 2288, 2312, 3403, 3945, 481, 2398, 3191, 3677, 331, 1695, 777, 34, 3426, 430, 1029, 2414, 947, 3591, 3011, 3801, 1114, 4143, 3056, 1530, 3535, 124, 2816, 1082, 3540, 3848, 596, 3890, 1241, 2684, 3398, 877, 3815, 2952, 1407, 2946, 3950, 1787, 3743, 3449, 874, 1631, 398, 1849, 3628, 3832, 499, 3185, 3066, 2475, 393, 3390, 211, 4089, 730, 384, 2877, 1844, 1832, 1125, 2882, 87, 3557, 2735, 1986, 57, 936, 1622, 3206, 269, 1563, 93, 2613, 2761, 2703, 1709, 3507, 151, 3402, 291, 2100, 3018, 3619, 3437, 3830, 2150, 2594, 3680, 1254, 1061, 1681, 2423, 2968, 1537, 433, 614, 3931, 2077, 659, 1078, 625, 3203, 2589, 2518, 265, 1066, 1448, 1086, 2825, 3434, 2743, 250, 887, 588, 1761, 708, 2117, 2844, 4122, 3697, 903, 2391, 3690, 3359, 4037, 1121, 2722, 2036, 1153, 724, 2354, 1287, 2081, 687, 324, 3562, 2068, 924, 2681, 2554, 3412, 0, 3482, 1862, 273, 432, 3373, 139, 1589, 3483, 3871, 857, 4021, 3470, 2285, 1847, 3701, 2966, 1964, 1853, 3627, 2485, 3759, 1006, 4019, 1453, 4163, 2404, 59, 2713, 1642, 1528, 2347, 1812, 3689, 1382, 587, 2332, 1405, 3953, 3880, 1897, 1939, 3783, 476, 3190, 705, 639, 111, 1483, 3042, 2155, 1128, 3104, 864, 3760, 1593, 3236, 3713, 2296, 702, 3653, 3873, 845, 680, 321, 2847, 3489, 2685, 3349, 2337, 3110, 696, 3935, 1475, 2171, 953, 1857, 2963, 472, 1921, 2792, 1981 |
| OY2 | 2652, 1889, 1768, 568, 3404, 3401, 3944, 2473, 55, 3494, 418, 227, 1846, 1038, 4036, 2084, 1172, 1926, 2102, 572, 4172, 90, 4135, 2527, 4024, 1525, 1376, 2707, 3905, 4088, 1507, 562, 1973, 65, 166, 3911, 4139, 96, 3250, 3490, 1698, 379, 3135, 3045, 94, 2723, 10, 2584, 367, 1298, 1743, 2359, 2820, 1931, 1570, 785, 1175, 2403, 2005, 243, 2439, 4151, 3427, 2802, 869, 911, 32, 3947, 4097, 1685, 2977, 3649, 1917, 1760, 1645, 1932, 982, 916, 2630, 1091, 122, 1974, 3510, 931, 3647, 1164, 3244, 2129, 4040, 984, 1421, 910, 2349, 3685, 2916, 2998, 2261, 2678, 2390, 3284, 1178, 2334, 679, 1792, 1818, 2875, 1578, 3722, 1471, 3520, 1608, 3949, 401, 2649, 738, 3595, 490, 2144, 3622, 2369, 3212, 3695, 132, 2310, 1994, 1679, 2330, 3914, 3462, 3399, 1070, 6, 3823, 839, 109, 148, 1401, 2795, 3176, 3818, 323, 1558, 1129, 1534, 3822, 2868, 2787, 1197, 2511, 289, 3948, 816, 1246, 2047, 900, 1109, 3658, 1364, 2208, 2142, 232, 4060, 2168, 821, 4076, 1279, 771, 3419, 569, 545, 3581, 2888, 788, 3633, 422, 2187, 3225, 3924, 3098, 745, 2212, 1646, 1591, 3055, 130, 888, 107, 805, 2641, 3166, 3511, 3491, 3699, 4109, 296, 790, 2211, 2114, 2596, 1094, 412, 1412, 2226, 3023, 3286, 1286, 972, 1551, 3484, 456, 2524, 207, 2910, 1333, 2751, 2900, 944, 1284, 2057, 2438, 3156, 2718, 2692, 2688, 2604, 3388, 2759, 137, 801, 2633, 1747, 1647, 2729, 2726, 979, 2617, 3383, 1945, 17, 3741, 3275, 42, 3073, 1949, 2000, 1881, 69, 3455, 2193, 2156, 3796, 3536, 8, 2948, 2886, 3648 |
| OY3 | 378, 3876, 2435, 3188, 1865, 193, 1451, 3985, 689, 1839, 825, 1590, 1836, 3919, 403, 334, 774, 3205, 2239, 3159, 4117, 1314, 1665, 3289, 784, 868, 1925, 1778, |

TABLE 2-continued

Mixing Pool and Corresponding Clone Numbers contained therein

|  |  |
|---|---|
|  | 2661, 3411, 3172, 3814, 2907, 1146, 2424, 1358, 259, 3915, 2474, 2869, 3531, 333, 3874, 2555, 3173, 1655, 1050, 1417, 2080, 3558, 2284, 1187, 1619, 2665, 2739, 2183, 1555, 2725, 2559, 2742, 346, 2320, 4086, 2754, 1362, 356, 1372, 3147, 2846, 3941, 663, 1283, 1777, 3027, 262, 428, 239, 2790, 3918, 1093, 1498, 1492, 2925, 2119, 743, 1371, 374, 3124, 2838, 1163, 3650, 3428, 3933, 2249, 489, 2892, 423, 1168, 3169, 2409, 3378, 252, 1872, 3357, 2822, 1144, 3318, 898, 2, 1274, 3514, 2727, 445, 3486, 3887, 176, 2619, 3319, 3868, 2993, 368, 4104, 3913, 2994, 3698, 3261, 3984, 52, 3500, 3967, 2274, 3501, 599, 3161, 3666, 985, 1824, 2271, 656, 3962, 357, 2008, 775, 3781, 2341, 2520, 2897, 365, 3469, 86, 3973, 3976, 3322, 2954, 310, 4081, 4101, 762, 2470, 185, 1621, 3009, 2451, 3885, 4009, 3571, 3798, 3686, 2883, 1177, 1305, 1143, 3165, 1615, 721, 2041, 3291, 3069, 2797, 2517, 2177, 284, 649, 3298, 994, 3315, 1217, 3621, 1947, 380, 3889, 1218, 4039, 1072, 3819, 3087, 1304, 3053, 977, 3246, 3938, 3240, 170, 4164, 1341, 1479, 3311, 2866, 2182, 3673, 1035, 3414, 3934, 3338, 2377, 2264, 711, 1924, 3114, 2146, 3624, 3408, 3132, 3861, 1354, 812, 684, 3405, 2158, 2859, 2493, 1574, 2577, 1183, 1636, 1549, 2101, 512, 4160, 1155, 549, 4137, 2753, 2811, 3825, 4125, 3626, 4007, 655, 1237, 1890, 1633, 2928, 3038, 1043, 859 |
| OY4 | 2073, 3438, 3679, 3678, 4083, 3939, 2440, 1266, 543, 238, 1133, 1543, 1927, 3844, 806, 3355, 3333, 763, 2353, 1282, 1101, 2437, 3440, 1307, 169, 2893, 2771, 2061, 2516, 2791, 3350, 3716, 1476, 3224, 2355, 2526, 395, 884, 77, 38, 3975, 81, 827, 4032, 1280, 2214, 3164, 606, 3661, 286, 2711, 1997, 3676, 2185, 578, 3578, 1827, 750, 2133, 3232, 1745, 64, 2835, 701, 2240, 4121, 1795, 2195, 2550, 155, 2708, 1860, 2557, 3897, 556, 1586, 538, 1835, 4128, 1848, 1718, 1126, 1659, 234, 4120, 294, 1976, 1299, 408, 1966, 3382, 2338, 222, 1667, 1375, 4166, 2578, 3208, 629, 1856, 528, 1344, 4052, 2413, 100, 1105, 3276, 1871, 3413, 842, 246, 2686, 1413, 3683, 2401, 1699, 3270, 671, 477, 661, 1489, 1388, 448, 1523, 4114, 3608, 191, 1825, 3386, 2388, 1782, 1564, 2639, 664, 2287, 4077, 1937, 2523, 3575, 4028, 3277, 1465, 4159, 1524, 561, 421, 3790, 3288, 1033, 2772, 3310, 2380, 605, 925, 1207, 1499, 3672, 548, 1420, 1690, 2938, 264, 1464, 3085, 873, 1491, 3590, 1008, 698, 3954, 3473, 1816, 434, 337, 1041, 1015, 4043, 1011, 183, 2070, 3565, 673, 3237, 2651, 3724, 2297, 908, 3613, 2412, 3498, 3852, 1123, 1331, 3544, 1192, 2689, 1720, 131, 1219, 735, 2598, 3215, 1222, 1692, 3381, 3177, 4156, 2309, 348, 3978, 3521, 4174, 3034, 48, 553, 894, 43, 459, 1058, 4103, 3128, 1580, 3221, 138, 3207, 46, 419, 3543, 2896, 2025, 3706, 4006, 233, 4138, 4119, 1866, 3006, 1650, 667, 2780, 2576, 1049, 2115, 1273, 1132, 443, 584, 2499, 2706, 2731, 2693, 3638, 2075, 525, 2224, 2533 |
| OY5 | 3294, 217, 2104, 2738, 3708, 316, 3218, 3614, 2051, 2367, 3639, 2776, 3547, 780, 641, 2817, 3597, 808, 95, 965, 2270, 968, 105, 1561, 2962, 3457, 70, 480, 4132, 1300, 813, 3105, 44, 3810, 2152, 159, 317, 2567, 1443, 49, 2720, 3592, 2585, 630, 2744, 620, 3599, 2125, 2507, 1705, 1012, 1270, 3840, 2376, 3774, 71, 3753, 4107, 1801, 4108, 2814, 2405, 3416, 3669, 3584, 1505, 2048, 342, 934, 3739, 4051, 1045, 1833, 609, 1403, 22, 3906, 1227, 1275, 85, 2629, 956, 932, 1885, 2943, 2522, 719, 2016, 3737, 3463, 1409, 1888, 3072, 2358, 875, 1215, 3996, 240, 2259, 3328, 3475, 912, 2305, 3059, 1147, 507, 47, 817, 3847, 3895, 2449, 2189, 4079, 467, 3196, 1987, 748, 3901, 3631, 3058, 33, 3981, 2455, 2340, 1463, 1648, 3869, 278, 2657, 1226, 1157, 3180, 4149, 442, 2682, 980, 2580, 3019, 1746, 3764, 1940, 2045, 3843, 1242, 2728, 4157, 3702, 451, 3772, 2058, 4100, 3450, 2267, 1090, 2640, 978, 2344, 206, 683, 1858, 4048, 1864, 2027, 3974, 3248, 3155, 3979, 2448, 3573, 228, 483, 3855, 3604, 1102, 2532, 2591, 2770, 2147, 3324, 2112, 3620, 468, 2375, 694, 1340, 3126, 946, 1731, 2562, 1601, 1224, 1613, 381, 3424, 4173, 390, 3986, 3334, 2197, 1416, 3017, 955, 392, 1775, 268, 1895, 1031, 497, 3921, 2464, 1640, 1349, 2690, 4131, 4073, 2298, 3234, 2327, 427, 2570, 1595, 1398, 204, 1140, 1750, 563, 3046, 3488, 258, 2122, 792, 1725, 1579, 4004, 1346, 2505, 3692, 181, 3799, 2840, 1310, 2848, 4017, 4106, 632, 2432, 4014, 3384, 2669, 616, 1830, 3182, 1212, 1323, 1840, 4026 |
| OY6 | 1191, 3616, 3239, 3816, 3307, 1370, 3471, 3078, 3807, 3345, 4075, 1909, 1469, 665, 3243, 236, 2151, 2086, 3656, 2895, 2699, 226, 1757, 3580, 1315, 192, 1821, 2053, 4016, 2276, 1068, 382, 582, 263, 2984, 1322, 133, 1088, 2894, 118, 2778, 1834, 1793, 720, 248, 1508, 804, 2870, 1369, 2496, 3451, 716, 493, 782, 1946, 2400, 1200, 2456, 110, 2932, 3588, 2945, 3028, 926, 3888, 950, 2538, 3846, 406, 292, 3615, 755, 714, 1794, 2767, 3492, 914, 1798, 756, 2167, 2587, 3312, 1319, 2109, 402, 2941, 3162, 2626, 2235, 1327, 3325, 51, 737, 474, 3323, 3441, 654, 1161, 917, 146, 3136, 4072, 3119, 2902, 3550, 2137, 1445, 3295, 3352, 3660, 2462, 478, 297, 2441, 1672, 703, 3937, 1213, 1291, 275, 1135, 2018, 3204, 1324, 2010, 1148, 527, 1138, 2420, 1703, 1096, 508, 326, 1556, 1596, 1614, 558, 746, 1332, 3086, 2254, 1170, 2417, 3089, 1452, 3083, 1387, 3784, 4133, 2964, 1477, 2019, 462, 1514, 457, 2823, 2046, 2549, 3773, 4069, 3433, 4067, 3194, 35, 1048, 2488, 2161, 267, 3421, 3063, 4094, 4085, 1984, 3170, 1644, 1992, 517, 2319, 315, 3175, 2592, 15, 704, 4162, 1960, 2864, 260, 2997, 4022, 3877, 3439, 78, 3853, 2741, 3765, 2085, 2981, 3429, 1257, 318, 2736, 3178, 3415, 3095, 1292, 3851, 2256, 2370, 2221, 1504, 1575, 2756, 1716, 2512, 220, 123, 779, 1653, 3480, 2960, 2716, 2899, 940, 466, 3079, 2662, 3157, 1662, 2821, 2324, 1891, 2927, 3504, 1074, 577, 3908, 3850, 4080, 870, 1214, 2659, 2481, 3163, 691, 2656, 3181, 2839, 879, 1828, 1951, 1391, 209, 2975, 2503, 2159, 3696 |
| OY7 | 1225, 68, 509, 3904, 1472, 651, 3210, 249, 1296, 2442, 3577, 3968, 1766, 3777, 1054, 4049, 2834, 1079, 313, 4041, 3242, 3503, 1912, 1053, 2374, 187, 2408, 205, 1719, 2996, 2032, 1085, 3610, 58, 1604, 484, 677, 3609, 2880, 717, 3929, 2777, 3062, 1194, 1134, 28, 3917, 872, 3735, 3195, 858, 833, 1676, 3231, 4066, 2153, |

TABLE 2-continued

| Mixing Pool and Corresponding Clone Numbers contained therein | |
|---|---|
| | 1294, 1250, 4146, 2801, 4050, 3600, 2024, 2764, 4047, 1546, 2775, 2597, 1841, 2143, 439, 1251, 2956, 1265, 3485, 2215, 50, 3139, 3900, 3671, 3121, 7, 1018, 957, 128, 4177, 1935, 592, 1758, 557, 2827, 3265, 1095, 597, 1462, 1567, 3808, 3466, 981, 1056, 2697, 3467, 1303, 158, 793, 1867, 63, 1171, 1754, 3523, 2218, 1350, 3296, 1808, 3269, 1160, 3474, 1019, 3148, 1116, 1517, 2088, 2335, 3502, 1513, 1903, 2069, 3263, 3004, 2382, 1600, 1571, 80, 1968, 713, 1870, 3326, 1738, 3001, 725, 2348, 1784, 1815, 2709, 3116, 177, 19, 3189, 2539, 2103, 3670, 3252, 3652, 905, 2599, 4065, 435, 623, 288, 3251, 2494, 2627, 3230, 4058, 396, 2006, 1623, 1415, 174, 1873, 1325, 3655, 2534, 3768, 3478, 4078, 1669, 2803, 3519, 141, 1893, 2540, 1620, 2664, 2325, 3304, 3445, 2987, 622, 1111, 2368, 2837, 3513, 1002, 230, 283, 697, 678, 3997, 2737, 3420, 3443, 1789, 2445, 1971, 791, 3606, 2543, 3809, 1527, 1269, 2225, 1722, 3712, 3560, 2011, 3691, 3522, 2571, 2903, 3762, 504, 2622, 2162, 302, 1741, 426, 3882, 1874, 1392, 515, 2768, 2366, 544, 1110, 2346, 1887, 2544, 3896, 1206, 514, 3389, 452, 1923, 2748, 3537, 1683, 3629, 3617, 2793, 1450, 1120, 1017, 1547, 1791, 973 |
| OY8 | 41, 2730, 3837, 358, 3021, 2263, 794, 501, 535, 1338, 778, 1103, 1238, 4064, 943, 1799, 546, 3365, 2634, 3999, 199, 3012, 1040, 18, 1433, 3961, 3109, 9, 3279, 744, 3341, 2614, 3524, 2316, 3154, 3707, 2590, 3879, 2974, 3346, 2096, 3632, 2219, 2917, 3313, 536, 3468, 1861, 3306, 440, 488, 2677, 4111, 580, 881, 987, 1732, 1195, 1361, 2300, 2843, 3793, 1009, 1701, 2710, 3039, 2361, 355, 2642, 3589, 3186, 2612, 1389, 1316, 339, 3532, 3257, 3496, 1039, 2782, 1638, 2469, 1706, 4068, 3694, 117, 3260, 2648, 1735, 75, 3410, 157, 3041, 2830, 446, 120, 3693, 2973, 2425, 3664, 997, 1639, 2311, 3102, 3972, 1210, 3820, 2930, 2124, 3406, 23, 1708, 1907, 2955, 522, 1715, 1437, 1165, 1258, 1027, 1052, 613, 162, 67, 2229, 1627, 3555, 500, 682, 686, 767, 3729, 2192, 306, 1005, 2583, 1804, 4033, 3477, 1302, 3567, 3436, 2694, 2406, 385, 2794, 727, 1958, 883, 3802, 2039, 3527, 1500, 3301, 1320, 285, 3054, 2294, 2501, 3969, 161, 3013, 2983, 594, 1062, 1293, 1616, 2295, 1990, 1032, 3258, 615, 3864, 1431, 1118, 3160, 1400, 3771, 1876, 3829, 693, 640, 1152, 2163, 3361, 2545, 3596, 3787, 2528, 2858, 3745, 4045, 1520, 3782, 3134, 3287, 3179, 3235, 372, 2600, 74, 2937, 3926, 2410, 3340, 1879, 251, 2452, 1059, 529, 3226, 1516, 1569, 2913, 1786, 638, 1014, 142, 1139, 429, 3047, 1107, 3756, 2757, 184, 2093, 2829, 3048, 579, 2188, 834, 4112, 2246, 856, 2317, 2674, 3077, 2581, 2173, 3329, 1233, 2986, 2947, 3748, 3811, 511, 400, 4018, 1228, 1154, 1193, 2572, 1439, 1542, 4027, 3803 |
| OY9 | 2015, 1203, 1335, 513, 3747, 2465, 347, 235, 1826, 2865, 749, 726, 3499, 803, 1288, 3872, 2645, 1243, 361, 4057, 4129, 789, 843, 2282, 171, 2072, 189, 2671, 922, 3645, 986, 2303, 4000, 329, 3458, 1688, 4092, 389, 1736, 2752, 1355, 3602, 1397, 2007, 2078, 4061, 2862, 1790, 2812, 3991, 539, 215, 938, 2705, 937, 308, 2698, 700, 1230, 4054, 1585, 3460, 2586, 892, 1632, 2040, 799, 2909, 2763, 1959, 247, 2049, 410, 1748, 270, 681, 3564, 3841, 2461, 2944, 1423, 2565, 3556, 915, 1487, 2923, 2734, 2186, 464, 1902, 2393, 962, 2017, 2942, 2482, 441, 1626, 2323, 1963, 1337, 1180, 1007, 2537, 1675, 1711, 1290, 195, 1863, 1025, 2460, 461, 1383, 992, 2262, 2789, 2845, 127, 927, 182, 1727, 3505, 2169, 1347, 2958, 3442, 695, 598, 3780, 3332, 3539, 2345, 3786, 3769, 3259, 1295, 2636, 1064, 3407, 336, 1588, 2141, 4169, 3281, 1239, 295, 1150, 4011, 178, 1796, 2631, 271, 3372, 2625, 998, 3423, 1618, 975, 2386, 1545, 3448, 1975, 2603, 354, 891, 1660, 820, 2443, 1911, 783, 2486, 3145, 2849, 304, 3525, 3526, 3367, 4136, 3127, 3320, 1753, 3447, 2509, 4071, 919, 1605, 3668, 1478, 3971, 254, 172, 3993, 3517, 3130, 2023, 1982, 1906, 3980, 200, 2611, 144, 3964, 2644, 2237, 662, 16, 2172, 3343, 2217, 3368, 2230, 3060, 838, 607, 2618, 1245, 1785, 1345, 1752, 634, 2632, 2905, 2207, 603, 436, 1308, 1429, 76, 3223, 1289, 2755, 2181, 3512, 2492, 2278, 2422, 1629, 3305, 1557, 322, 2832, 1158, 575, 3465, 1641, 312, 2476, 1970, 3715, 1020, 1707, 2833, 1509, 224, 4153, 3909, 3923 |
| OY10 | 3431, 2281, 1687, 1264, 3051, 3358, 2919, 3392, 2342, 2433, 3582, 1643, 1877, 2242, 2610, 2502, 4010, 198, 2676, 2136, 1329, 2609, 3394, 1999, 642, 646, 3299, 3561, 2421, 2079, 2949, 4091, 1630, 3497, 1190, 391, 3812, 604, 2926, 3376, 1854, 2091, 1985, 2396, 2033, 2898, 61, 751, 3989, 156, 1552, 1179, 802, 1540, 1247, 1989, 1781, 2514, 2419, 2028, 2213, 3734, 710, 3714, 999, 866, 2200, 753, 2280, 3158, 2889, 2277, 3125, 241, 3965, 2553, 2643, 2204, 2198, 4145, 3925, 1201, 1831, 1034, 2890, 1426, 920, 3644, 3337, 2454, 3636, 1978, 1788, 1755, 3657, 1953, 2650, 53, 2564, 1173, 1744, 218, 786, 4090, 1267, 319, 2905, 1162, 4025, 2116, 901, 2950, 2336, 2234, 2260, 2180, 1390, 188, 114, 2971, 1204, 918, 1573, 1617, 2333, 2500, 2140, 1069, 547, 1694, 4020, 1764, 3174, 4154, 277, 1955, 1232, 2574, 1680, 2874, 1252, 1661, 1673, 1837, 1336, 787, 3625, 3942, 3867, 600, 2060, 690, 4082, 1024, 773, 3607, 2164, 454, 2879, 1081, 1765, 1418, 2034, 3957, 3563, 338, 3219, 3611, 2980, 2253, 66, 3024, 1658, 40, 3183, 2468, 201, 1910, 29, 1408, 3586, 320, 1351, 3549, 1624, 98, 2411, 2110, 3200, 2231, 351, 3640, 933, 1587, 1482, 752, 3331, 1010, 1384, 644, 3806, 257, 3770, 2989, 470, 1598, 942, 541, 889, 2087, 772, 1026, 2385, 1378, 3255, 2472, 2624, 362, 202, 3794, 2667, 3444, 485, 1117, 1878, 1198, 2001, 824, 1422, 1285, 168, 1396, 1119, 729, 2315, 3187, 1065, 660, 196, 2201, 2675, 3776, 4130, 4134, 3057, 1751, 4031, 3529, 1936, 3509, 3002, 2035, 465, 1850, 2575, 4110 |
| OY11 | 2314, 414, 2364, 3267, 3858, 1188, 2275, 3963, 1496, 3099, 3859, 190, 764, 36, 3446, 223, 904, 1654, 585, 850, 377, 1948, 2621, 2402, 2238, 3084, 1521, 2969, 1814, 2525, 3791, 567, 1803, 1436, 3718, 2914, 3290, 2531, 2121, 923, 266, 653, 519, 776, 2430, 2268, 3422, 2701, 99, 1886, 2867, 1820, 3314, 2568, 4029, 1539, 675, 1410, 637, 1581, 3283, 2806, 502, 3730, 2957, 1202, 298, 1470, 4116, 2724, 3080, 1805, 718, 1449, 3363, 3339, 3860, 214, 3674, 1922, 983, 2810, 3742, 969, |

TABLE 2-continued

| Mixing Pool and Corresponding Clone Numbers contained therein | |
|---|---|
| | 1674, 332, 3546, 3687, 1151, 3369, 3630, 3430, 2304, 3151, 460, 2828, 524, 1979, 3618, 1933, 112, 4093, 1003, 2205, 959, 2929, 3216, 3149, 505, 3700, 154, 3719, 3863, 2427, 1167, 2273, 913, 1656, 966, 769, 160, 2392, 91, 3014, 1572, 1353, 1919, 930, 1394, 1759, 3572, 1896, 835, 1352, 210, 2939, 3576, 2552, 2779, 60, 496, 1268, 531, 3453, 2126, 2387, 1657, 3409, 3385, 1899, 668, 2558, 3958, 3379, 1046, 1956, 1810, 1512, 2118, 2052, 1089, 2302, 848, 3688, 2487, 56, 2477, 2135, 1532, 3643, 2054, 906, 1843, 1001, 1488, 1554, 2378, 2247, 1377, 300, 3112, 1042, 3292, 1057, 3308, 1458, 1670, 4155, 3061, 2227, 3249, 2750, 636, 3881, 1459, 404, 555, 4023, 3518, 2732, 1115, 3603, 1455, 1851, 341, 1712, 2959, 360, 3899, 3805, 530, 343, 742, 1208, 2721, 1651, 739, 2343, 902, 1938, 2912, 1901, 1393, 3936, 3452, 3515, 3481, 3256, 532, 2111, 2407, 3068, 1817, 352, 1473, 1506, 503, 3168, 3387, 797, 2510, 2480, 1051, 431, 2020, 3272, 2842, 1811, 2762, 447, 327, 293, 3100, 3377, 995, 3233 |
| OY12 | 1278, 583, 3418, 3209, 2491, 145, 3000, 1769, 3983, 3749, 2519, 939, 2855, 3273, 1365, 3425, 1209, 1969, 2579, 2766, 2573, 3050, 1980, 4013, 101, 2269, 2082, 3508, 4030, 2826, 2166, 1313, 1166, 3982, 2623, 3720, 3479, 1454, 3637, 1486, 2679, 836, 2059, 2165, 3193, 1756, 1122, 2308, 2653, 1108, 706, 3228, 3920, 449, 3552, 897, 12, 3775, 537, 3910, 1100, 1884, 3199, 2695, 2293, 1809, 1, 2887, 20, 4098, 2199, 628, 3201, 1983, 559, 1326, 832, 2107, 3493, 1730, 854, 3733, 550, 245, 299, 4168, 4170, 350, 523, 3757, 45, 2781, 2965, 2863, 3435, 3804, 3990, 301, 303, 1236, 369, 1568, 3601, 722, 645, 2029, 363, 1112, 3280, 1181, 1036, 3005, 1511, 2922, 3397, 444, 996, 847, 1272, 1366, 179, 364, 1084, 2985, 2131, 2976, 3751, 652, 564, 4015, 2395, 1859, 853, 3970, 952, 2394, 213, 796, 2979, 4165, 1022, 3907, 2175, 3545, 2593, 3659, 1444, 1611, 1495, 84, 2680, 2444, 3020, 1634, 2683, 565, 2749, 1728, 852, 399, 1343, 961, 3317, 1892, 818, 309, 2982, 1739, 3839, 3022, 1773, 3553, 2026, 2805, 2953, 3646, 2663, 2700, 2191, 2050, 2352, 3587, 3952, 4074, 4055, 3220, 666, 1425, 692, 153, 3375, 1156, 3092, 2638, 108, 2134, 2856, 554, 2719, 1838, 261, 1576, 2176, 1929, 1625, 3740, 3396, 26, 3623, 1553, 3892, 3891, 2831, 1726, 498, 2463, 3370, 3065, 1281, 1845, 1097, 3534, 1182, 3579, 1037, 3417, 2813, 669, 2901, 2608, 1127, 2970, 2717, 4038, 37, 734, 723, 754, 3704, 2043, 1348, 3076, 2556, 3995, 3118, 3845, 863, 1189, 212, 590, 2783, 1136, 3391, 3096, 3321, 3779 |
| OY13 | 3894, 1763, 823, 4127, 2936, 2265, 482, 1852, 964, 1261, 1829, 798, 2988, 1918, 3015, 2535, 2745, 3278, 3792, 134, 1063, 1176, 3016, 237, 876, 761, 2769, 2174, 1869, 2497, 3902, 851, 1942, 2878, 2223, 3710, 3074, 3598, 175, 2067, 506, 1594, 3721, 359, 411, 2216, 1494, 3184, 574, 611, 3516, 2483, 2696, 152, 219, 1438, 3197, 3472, 113, 4087, 1541, 1583, 766, 871, 2095, 1424, 3052, 1515, 194, 4158, 3464, 4003, 1518, 1602, 3366, 929, 4124, 1930, 899, 2647, 3129, 2064, 2318, 715, 1467, 1774, 1894, 841, 1106, 1819, 2447, 3960, 3731, 2704, 3362, 1671, 2428, 3227, 3202, 958, 106, 2884, 31, 826, 3146, 1855, 197, 3736, 2363, 495, 2569, 822, 1223, 1952, 2852, 3456, 589, 2160, 3142, 1248, 2670, 1684, 3951, 1253, 4141, 27, 2635, 829, 2740, 3049, 670, 3767, 2383, 3459, 2128, 2453, 3106, 758, 1446, 2132, 3594, 2042, 1047, 1783, 2691, 2083, 2326, 225, 1898, 1842, 2194, 941, 828, 2616, 2090, 1205, 2940, 1404, 3364, 3998, 3883, 520, 73, 3120, 2628, 4140, 712, 3642, 2372, 2362, 486, 3605, 1000, 376, 1367, 2478, 2508, 1967, 3966, 945, 1480, 119, 1493, 1779, 1609, 4002, 135, 2373, 795, 2429, 3758, 2885, 709, 1430, 1988, 3898, 1330, 1682, 3101, 2397, 1399, 846, 643, 344, 1196, 4147, 1312, 1742, 844, 2436, 2515, 707, 125, 3356, 3570, 2990, 2055, 1529, 3064, 676, 417, 2818, 256, 2467, 437, 1914, 991, 2071, 989, 2291, 1460, 860, 453, 2876, 2279, 2906, 1880, 591, 126, 760, 3143, 186, 3916, 534, 1441, 487, 149, 279, 409, 2620, 2655, 39, 510, 2561, 3928, 415 |
| OY14 | 1663, 3778, 3153, 2851, 658, 3036, 2934, 2097, 2746, 2908, 3684, 1920, 345, 3732, 1943, 1075, 3866, 1474, 2063, 3097, 3862, 595, 3300, 1883, 830, 4179, 2479, 353, 491, 274, 2384, 2012, 3870, 1928, 747, 2961, 1419, 3728, 1328, 221, 2222, 3342, 475, 5, 2092, 2003, 4063, 1124, 4008, 1519, 413, 3268, 3335, 781, 1612, 2130, 815, 30, 1822, 3094, 1550, 581, 3746, 2935, 3266, 2127, 862, 1800, 3654, 2031, 1130, 330, 2228, 3927, 1740, 1083, 3800, 1776, 2184, 3347, 1566, 2038, 1440, 416, 469, 1028, 366, 1402, 2244, 2702, 3940, 1301, 3152, 2004, 765, 2911, 1704, 2733, 2202, 2251, 2002, 3029, 2426, 1772, 2521, 2328, 2924, 388, 3088, 2560, 473, 2356, 608, 1868, 560, 102, 1235, 2233, 3167, 3336, 1461, 1385, 103, 612, 2495, 2415, 1666, 4142, 2785, 2290, 976, 2607, 3081, 1447, 3886, 3992, 2799, 1972, 2203, 2489, 2399, 242, 3635, 3634, 2157, 397, 3327, 1533, 4099, 1700, 3959, 3043, 1562, 2105, 963, 3, 4053, 328, 770, 1724, 1055, 2236, 3738, 21, 657, 610, 2513, 3432, 1466, 3785, 2808, 1030, 1965, 2220, 2089, 1149, 2418, 1186, 1548, 1356, 3717, 3380, 3093, 1628, 1606, 2668, 1560, 2466, 1771, 3826, 988, 272, 1234, 1060, 3082, 1565, 25, 619, 3641, 1875, 4105, 2331, 878, 3763, 2872, 960, 1297, 1762, 2605, 1141, 1067, 2357, 861, 3090, 2972, 3192, 2431, 2715, 3726, 2139, 4118, 386, 373, 4005, 540, 3675, 3878, 1276, 2245, 405, 688, 1941, 229, 2321, 2301, 2322, 2602, 1395, 1490, 88, 3884, 733, 516, 1386, 62, 14, 1977, 2030, 2529, 2978, 1767, 147, 4046, 1780, 2062, 2021 |
| OY15 | 1950, 837, 1995, 4062, 1073, 455, 2450, 325, 1249, 371, 3922, 92, 935, 3032, 3026, 208, 4171, 1137, 1044, 1599, 1597, 1734, 3351, 2044, 886, 731, 3506, 1104, 3893, 4176, 1649, 3875, 1904, 1259, 1092, 1131, 1961, 116, 1240, 2389, 518, 1954, 3705, 3827, 1996, 1174, 203, 648, 1199, 1908, 492, 4095, 2283, 1714, 3842, 759, 3115, 1334, 627, 1381, 3070, 1380, 1244, 2542, 1468, 990, 1185, 3943, 2548, 2920, 3113, 1637, 4084, 2013, 3817, 3309, 3254, 3075, 2566, 3681, 3144, 3667, 2106, 1962, 3067, 2999, 1497, 831, 741, 89, 2672, 165, 97, 1652, 2824, 624, 255, 2658, 1944, 1991, 3593, 2904, 3754, 2841, 526, 1113, 438, 2853, 2918, 3293, 2861, 3568, 3222, |

TABLE 2-continued

Mixing Pool and Corresponding Clone Numbers contained therein

|     |     |
| --- | --- |
|     | 855, 1485, 3988, 2154, 3217, 552, 2457, 2257, 566, 115, 1693, 3682, 809, 2446, 2313, 216, 2951, 121, 3574, 3303, 3559, 1277, 3150, 1993, 970, 3008, 1900, 4, 1411, 1677, 3583, 3569, 2747, 3831, 24, 2760, 383, 2786, 3344, 1503, 1216, 2113, 1592, 370, 2241, 3797, 907, 1721, 2014, 1713, 1260, 2915, 3122, 3282, 1262, 4115, 3665, 2289, 3271, 3849, 699, 807, 3542, 3703, 281, 840, 83, 3930, 2206, 3709, 1360, 1806, 533, 2292, 2286, 2546, 2881, 2857, 163, 602, 570, 3241, 1689, 3836, 3766, 3987, 2991, 2765, 2272, 2758, 1406, 2582, 1013, 909, 586, 928, 571, 2967, 685, 2595, 2076, 3662, 2798, 1934, 1373, 3833, 882, 2351, 974, 3865, 3711, 3274, 3533, 1263, 1664, 4144, 1427, 635, 2714, 3476, 1610, 601, 1076, 375, 2506, 1531, 3213, 1311, 424, 1481, 1702, 3031, 3245, 2299, 3723, 3395, 3354, 276, 3744, 394, 2498, 4148, 3932 |
| OZ0 | 1225, 1191, 3294, 2073, 378, 2652, 1950, 1663, 3894, 1278, 2314, 3431, 2015, 41, 244, 2066, 2086, 808, 763, 3205, 1926, 1137, 1474, 3278, 1969, 1654, 198, 1243, 3365, 1306, 3044, 1079, 2152, 2355, 2424, 166, 1092, 747, 2223, 2623, 3718, 1190, 3458, 3154, 2398, 2099, 1604, 2984, 1997, 1187, 2359, 4095, 3268, 2483, 3228, 1820, 1179, 215, 2677, 3056, 768, 833, 716, 1270, 2846, 4097, 2548, 3654, 194, 20, 4116, 2280, 2763, 2642, 2946, 140, 1841, 406, 934, 2550, 1164, 2999, 1028, 1774, 4168, 332, 1426, 2923, 117, 211, 3461, 4177, 2941, 2522, 294, 1371, 3754, 2426, 31, 3601, 1003, 786, 2537, 2311, 269, 3528, 1303, 3119, 2305, 4052, 1872, 679, 3336, 1248, 1366, 769, 2971, 1727, 1027, 2594, 1359, 1116, 275, 3058, 661, 2993, 2369, 2457, 3106, 213, 3576, 1232, 1064, 1804, 2518, 2809, 3326, 558, 2580, 1937, 1824, 1401, 1993, 2799, 1634, 3379, 1024, 998, 3301, 903, 1004, 905, 1514, 1090, 925, 2954, 2047, 1216, 2105, 2616, 2054, 66, 3145, 3258, 924, 3229, 1325, 4094, 483, 3473, 1305, 3581, 2289, 2808, 486, 1773, 2110, 3971, 3787, 2285, 3330, 2987, 2997, 1731, 3613, 3621, 805, 2286, 2466, 2373, 1425, 4155, 16, 3340, 1528, 3725, 1971, 1292, 268, 3381, 1341, 3286, 2582, 2872, 1196, 1625, 341, 470, 1107, 111, 736, 504, 2899, 1398, 1580, 3408, 2718, 974, 386, 2818, 3534, 1901, 3444, 2207, 321, 728, 3896, 870, 3799, 667, 4160, 17, 1531, 1490, 126, 3704, 3387, 196, 322, 2173, 1428, 973, 3696, 4026, 2533, 859, 3648, 3932, 2021, 415, 3779, 3233, 4110, 3923, 3803, 1981 |
| OZ1 | 2151, 3597, 3333, 774, 1172, 4171, 3866, 2745, 1209, 904, 4010, 2645, 546, 2350, 3285, 2834, 3810, 3224, 1146, 65, 1259, 1928, 2878, 3982, 1436, 3497, 329, 2316, 481, 280, 58, 263, 2711, 2284, 1743, 492, 413, 3516, 706, 2867, 1552, 539, 488, 4143, 420, 858, 3451, 1012, 3147, 3947, 3943, 1800, 1515, 2887, 1470, 753, 2909, 355, 1407, 3138, 2597, 3846, 342, 2195, 3647, 3067, 469, 1467, 299, 1674, 2890, 1487, 3694, 3390, 1363, 128, 402, 2943, 4120, 743, 2904, 3029, 2884, 1568, 4093, 218, 1007, 1639, 3206, 849, 3467, 4072, 912, 1344, 252, 2334, 3167, 3142, 1272, 966, 114, 182, 1258, 2150, 253, 3148, 1291, 3631, 477, 3868, 3622, 552, 2453, 2394, 2939, 1955, 2636, 2583, 2589, 2995, 1870, 1614, 980, 4077, 985, 148, 3150, 3992, 3020, 3958, 4082, 2625, 1500, 3697, 4178, 3652, 462, 2267, 605, 3322, 1246, 1503, 1562, 828, 3643, 2253, 2486, 1032, 2068, 3454, 1873, 3063, 228, 3954, 1177, 545, 3665, 3785, 2362, 3022, 2411, 1478, 3596, 3470, 1309, 3445, 260, 946, 908, 1217, 107, 2292, 1560, 135, 666, 1670, 662, 2410, 1642, 890, 2445, 3095, 1775, 1692, 4164, 3023, 1406, 3763, 344, 1929, 1851, 2989, 3047, 639, 1729, 3762, 2716, 1595, 3128, 3624, 3156, 2351, 4118, 417, 1097, 2912, 2667, 2905, 680, 2804, 2544, 4080, 181, 1650, 512, 1945, 2506, 1395, 591, 754, 3168, 660, 1557, 2581, 3487, 1791, 2159, 1840, 2224, 1043, 2886, 4148, 2062, 3928, 3321, 995, 2575, 3909, 4027, 2792, 4049, 236, 2817, 3355, 334, 2084, 208, 1075, 2535, 3425, 223, 2502, 3872, 1799, 2891, 3091 |
| OZ2 | 44, 1476, 2907, 1973, 1904, 3870, 1942, 1166, 1803, 1630, 4000, 3524, 3945, 3795, 3610, 582, 286, 3558, 1298, 1908, 1519, 611, 1108, 1886, 156, 3991, 440, 1114, 1915, 3195, 2496, 1705, 1372, 32, 1185, 862, 3052, 1, 298, 2200, 799, 2361, 2952, 287, 2775, 2538, 2048, 1795, 931, 1962, 416, 715, 245, 969, 1034, 915, 4068, 393, 867, 957, 2109, 1885, 234, 2119, 3593, 2002, 106, 369, 112, 1744, 1180, 997, 1622, 4059, 2697, 3136, 3475, 528, 3378, 1178, 2233, 2160, 847, 1656, 188, 927, 1165, 3830, 3137, 1019, 1213, 3901, 671, 3319, 2144, 3217, 2128, 952, 210, 277, 1295, 1005, 3203, 2458, 713, 1596, 2682, 2287, 3666, 109, 1277, 3886, 2444, 2558, 690, 3372, 3527, 4122, 1099, 3252, 2019, 3450, 2380, 3976, 816, 3344, 3043, 941, 1532, 2980, 783, 1990, 3562, 1077, 174, 3421, 3573, 698, 2883, 569, 4115, 1466, 2372, 3839, 98, 3668, 2545, 4021, 1535, 3304, 2864, 3126, 2297, 3315, 888, 533, 2668, 4002, 3220, 1458, 2237, 3926, 2713, 2255, 1789, 3415, 392, 1222, 170, 2226, 2758, 878, 643, 2176, 1455, 3770, 429, 705, 1098, 2903, 2960, 2570, 4103, 2146, 2438, 882, 2139, 676, 1845, 1938, 3794, 2632, 845, 3813, 1887, 3850, 3692, 3006, 2101, 3383, 375, 2602, 1880, 723, 503, 1065, 3305, 3077, 82, 1547, 2503, 1323, 525, 3038, 2948, 2498, 1780, 2561, 3096, 3377, 1850, 4153, 1542, 1921, 1054, 3243, 641, 806, 403, 4036, 3026, 1943, 3015, 1365, 3446, 2610, 1288, 943, 311, 3663, 382, 3105, 3716, 3814, 562, 3875, 2012, 851, 1313, 567, 4091, 2303, 2614, 3403, 3253, 1085 |
| OZ3 | 3661, 2080, 367, 1199, 4008, 574, 2653, 99, 3989, 2812, 3306, 3801, 2588, 3735, 1369, 2507, 356, 911, 990, 2127, 1424, 1809, 1202, 866, 2040, 3039, 3815, 800, 1546, 950, 1505, 4121, 3510, 2106, 1440, 2318, 550, 3742, 1831, 3556, 1706, 2475, 1231, 1018, 1319, 932, 1659, 2925, 1991, 2251, 958, 1236, 1933, 1173, 1337, 3664, 936, 1668, 1056, 146, 3328, 1856, 2409, 3284, 1235, 589, 996, 913, 1390, 127, 1437, 3437, 1717, 3474, 3937, 748, 3270, 2619, 490, 2154, 3459, 3970, 1352, 4154, 3259, 306, 625, 811, 1968, 1556, 442, 664, 3161, 839, 3559, 1447, 2680, 668, 2060, 271, 2039, 2844, 4102, 3670, 1477, 4100, 3310, 3973, 3948, 2786, 3959, 2194, 2135, 3611, 1911, 2295, 324, 1502, 1415, 267, 2448, 1008, 3686, 3419, 1262, 3432, 3642, 1739, 1624, 1605, 3361, 857, 921, 2325, 1960, 1340, 3724, 994, 130, 1806, |

TABLE 2-continued

| Mixing Pool and Corresponding Clone Numbers contained therein | |
|---|---|
| | 1606, 1609, 4055, 3308, 2644, 2937, 59, 2601, 3443, 3178, 955, 3215, 3240, 1412, 2272, 2331, 846, 1576, 3603, 257, 1139, 3190, 885, 2571, 3480, 427, 1058, 3114, 2057, 3833, 3726, 3064, 1281, 902, 202, 634, 3873, 1607, 2346, 3908, 2505, 1866, 1549, 2617, 1076, 2322, 2906, 734, 1506, 3187, 1629, 2674, 1559, 1017, 2975, 1212, 2075, 2928, 8, 394, 4046, 510, 3391, 3100, 465, 224, 1439, 472, 3777, 665, 780, 3844, 3919, 1038, 3032, 3732, 1918, 3273, 36, 2242, 803, 4064, 631, 3761, 1068, 813, 3350, 3172, 1507, 1649, 2384, 3902, 2166, 3791, 2949, 986, 3341, 2312, 2646, 2032, 2125, 606, 1417, 2584, 648, 1124, 3184, 2308, 2701, 751, 1790, 1861, 3011, 4042, 872, 2870 |
| OZ4 | 1362, 869, 1468, 3266, 2095, 2293, 2957, 999, 1632, 2710, 877, 2860, 4047, 3888, 3584, 2240, 1974, 3667, 2038, 2064, 3733, 2810, 1201, 2565, 2469, 3066, 1374, 7, 3312, 956, 1126, 1492, 1944, 2202, 3202, 303, 3618, 2564, 1963, 2425, 57, 896, 981, 917, 2259, 629, 3169, 2390, 102, 3456, 444, 2273, 2180, 2845, 1715, 3619, 814, 1160, 703, 1987, 1699, 176, 3595, 3988, 2383, 853, 835, 3174, 3769, 2192, 1078, 1339, 80, 326, 4149, 2639, 599, 3823, 3303, 3081, 84, 1899, 600, 2631, 3802, 2117, 1813, 2103, 2964, 2058, 2772, 86, 289, 383, 1700, 1842, 2477, 3219, 2443, 1616, 687, 1484, 1623, 2161, 3979, 3590, 3798, 771, 3282, 2513, 712, 2982, 3549, 919, 2163, 3871, 3551, 2664, 4162, 694, 2651, 3298, 3055, 1360, 1628, 1779, 4074, 1057, 3964, 74, 2404, 2434, 3420, 2736, 3017, 2598, 3938, 412, 2765, 4105, 1399, 261, 1115, 3806, 142, 476, 3037, 3522, 1653, 2327, 459, 1924, 1284, 1373, 2715, 1529, 3065, 2343, 362, 1752, 3653, 2094, 1110, 577, 1346, 4119, 1636, 979, 601, 2301, 2279, 37, 1473, 2315, 2422, 2317, 2673, 1120, 209, 3182, 3638, 1633, 3536, 3744, 147, 39, 1136, 293, 2035, 1509, 2572, 2963, 1766, 1469, 3547, 1927, 1836, 1846, 935, 345, 2988, 2855, 764, 1877, 3499, 1238, 1456, 3171, 2276, 1300, 2791, 3411, 4088, 4176, 274, 2497, 2826, 2525, 2079, 3645, 744, 2288, 1142, 2996, 3599, 3164, 1050, 10, 203, 4063, 1494, 1122, 3422, 61, 2862, 3468, 3591, 1957, 3917, 804, 701, 2754, 2802, 2542, 2935, 871, 2695, 3730, 3714, 892, 1701, 3398, 3214, 2764, 926, 3669 |
| OZ5 | 122, 3144, 1566, 3129, 854, 983, 3925, 1423, 1638, 3185, 79, 3121, 2587, 2629, 1718, 1498, 2658, 2733, 3227, 301, 1979, 53, 2323, 2973, 1986, 425, 3466, 1161, 240, 3208, 1168, 2678, 560, 2852, 3397, 1167, 2260, 2789, 522, 3018, 407, 3269, 1672, 3196, 2401, 3887, 738, 1485, 3767, 1859, 1896, 1764, 3786, 3729, 659, 3262, 1571, 508, 3180, 1564, 3501, 6, 3574, 2607, 1495, 3385, 3867, 1796, 883, 708, 1510, 2539, 4133, 3772, 1033, 3469, 2511, 2760, 4099, 1898, 56, 338, 820, 1293, 2081, 893, 2006, 2488, 3155, 1491, 3571, 1279, 3122, 610, 4140, 309, 1351, 4071, 1152, 3483, 164, 1620, 704, 2375, 3237, 649, 1591, 3709, 3093, 1493, 3952, 3292, 144, 2600, 4163, 2248, 2737, 318, 1416, 735, 3246, 1094, 2991, 1875, 2397, 1838, 2732, 644, 1014, 3783, 1710, 3691, 779, 3234, 43, 711, 944, 1934, 2431, 2055, 3370, 739, 2624, 1345, 702, 2931, 544, 1074, 4004, 4138, 1183, 2726, 1610, 2321, 2876, 4038, 352, 729, 2278, 856, 463, 1450, 1391, 1830, 2693, 1890, 3796, 276, 1767, 2655, 2783, 327, 3002, 2833, 1193, 1857, 3968, 1909, 2776, 1543, 1590, 227, 92, 1920, 798, 939, 190, 1643, 726, 1103, 971, 810, 4016, 4132, 2516, 2661, 3905, 3893, 491, 1869, 4030, 1814, 2421, 922, 3279, 3108, 1379, 1719, 620, 2214, 1655, 2723, 1174, 2003, 2216, 1756, 2268, 2898, 4061, 536, 947, 1584, 28, 1508, 2835, 4086, 3427, 1244, 3746, 766, 3199, 502, 710, 2586, 1009, 2684, 3247, 2024, 3028, 3416, 1093, 1091, 3681, 3347, 2647, 1730, 1922, 4145, 2944, 2782, 499, 3946, 3671, 2167, 85, 1848 |
| OZ6 | 255, 1704, 2428, 3990, 524, 2650, 1626, 3693, 2735, 1184, 3808, 654, 3996, 2578, 423, 2261, 1868, 1952, 2922, 2427, 2234, 2262, 2955, 2100, 1770, 1808, 2441, 467, 3683, 3486, 2649, 855, 670, 2395, 3572, 4020, 2345, 767, 2077, 2551, 1600, 1096, 1157, 1782, 2274, 1070, 121, 976, 1611, 3409, 3942, 178, 1958, 1761, 1916, 3189, 3784, 451, 3288, 365, 1197, 24, 1533, 225, 2487, 3563, 1660, 1062, 1287, 2687, 396, 1048, 3248, 873, 4009, 4076, 2915, 657, 2628, 818, 320, 2509, 640, 1589, 314, 2540, 15, 468, 673, 284, 1646, 2206, 3380, 119, 3587, 1042, 2611, 372, 1453, 1913, 3997, 1257, 2197, 1219, 977, 2596, 3987, 3641, 3101, 2719, 3518, 1384, 638, 1939, 3538, 2011, 123, 2298, 894, 2264, 2900, 2798, 3192, 2990, 2463, 1651, 2472, 1785, 2296, 282, 2366, 3504, 1579, 233, 2577, 2729, 3476, 229, 453, 2717, 1817, 1119, 2492, 2246, 2243, 2793, 1951, 616, 2731, 1237, 2156, 3354, 2978, 2620, 590, 447, 3509, 1707, 1154, 953, 3577, 4075, 3639, 1133, 825, 418, 3922, 3684, 1829, 2519, 3859, 3582, 749, 778, 2873, 1998, 2053, 480, 2061, 1778, 2707, 1104, 353, 2174, 3508, 2969, 3561, 2671, 9, 335, 1823, 205, 2744, 1280, 3173, 94, 1996, 2092, 411, 3193, 2430, 2033, 2078, 3313, 2414, 136, 1134, 248, 64, 2320, 4151, 1380, 581, 1583, 1884, 2806, 3734, 3460, 3793, 1241, 2992, 3600, 2945, 2405, 3918, 2630, 2566, 2184, 899, 3493, 3674, 2198, 2461, 1039, 3832, 3854, 3900, 756, 1275, 4128, 2998, 624, 2911, 1671, 3804, 2828, 1953, 441, 120, 3557, 2416, 1567, 3441, 1215, 4166, 2892 |
| OZ7 | 608, 1223, 1511, 3863, 2336, 992, 1907, 291, 2065, 3296, 297, 4079, 1413, 445, 401, 3222, 3049, 4015, 1759, 1694, 3539, 686, 3931, 2037, 2382, 1703, 1226, 2388, 3967, 3399, 2951, 2290, 1444, 1657, 3625, 4011, 727, 588, 3371, 19, 1387, 3702, 3790, 2897, 2787, 3831, 3327, 2326, 3688, 3957, 891, 594, 2354, 2210, 4058, 35, 3974, 3085, 3885, 821, 1260, 21, 3120, 1892, 3586, 3447, 693, 139, 1432, 1893, 2592, 3620, 3565, 2177, 2212, 3930, 3717, 1480, 2352, 3112, 200, 3235, 4019, 2179, 678, 3429, 3334, 131, 3053, 2114, 3766, 619, 1682, 554, 4023, 1010, 1786, 1897, 4012, 3560, 220, 4073, 553, 2377, 2751, 3662, 2972, 3570, 498, 2721, 3255, 1245, 3713, 2307, 2768, 2927, 1725, 4006, 1574, 1647, 2714, 1941, 860, 2970, 3068, 1396, 3512, 4112, 1797, 3617, 1828, 2669, 2706, 655, 2193, 3395, 2529, 409, 212, 2762, 1936, 1020, 1228, 2171, 2442, 3345, 2367, 238, 1839, 3494, 371, 2908, 1261, 3749, 3099, 2433, 2865, 1338, 173, 618, 1821, 70, 2771, 1925, 1376, 3506, |

TABLE 2-continued

Mixing Pool and Corresponding Clone Numbers contained therein

|   |   |
|---|---|
|  | 2479, 2769, 2082, 1521, 3299, 189, 3109, 1457, 2022, 2408, 630, 4032, 2555, 3045, 3827, 5, 359, 2165, 776, 2396, 2007, 2917, 1029, 880, 1194, 720, 1745, 346, 2439, 3070, 1550, 1541, 1100, 3283, 2213, 1585, 2843, 3890, 895, 4050, 3588, 2814, 2790, 916, 3075, 1776, 1930, 2107, 214, 2204, 3841, 3496, 3628, 621, 3139, 1798, 1227, 1835, 2916, 2824, 765, 3362, 3435, 460, 3657, 2482, 446, 87, 3133, 1462, 3323, 875, 1375, 489, 3568, 2356, 822, 3005, 3719, 2950, 1383, 1708, 3402, 143, 1350, 478, 2189, 2686, 2727, 3949 |
| OZ8 | 2740, 564, 1394, 547, 3332, 682, 614, 1501, 3004, 2420, 2657, 3386, 3500, 3462, 216, 2785, 3659, 2387, 787, 1150, 2794, 887, 3977, 177, 3083, 4157, 421, 2520, 2868, 2747, 397, 2083, 848, 2034, 354, 2983, 724, 2854, 3230, 3194, 2027, 1464, 2451, 2168, 1713, 3738, 73, 3317, 1408, 1753, 3829, 3373, 167, 141, 3175, 2112, 2070, 2517, 745, 83, 1356, 945, 2050, 300, 3980, 3179, 1006, 3103, 697, 2981, 3986, 1720, 1304, 2211, 3836, 25, 1330, 2856, 555, 3331, 2913, 3880, 2360, 3712, 2512, 4131, 48, 3338, 1333, 2076, 3090, 3356, 1726, 1208, 1378, 2618, 3236, 633, 515, 1891, 792, 3706, 2493, 1747, 635, 688, 1460, 1127, 2407, 168, 2181, 834, 1271, 3629, 879, 3384, 2499, 4007, 3455, 3723, 2030, 279, 1189, 1811, 3529, 3715, 4018, 1475, 1296, 3807, 2051, 543, 689, 55, 1249, 2746, 964, 3983, 1496, 2342, 1826, 535, 3040, 3264, 192, 3457, 2893, 868, 1525, 731, 4179, 761, 2269, 3084, 646, 2072, 3961, 2145, 3033, 187, 2585, 827, 3874, 3135, 3705, 475, 3721, 2059, 519, 1985, 1397, 2219, 430, 3955, 3062, 1793, 3232, 2742, 243, 1381, 3094, 4087, 3910, 1581, 2028, 4054, 2300, 596, 3198, 2801, 2932, 4108, 239, 982, 3254, 3800, 4124, 832, 3860, 2643, 3564, 3257, 1849, 2250, 50, 914, 3906, 538, 3685, 1652, 2004, 2704, 2863, 3151, 1755, 2942, 2830, 2882, 1635, 597, 474, 2358, 1667, 2249, 2861, 473, 2569, 1036, 154, 901, 461, 23, 151, 494, 2218, 2462, 2449, 246, 3514, 1608, 4142, 829, 652, 930, 1069, 3780, 500, 433, 2547, 3263, 1138, 278, 1825, 52, 3914, 2313 |
| OZ9 | 2593, 2126, 1336, 295, 385, 250, 740, 3116, 1452, 2728, 561, 2341, 3822, 3569, 2157, 2691, 2302, 1418, 2603, 3013, 1153, 2606, 2627, 4067, 1864, 264, 3009, 4060, 2014, 2236, 520, 961, 29, 3320, 1876, 432, 967, 3519, 315, 3324, 183, 2797, 3098, 840, 1548, 3966, 2191, 1377, 1906, 3287, 3759, 1021, 283, 2085, 390, 2689, 3087, 790, 1689, 1565, 3898, 2134, 404, 752, 1569, 3953, 129, 1722, 1716, 2690, 3034, 3934, 2910, 2595, 861, 125, 2831, 742, 2385, 607, 1593, 305, 1392, 2324, 2122, 2025, 2859, 2633, 1427, 405, 2291, 2608, 2111, 1285, 2755, 2188, 3788, 1683, 2839, 4014, 584, 3626, 69, 2299, 1977, 149, 863, 2842, 4031, 1970, 400, 3935, 249, 3078, 3614, 1266, 3985, 2473, 325, 2097, 1852, 1769, 3963, 3392, 235, 501, 3353, 104, 1315, 2962, 169, 784, 4024, 886, 830, 876, 101, 2238, 642, 171, 1433, 3548, 3123, 2374, 3592, 81, 333, 379, 1954, 3342, 1594, 836, 653, 2091, 3602, 3632, 3426, 650, 2777, 1834, 2133, 2559, 2005, 627, 1822, 113, 537, 637, 2419, 1230, 1361, 3848, 1536, 4146, 110, 1801, 428, 1932, 3309, 1083, 929, 1326, 3339, 2553, 681, 3532, 398, 2712, 2215, 3492, 22, 1586, 2349, 97, 3152, 3731, 2965, 2304, 1788, 2017, 3041, 1125, 1807, 1095, 737, 3072, 222, 3933, 3293, 2560, 495, 1181, 3700, 2116, 2460, 3406, 3507, 4001, 3523, 3660, 3895, 842, 1274, 3520, 1666, 2635, 3751, 1919, 2140, 598, 3555, 1537, 3835, 2069, 527, 3869, 191, 3984, 2330, 2446, 1783, 3545, 3453, 1837, 1239, 2406, 2743, 3828, 2709, 3089, 1242, 1524, 3781, 1534, 3583, 3634 |
| OZ10 | 1089, 1765, 1975, 161, 2036, 2056, 2494, 3433, 4048, 2938, 1621, 232, 1721, 1055, 3883, 1343, 1910, 3127, 3771, 273, 593, 2803, 2319, 2147, 1011, 3069, 3924, 281, 1186, 1967, 2700, 2247, 1982, 3134, 2485, 3141, 230, 3765, 4173, 1192, 3819, 296, 3241, 3082, 1988, 108, 1459, 1482, 1516, 1405, 674, 2225, 2756, 1349, 4174, 3414, 207, 685, 2357, 707, 3891, 343, 1026, 838, 3760, 2266, 1874, 2821, 258, 2896, 2158, 801, 4144, 2245, 989, 2901, 532, 1422, 1289, 579, 2365, 3537, 3181, 2432, 443, 4125, 1881, 3245, 14, 487, 3845, 3272, 1751, 2476, 511, 696, 3210, 3471, 3218, 2440, 1451, 3944, 2450, 2934, 482, 3000, 2275, 2919, 347, 794, 1696, 3824, 3580, 1561, 1307, 3289, 2527, 2044, 1883, 237, 4013, 2402, 1999, 2282, 18, 1691, 1686, 1053, 2720, 3975, 3531, 1698, 518, 2222, 506, 2679, 266, 1854, 1355, 2096, 34, 479, 3929, 2778, 750, 2725, 2403, 1334, 30, 3472, 3775, 1410, 2514, 700, 1195, 3540, 2666, 1250, 2456, 4107, 262, 1645, 3817, 1740, 3366, 559, 3363, 3965, 270, 339, 1631, 2459, 3485, 2767, 1403, 556, 910, 165, 1301, 3960, 2781, 3430, 1978, 962, 157, 1832, 3585, 3265, 51, 1888, 2338, 3428, 2918, 3088, 2363, 3280, 505, 4025, 1025, 2124, 1709, 2252, 1754, 3352, 3847, 3413, 2, 1471, 2415, 27, 2976, 1353, 2500, 695, 1627, 2968, 993, 1903, 1148, 1648, 3608, 3261, 1679, 809, 1047, 2175, 531, 1673, 3281, 2694, 3434, 2654, 1815, 2417, 3843, 4159, 775, 1129, 1677, 3635, 399, 2052, 1081, 3448, 3969, 2722, 4123, 3251, 4069, 1858, 1690, 185, 2142, 907, 1724, 3998 |
| OZ11 | 201, 4136, 1400, 1862, 2836, 1669, 517, 2770, 4043, 3291, 3225, 3703, 2418, 2508, 2663, 2378, 2023, 3782, 3627, 1221, 1002, 2741, 3424, 3544, 1072, 4109, 570, 1060, 1430, 2638, 3881, 1587, 3226, 2332, 954, 1269, 1575, 1640, 3521, 1035, 2524, 2967, 1067, 2515, 3892, 530, 772, 3060, 864, 3612, 3882, 1662, 3488, 3543, 3405, 137, 1664, 1276, 2071, 669, 3256, 824, 3223, 3048, 951, 2748, 2656, 632, 1132, 3825, 2000, 3031, 62, 1441, 3118, 2020, 3057, 312, 3811, 3110, 651, 1370, 316, 3939, 193, 3401, 455, 3036, 2265, 145, 1188, 3358, 2465, 2263, 1526, 1723, 1757, 105, 3440, 1665, 4135, 3351, 3300, 3016, 1980, 2621, 3394, 843, 1040, 2541, 2379, 1912, 49, 38, 2869, 3490, 2389, 221, 2067, 1486, 923, 3376, 2752, 3346, 777, 2815, 717, 118, 1827, 1555, 1175, 3115, 815, 3197, 12, 675, 1781, 2698, 1732, 1082, 4113, 1294, 1200, 3753, 3027, 1760, 2013, 3927, 1602, 1983, 1449, 241, 1748, 1316, 874, 521, 1265, 1794, 609, 3897, 1421, 2672, 3940, 2447, 45, 3630, 3636, 2393, 3410, 1844, 3131, 2827, 3325, 1409, 3382, 3650, 2853, 388, 3736, 1112, 3149, 1162, 1863, 2930, 2703, 1538, 1171, 3295, 817, 1871, 898, 3722, 2495, |

TABLE 2-continued

Mixing Pool and Corresponding Clone Numbers contained therein

|     |     |
| --- | --- |
|     | 4141, 2131, 1572, 2333, 3442, 2229, 2423, 1582, 1513, 2010, 1463, 4114, 3698, 1994, 3682, 2042, 3907, 1268, 1661, 4169, 3436, 2825, 2660, 1784, 1170, 2045, 1465, 2008, 1558, 1411, 242, 852, 2118, 2879, 1545, 2501, 1121, 2123, 288, 3773, 683, 1420, 2470, 2208, 3797, 770, 3364, 1554, 2468, 3367, 3160, 3482, 2381, 4078, 1992, 2591, 1015, 2041, 2187, 3542, 1149, 2478, 3646 |
| OZ12 | 3130, 1520, 1853, 2148, 3513, 3853, 381, 1331, 4039, 3699, 602, 1234, 709, 3092, 636, 933, 529, 587, 4044, 1527, 1504, 2464, 3978, 3673, 456, 571, 1141, 2436, 1553, 3805, 2087, 2230, 3104, 819, 426, 3157, 3046, 419, 684, 2759, 1263, 3878, 991, 2813, 3481, 2001, 76, 2829, 3035, 1923, 691, 4106, 1273, 2811, 1949, 1702, 1386, 534, 3995, 431, 4134, 1641, 3748, 2337, 1472, 3307, 3708, 4083, 1865, 3404, 1073, 658, 2936, 2491, 3858, 3051, 3747, 3021, 3755, 2850, 226, 968, 2437, 1314, 90, 1734, 595, 1176, 3050, 1948, 2609, 789, 3012, 2190, 2149, 3503, 1443, 77, 2474, 3250, 1240, 1328, 175, 3637, 2121, 2926, 1736, 2974, 1695, 2120, 2880, 2894, 3578, 2183, 785, 759, 2130, 1438, 897, 1539, 1989, 308, 987, 2816, 1169, 2153, 2400, 71, 1777, 1917, 4084, 2228, 1518, 3201, 718, 3125, 410, 1389, 3449, 647, 2956, 714, 1833, 2557, 984, 89, 2702, 1819, 3757, 3369, 2454, 1902, 75, 2877, 2800, 557, 1327, 3463, 1966, 1163, 438, 2924, 197, 363, 3216, 1905, 195, 3820, 2761, 3912, 63, 1445, 47, 3276, 3318, 1578, 612, 1253, 2985, 3014, 1617, 2958, 67, 1681, 1435, 3502, 1324, 2340, 1523, 2994, 2310, 1693, 3594, 1022, 496, 1252, 2141, 3567, 1086, 3010, 2348, 2254, 1940, 3277, 357, 323, 4, 2399, 1728, 1512, 454, 2386, 2294, 4037, 1368, 623, 2549, 206, 548, 762, 1364, 2241, 328, 1404, 1488, 3183, 3526, 1118, 0, 2615, 3478, 1644, 2532, 1041, 721, 422, 807, 2089, 1367, 2953, 3640, 3517, 4045, 1964, 1159, 2837, 78, 1613, 1123, 1218, 3491, 163, 272, 2885, 1156, 2750 |
| OZ13 | 1059, 1382, 2471, 3809, 2221, 3921, 348, 2182, 3484, 928, 2605, 844, 3623, 3899, 889, 3368, 1128, 2774, 1741, 2662, 563, 46, 812, 3388, 3533, 3675, 1914, 3417, 3515, 1198, 1429, 2093, 617, 452, 3163, 4017, 2115, 2753, 3073, 1481, 516, 3916, 2556, 1051, 4130, 3465, 2947, 3349, 3904, 3816, 2738, 3678, 3188, 568, 4062, 2851, 4127, 3209, 3267, 1264, 513, 358, 1321, 450, 2699, 2270, 1101, 4117, 4172, 1597, 3862, 1063, 2573, 377, 1329, 4129, 199, 1434, 3302, 3242, 2567, 884, 3915, 96, 116, 3728, 3598, 1454, 2531, 604, 389, 3879, 331, 1414, 3609, 1088, 578, 2739, 1570, 3842, 1612, 219, 3552, 4029, 1247, 937, 881, 124, 1697, 4066, 1946, 3774, 1283, 3649, 1637, 330, 4003, 628, 1805, 2277, 2049, 2612, 3743, 1071, 1251, 755, 1045, 1860, 4040, 741, 2244, 1106, 523, 1151, 3337, 464, 1735, 384, 471, 1758, 2235, 3737, 408, 2838, 1113, 2328, 1855, 2029, 2929, 319, 1290, 1210, 2613, 3025, 1867, 2137, 507, 1105, 1144, 2875, 103, 3951, 1084, 91, 1573, 1347, 162, 1061, 3857, 2335, 3204, 2455, 448, 3913, 132, 115, 2132, 4165, 60, 2874, 1588, 1302, 1448, 1544, 725, 3086, 3764, 4028, 3962, 3818, 1900, 2489, 2749, 1810, 2164, 975, 3054, 3359, 4035, 435, 2046, 2344, 3672, 4101, 3658, 370, 4053, 2940, 1001, 40, 3525, 1431, 3412, 2796, 3768, 3170, 1102, 337, 1615, 3633, 699, 2220, 376, 2805, 351, 3993, 3745, 2966, 1023, 2368, 3439, 1224, 3852, 3889, 3511, 2857, 988, 3758, 3375, 3249, 2217, 2452, 3689, 2490, 2543, 2370, 497, 2309, 2866, 1551, 586, 1762, 1742, 26, 360, 541 |
| OZ14 | 2155, 1442, 302, 3079, 1750, 3207, 1354, 2604, 3274, 540, 437, 1037, 3452, 1878, 1308, 184, 3400, 3389, 2481, 2848, 1049, 4137, 42, 424, 733, 186, 3076, 2480, 3776, 575, 2986, 2685, 509, 3239, 2104, 3679, 2435, 1768, 1995, 3153, 823, 3418, 2364, 1687, 1335, 3837, 1229, 2819, 2895, 965, 1282, 3159, 572, 1599, 3097, 134, 2766, 850, 2136, 4057, 3999, 2098, 2784, 4041, 317, 395, 259, 4139, 1961, 1419, 3074, 3479, 3290, 3812, 4092, 2590, 3677, 732, 677, 133, 2185, 2665, 1931, 1714, 781, 152, 449, 2568, 1540, 2705, 580, 3535, 3071, 3231, 782, 2376, 663, 2977, 3113, 1130, 3464, 2199, 3080, 2889, 247, 3186, 1787, 1255, 439, 3615, 4051, 2708, 2129, 831, 1402, 841, 350, 3687, 3644, 2186, 2648, 730, 2232, 592, 2626, 2016, 1299, 3124, 526, 2521, 3146, 645, 959, 1267, 1711, 3972, 93, 2196, 793, 3550, 1147, 100, 2822, 1818, 1385, 1684, 364, 2392, 918, 2169, 613, 1254, 387, 2088, 2018, 3981, 1388, 4104, 3695, 566, 1446, 2979, 2779, 1680, 336, 3477, 1066, 4056, 3001, 1332, 1746, 3575, 656, 3176, 3008, 2203, 565, 1956, 3607, 1618, 285, 3690, 231, 4065, 2823, 978, 1499, 4081, 1109, 1592, 3, 1205, 1843, 1658, 304, 3864, 2554, 2536, 2534, 1984, 3604, 434, 3165, 788, 3849, 1965, 1000, 2026, 2231, 172, 2858, 3701, 757, 1111, 3877, 1601, 3498, 380, 3166, 2881, 3826, 2429, 153, 2227, 3343, 251, 1812, 3117, 3606, 2256, 1031, 4156, 3311, 972, 909, 1297, 1312, 3396, 2959, 942, 2757, 3042, 2178, 2162, 466, 1140, 138, 3861, 2688, 3711, 4005, 2467, 3579, 3936, 1117, 436 |
| OZ15 | 1577, 514, 2659, 1310, 2576, 549, 3275, 1311, 3884, 3143, 1348, 2510, 2675, 1158, 1233, 3489, 68, 3616, 217, 3438, 3876, 1889, 837, 3778, 1763, 583, 414, 2281, 1203, 2730, 2339, 3238, 3656, 95, 2353, 2239, 2102, 1044, 2063, 3792, 2579, 585, 2676, 361, 2634, 2871, 2921, 313, 159, 2526, 1358, 3911, 1131, 2961, 3710, 3720, 2914, 391, 1688, 3707, 3191, 4126, 484, 1322, 3676, 1619, 2820, 2283, 3335, 2696, 3920, 3314, 802, 938, 4111, 1530, 4152, 1676, 493, 3840, 3941, 1685, 2920, 2031, 4158, 4098, 2724, 3158, 1959, 3589, 3950, 1080, 2143, 292, 3739, 155, 3244, 1497, 366, 1894, 4170, 3546, 920, 2734, 3260, 4089, 3003, 1935, 3162, 719, 1976, 374, 2841, 1772, 826, 722, 2205, 4090, 1675, 3102, 1563, 150, 158, 2902, 3059, 2413, 3357, 1792, 1461, 2670, 179, 160, 1204, 3505, 1052, 3680, 2504, 1517, 1135, 33, 1489, 368, 3212, 2257, 758, 796, 2552, 2574, 3407, 4033, 265, 3838, 1738, 746, 3019, 2523, 2271, 2795, 970, 1972, 2683, 1046, 773, 3423, 1320, 2391, 180, 2599, 457, 2640, 1207, 310, 900, 2113, 963, 2090, 906, 3024, 2849, 615, 2681, 72, 3655, 4085, 3855, 1816, 1143, 2888, 3271, 1030, 3605, 3553, 3200, 254, 2528, 1847, 2170, 622, 4022, 2562, 2412, 1947, 2641, 2546, 1771, 795, 692, 3061, 2172, 1879, 2347, 626, 791, 3851, 1895, 3177, 1479, 1286, 1013, 960, 4147, 3740, 1712, 1598, |

TABLE 2-continued

Mixing Pool and Corresponding Clone Numbers contained therein 3756, 1483, 1357, 2622, 940, 204, 3221, 3132, 2692, 3865, 373, 256, 1182, 1393, 485, 603, 2847, 3903, 1206, 1214, 2840, 2780, 1155, 3741, 3213, 88, 760, 2043, 797, 2201, 2832, 3329

Figure 4:
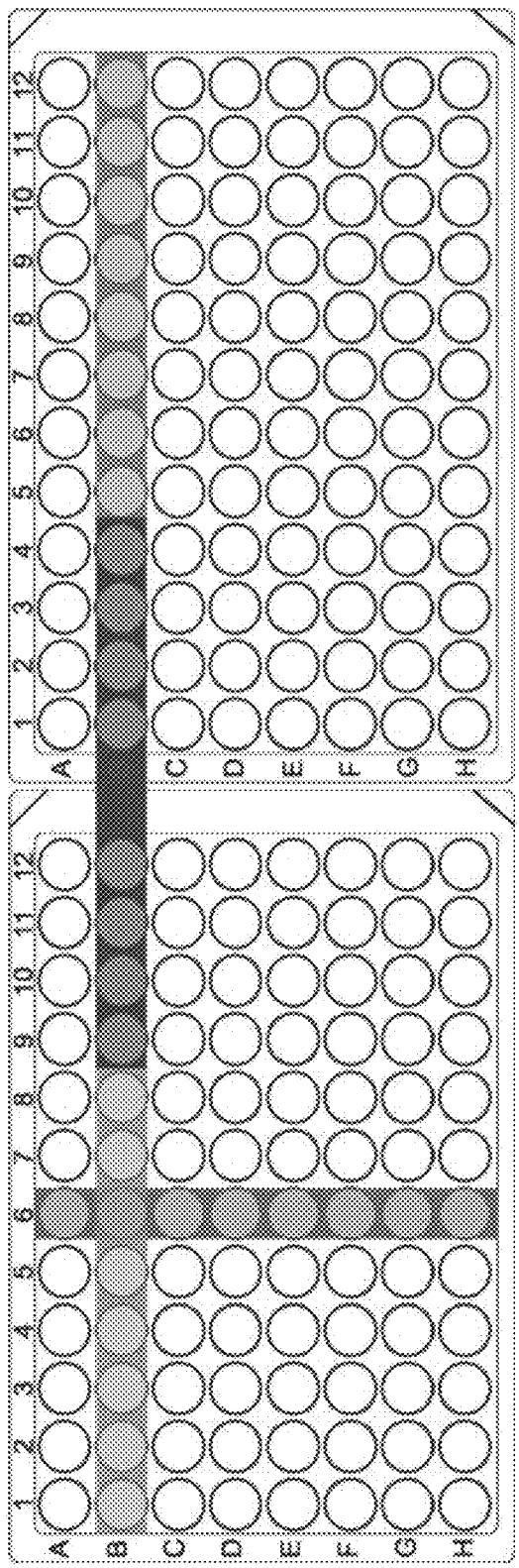
FIG. 4 is a construction diagram of foundation mixing pool; the consecutive 8 clones in the same row or column are in the same foundation mixing pool.

Extraction of DNA of Mixing Pool 4096 clones selected from the library are inoculated into 96-hole culture plates, each culture hole containing 1 ml of freezing substrate (formula for 1 L of the freezing substrate is as follows: 10 g of peptone, 5 g of yeast extract, 10 g of NaCl, 8.215 g of $K_2HPO_4.3H_2O$, 1.795 g of $KH_2PO_4$, 0.5 g of citric acid sodium, 0.848 g of $(NH_4)_2SO_4$, 44 mL of glycerol. 0.4 mL of 1 M/L $MgSO_4$ is added to the formula before usage), cultured for 18 hours at 37° C. preserved at 80° C. Mix consecutive 8 clones of each row and each column of every 96-hole culture plate to form base pools. If the number of consecutive clones in the same row is less than 8, then put the clones of the same row of the next plate into the base pool to get a total of 1024 base pools (FIG. 4). Suck 150 μL of bacteria from each culture hole, then each base pool contains 1.2 mL of bacteria. Then according to the construction strategy of sequencing pool, put 4096 clones to a 16×16×16 cube to construct the 6D pool, each of which contains 16×16=256 clones. Compare the clones of each mixing pool to the base pool, 32 base pools can be once again combined into a sequencing pool with 256 clones. Replicate the base pools into the new 96-hole culture plate, 100 μL of bacteria and 1.1 ml of 2×YT culture substrate are absorbed into each hole. The base pools belonging to the same sequencing pool are adjacent to each other in 96-hole culture plate, among which column 1 to column 4, a total of 32 base pools can be combined into a sequencing pool, column 9 to column 12 can be combined into another sequencing pool, four columns in the middle are vacated to prevent cross contamination. Then newly replicated 96-hole culture plate is cultured for 18 hours at 37° C. Finally replicate 15 copies of the consecutive base pools belonging to the same sequencing pool on the newly replicated 96-hole culture plate into five new culture plates, each new hole containing 40 μL of bacteria and 1 ml of 2×YT substrate, being cultured at 37° C. for 18 hours. Mix the clones in each newly cultured sequencing pool, use Large-Construct Kit of QIAGEN company to extract plasmid DNA. The concentration of plasmid DNA is required to be ≥150 ng/μL, the total amount is required to be ≥30 ug. This process can also first extract the DNA of all clones respectively, then mix.

Sequence DNA of Mixing Pool

Use HiSeq 2000 high throughput sequencing instrument of Illumina company to carry out the double terminal sequencing for plasmid DNA of 96 mixing pools. When the DNA of PX, PY, PZ mixing pool constructs sequencing library, the fragment length is 500 bp; when the DNA of OX mixing pool constructs sequencing library, the fragment length is 800 bp; when the DNA of OY mixing pool constructs sequencing library, the fragment length is 1200 bp; when the DNA of OZ mixing pool constructs sequencing library, the fragment length is 1800 bp. The sequence read length of both ends is 100 bp; each pool can get the total sequence length of about 710 Mb, about 20 times of coverage. The average error rate of the sequence is less than 3%. The average error rate through the calculation of sequencing quality values is 2.64%.

Scan Sequencing Results and Obtain the Feature Sequence Set of the Mixing Pool

Figure 5:
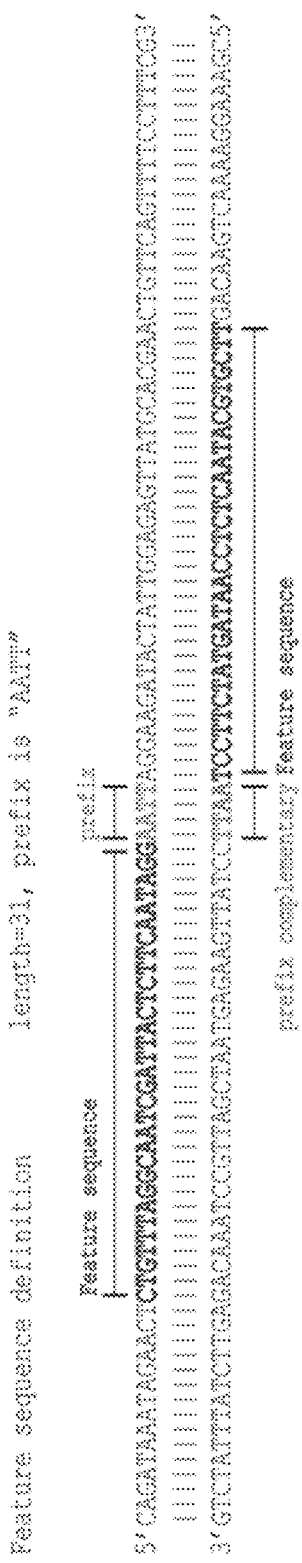
FIG. 5 is a definition diagram of feature sequence; for a sequence of DNA, when it is required to assign and mark the prefix sequence (such as "AATT") and feature sequence length (such as 31), the base with a certain length in the upstream of prefix sequence and the base with the same length in the upstream of the complementary sequence of the prefix sequence are a strip (pair) of feature sequence of this DNA sequence; the prefix sequence can be specified for more, the length of feature sequence can also be specified according to the requirements.

Feature sequences are used for the assembly of the physical map, as a feature of the DNA segment of the clone. It is equivalent to the band length in the traditional use of fingerprints to build the physical map. As shown in FIG. 5, for a strip of DNA sequence, when the specified mark prefix sequence is "AATT" and the length of the feature sequence is 31, 31 bases in the prefix sequence upstream and 31 bases in the prefix sequence reverse complementary sequence upstream are the feature sequences of the DNA sequence. Several prefix sequences can be specified, and the length of the feature sequence can also be specified according to the requirement.

In the specific embodiment, select the prefix sequence with two restriction enzyme sites BamHI(G|GATCC) and EcoRI(G|AATTC), the feature sequence length is 31 bp. Scan all the sequences in each mixing pool one by one, and combine all the feature sequences into one set, which is called the feature sequence set of the mixing pool, not containing duplicate elements. When scan the feature sequences of mixing pools, record the number of times of each feature sequence appears. 96 mixing pools can get 96 feature sequence sets, the feature sequence set of each mixing pool contains about 98000 feature sequences.

Analyze the Clone Feature Sequence Set

For the feature sequence set obtained from each mixing pool, delete the feature sequences which only appear for once, number the feature sequence sets of mixing pools after processing. The number is corresponding to the pool number:

$PX0, PX1, PX2 \ldots PX15;$ $PY0, PY1, PY2 \ldots PY15;$ $PZ0, PZ1, PZ2 \ldots PZ15;$ $OX0, OX1, OX2 \ldots OX15;$ $OY0, OY1, OY2 \ldots OY15;$ $OY0, OY1, OY2 \ldots OY15;$ respectively represent the feature sequence sets of 16 mixing pools in PX, PY, PZ, OX, OY and OZ mixing pool strategies.

According to the following steps, analyze the clone feature sequence sets:

1) Compute the intersection set of the feature sequence sets of the mixing pool where the clones locate. Such as number 1225 clone in six mixing pools as PX0, PY15, PZ0, OX0, OY15 and OZ0, compute the intersection set of the feature sequence set of the six mixing pools PX0∩PY15∩PZ0∩OX0∩OY15∩OZ0 (the operator "∩" represents the intersection set of two sets), to get the initial intersection set $I_{1225}$ of clone 1225 feature sequence. Similar to other clones, obtain the initial intersection of the feature sequences of all clones, expressed as $I_t$ (where the subscript i indicates the clone number), such as $I_{1191}$ indicates the initial intersection of the feature sequence of number 1191 clone.

2) Compute the excluded union set of the mixing pools where the clone s locate. The excluded union set of all the mixing pools of clone is expresses as $U_{i(p)}$, among which i is clone number, p is the pool number of the clone. Taking clone 1225 as an example, the excluded union set of its mixing pool PX0 is the union set of the initial intersection of all the other clones (in addition to clone 1225), the excluded union set of clone 1225 in the mixing pool PX0 $U_{1225(PX0)}=I_{68} \cup I_{509} \cup I_{3904} \cup \ldots \cup I_{3761} \cup I_{3663} \cup I_{3091}$; (the operator "U" represents the union set of two sets; the order of the initial union set is consistent with the order of clone number in the PX0 of Table 1, but not include clone 1225).

Similarly, the excluded union sets of clone 1225 in the mixing pool PY15, PZ0, OX0, OY15 and OZ0 respectively are as follows:

$$U_{1225(PY15)}=I_{1191} \cup I_{3294} \cup I_{2073} \cup \ldots \cup I_{3403} \cup I_{3253} \cup I_{1085};$$

$$U_{1225(PZ0)}=I_{2151} \cup I_{44} \cup I_{3661} \cup \ldots \cup I_{436} \cup I_{3329} \cup I_{1981};$$

$$U_{1225(OX0)}=I_{68} \cup I_{509} \cup I_{3904} \cup \ldots \cup I_{82} \cup I_{3487} \cup I_{1428};$$

$$U_{1225(OX0)}=I_{68} \cup I_{509} \cup I_{3904} \cup \ldots \cup I_{1547} \cup I_{1791} \cup I_{973};$$

$$U_{1225(OZ0)}=I_{1191} \cup I_{3294} \cup I_{2073} \cup \ldots \cup I_{3923} \cup I_{3803} \cup I_{1981}$$

3) The final feature sequence set of the clone. Use the symbol Fi to express, where the subscript i is the clone number. For each clone, use its initial feature sequence intersection to minus the intersection of its excluded union set in the mixing pool to get its final feature sequence set. Such as clone 1225, the final feature sequence set is $$F_{1225}=I_{1225}-(U_{1225(PX0)} \cap U_{1225(PY15)} \cap U_{1225(PZ0)} \cap U_{1225(OX0)} \cap U_{1225(OY15)} \cap U_{1225(OZ0)})$$

Among which the operator "−" represents the calculation of difference set of two sets.

The more detailed algorithm for the analysis of the clone feature sequence set refers to the analysis algorithm of the clone feature sequence set and k-mer set.

Construct the Clone Contigs

Compute the union set of feature sequences of all the clones, construct index table for the feature sequences in the union set, each feature sequence corresponding to an index value which starts from 1. Replace the feature sequences in the final feature sequence set of each clone with the corresponding index values, then sort the index value from small to large, export the index values after sorting to ".size" file compatible with the clone assembly software FingerPrinted Contig (FPC V9.4). The index values exported to ".size" file are equivalent to the band length in the fingerprint construction physical map method. The contents of ".size" files of the index values of the final feature sequences of all clones are as follows:

| | |
|---|---|
| 3280 | 133 Gel |
| 1 | |
| 2 | |
| 3 | |
| 4 | |
| 5 | |
| 6 | |
| ... | |
| 127 | |
| 128 | |
| 129 | |
| 130 | |
| 131 | |
| 132 | |
| 133 | |
| −1 | |
| ... | |
| 1225 | 117 Gel |
| 759 | |
| 761 | |
| 1839 | |
| 1841 | |
| 1857 | |
| ... | |
| 21287 | |
| 38090 | |
| 38092 | |
| 89023 | |
| 93016 | |
| −1 | |
| ... | |
| 1022 | 80 Gel |
| 273 | |
| 281 | |
| 301 | |
| 343 | |
| 17787 | |
| 17788 | |
| 17789 | |
| 17790 | |
| 17791 | |
| ... | |
| 53407 | |
| 53417 | |
| 53426 | |
| 66412 | |
| 66414 | |
| 97491 | |
| 97492 | |
| −1 | |

The ".size" file contents of each clone include three parts, that is, the first part includes clone name (number), the number of index values (band number) and "Gel", the second part includes each index value, the third part is the end tag "−1". For instance, clone 1225 finally gets 117 feature sequences, corresponding to 117 index values.

Figure 6:
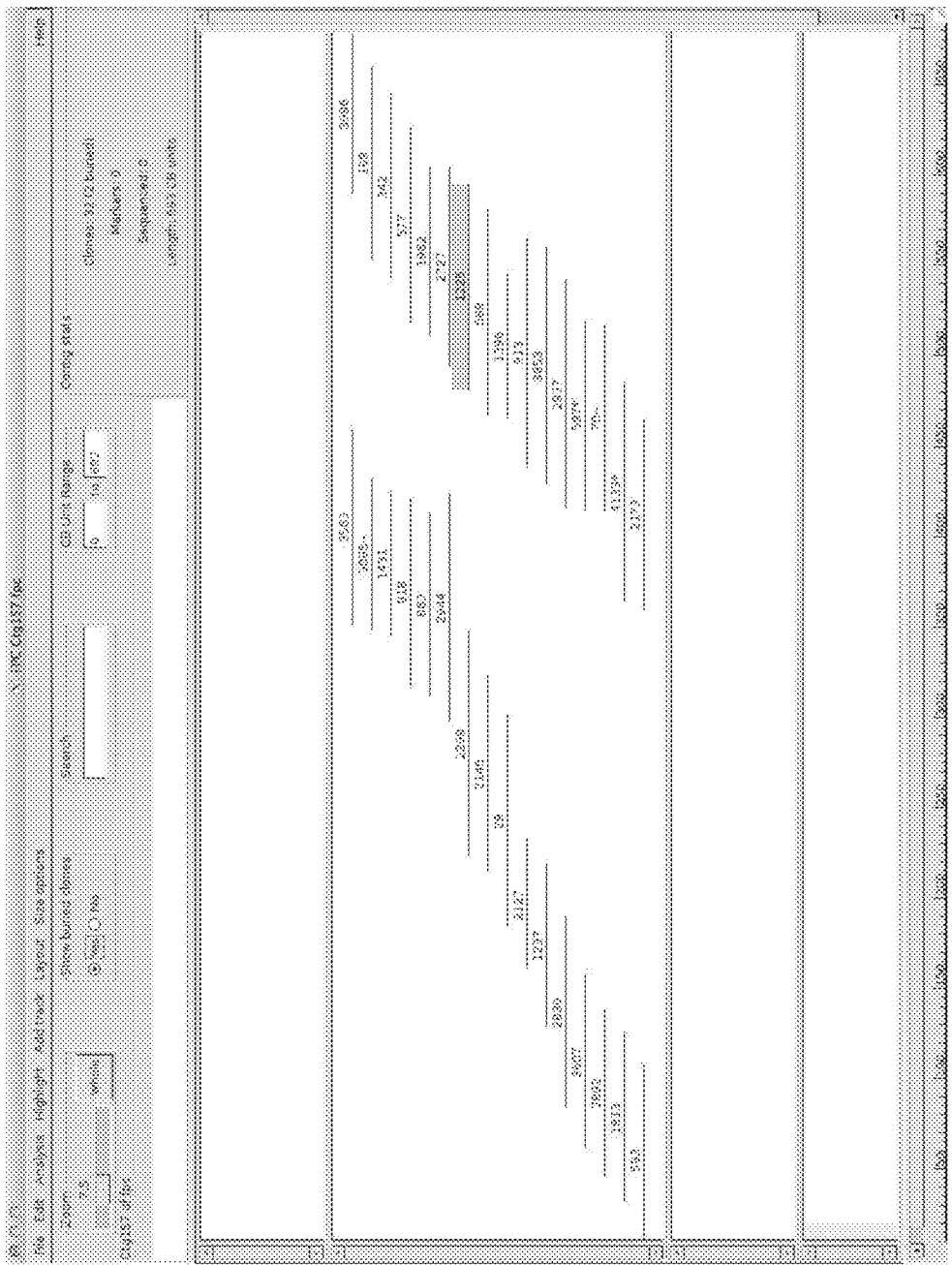
FIG. 6 is the contig 157; the clone contig has a total of 32 clones, the prominently displayed clone in the figure is in clone 1225.
Figure 7:
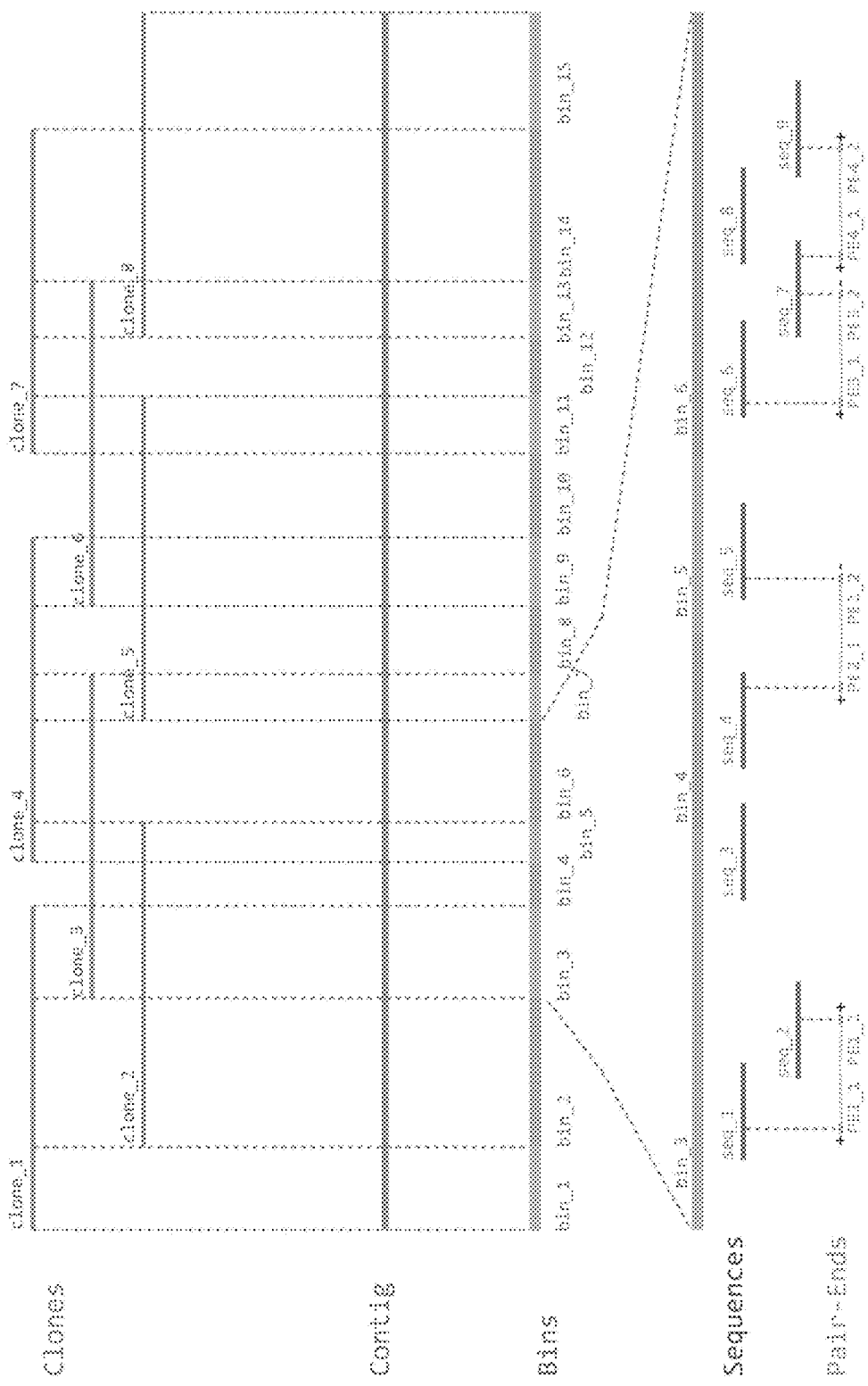
FIG. 7 is a schematic diagram of segmenting the clone contig into a number of small blocks; each bin contains the corresponding k-mer set; bin means the small block after segmenting the clone contig, a total of 15. Seq means the sequence positioned to the bin, a total of 9. PE means the double end of NGS, a total of 4, PE1_1 means one end of PE1, PE1_2 means the other end of PE1; the symbols of the ends of each PE "+" or "−" mean the alignment direction of corresponding end sequence and position sequence; if the symbol of the two ends are the same, when connect the two sequences, carry out reverse complementary to one of the sequences.
Figure 8:
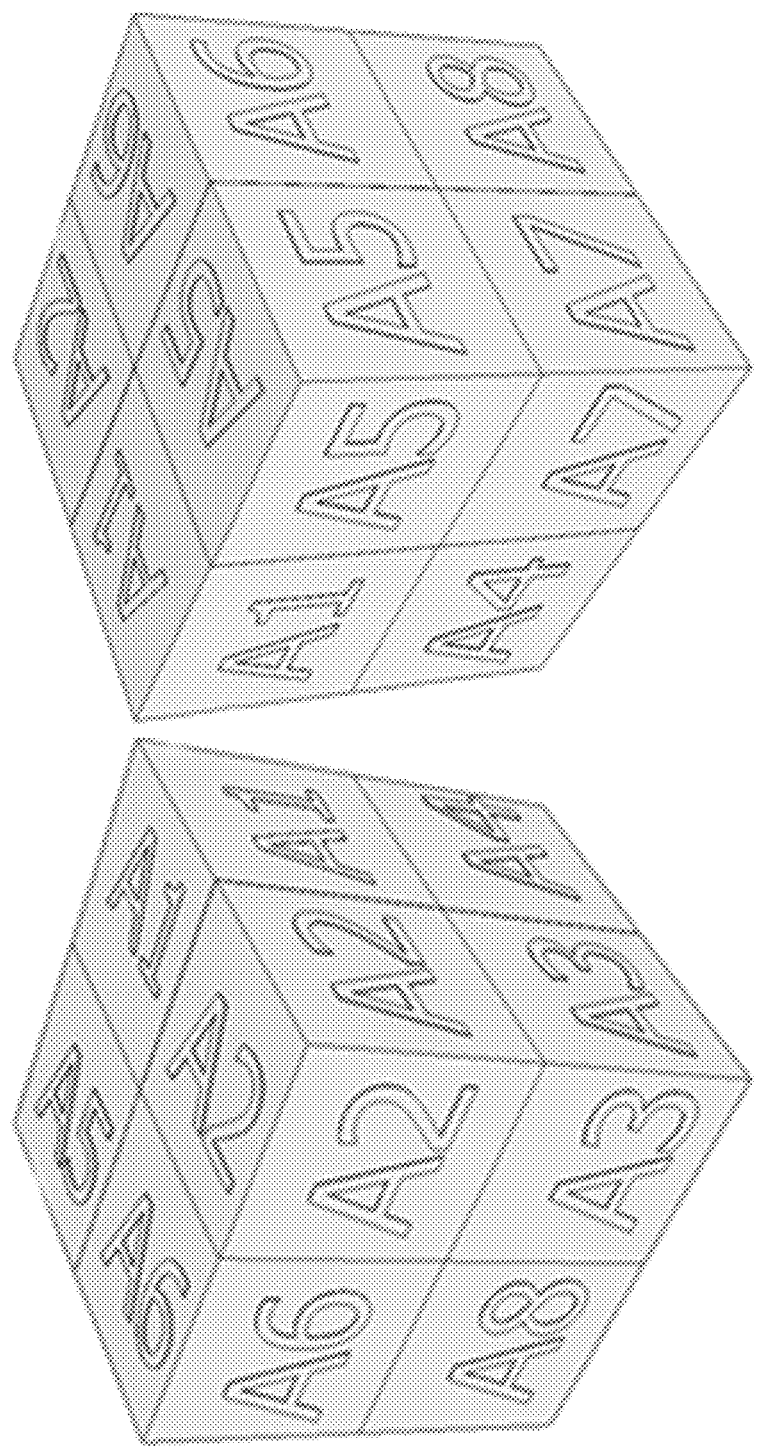
FIG. 8 is an arrangement diagram of 8 clones in the same cube.
Figure 9:
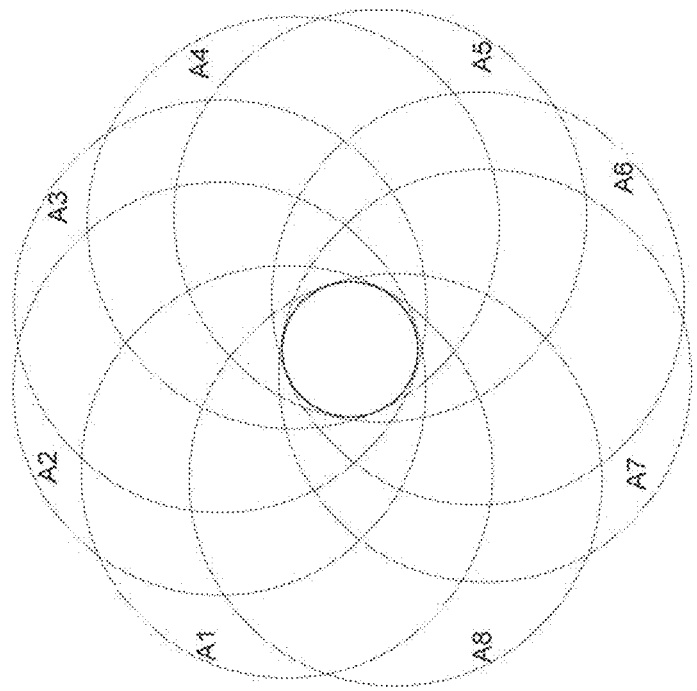
FIG. 9 is a clonal overlapping relation diagram; the area of each circle means the number of k-mer of corresponding clones; the area of the overlapping part of each circle reflects the number of common k-mer, among which the central circle part means that all the clones have k-mer; the area reflects the number of k-mer of the vector sequences when construct BAC library; other part inside the circle besides the central circle means the common k-mer of all the clones which may come from the repetitive sequences.
Figure 9:
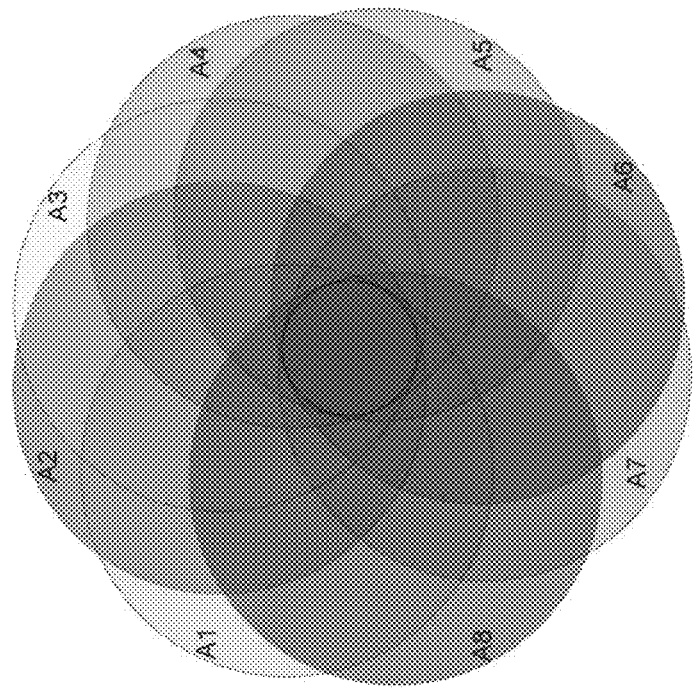
Figure 10:
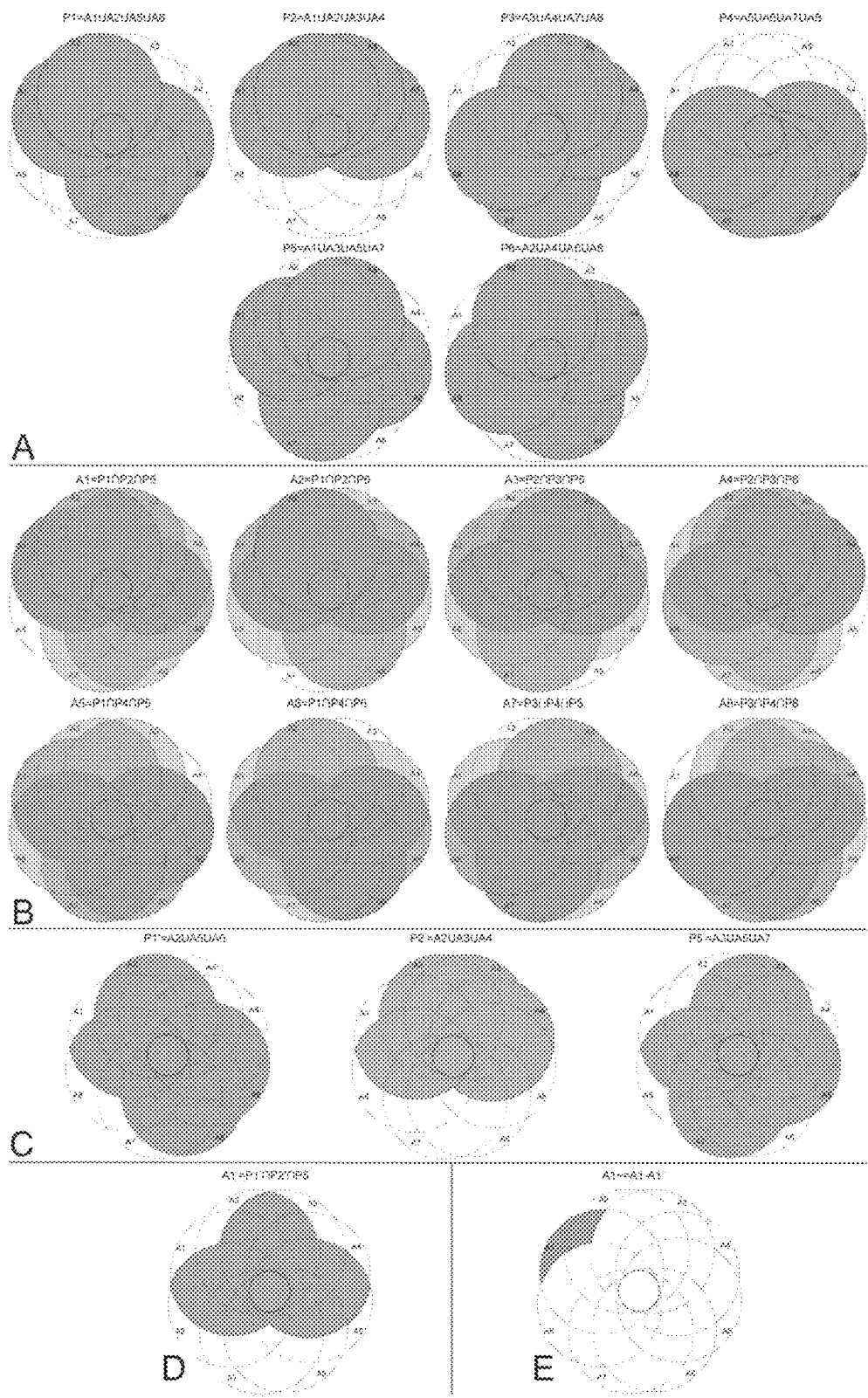
FIG. 10 illustrates a figure calculation process, a part with the darkest color in B is calculation results.

Input the exported ".size" file into the assembly software FPC to assemble. Set Tolerance to 0 (this value must be set to 0), set Cutoff to 1e-12, other values are default. Carry out the initial assembly to produce clone contig. Then, set if >=5 Qs, Step is 5, carry out DQer. Finally obtain 220 clone contig. All the contig contain a total of 4021 clones for the first time assembled to produce clones overlap. Then, set the >=5 Qs if, Step 5, DQer. Finally, 220 clones were obtained, and all the contig contained 4021 clones, and 75 clones were not in any one contig. As shown in FIG. 6 it is the arrangement of the clones in the contig 157 (ctg157).

Scan the Sequencing Results and Get K-Mer Set of the Mixing Pool

The definition of k-mer is the same as the k-mer definition in the short sequence assembly method based on Bruijn graph. For a certain DNA sequence, take the window of a certain length, slide from 5' to 3' one base by one base. For each slide, the subsequence in the window is one k-mer of the DNA sequence. When the window length of a sequence is 13, there are a total of 34 k-mers. Therefore, for a sequence of length L, when the window length (or k-mer length) is k, the maximum number of k-mer generated is L−k+1.

```
5' ATCGTTGCTTAATGACGTCAGTCGAATGCCATGACGTGACTGACTG 3'
   ATCGTTGCTTAAT
    TCGTTGCTTAATG
     CGTTGCTTAATGA
      GTTGCTTAATGAC
..............................................
                               TGACGTGACTGAC
                                GACGTGACTGACT
                                 ACGTGACTGACTG
```

In the embodiment, the length of k-mer is 31 bp. Scan all the sequences of each mixing pool and combine all the k-mers into one set which is called the k-mer set of this mixing pool where repetitive elements are not contained. When scan the k-mers of mixing pool, it will also record the number of times each k-mer appears. 96 mixing pools can get 96 k-mer sets, the k-mer set of each pool contains about 95000000 feature sequences.

Analyze the K-Mer Set of the Clone

Due to the same nature of feature sequence and k-mer, the algorithm of analyzing the clone feature sequence is also applicable to the analysis of the k-mer set of the clone. In the process of concrete calculation, only replace the feature sequence set with k-mer set, and the other process is completely consistent.

Segment the Contigs

The algorithm for the segmentation of clone contigs is detailed in the above mentioned above "on the integration of sequence positioning and physical map".

In the embodiment, if the contig 49 (ctg49) is segmented into 27 blocks, a total of 635264 k-mer. From one end to the other end, the number of k-mers in each block is respectively 85353, 24951, 3044, 3992, 1284, 1175, 172, 125881, 12172, 8580, 4305, 16549, 1959, 26952, 12668, 6886, 6195, 6364, 20721, 6553, 4309, 4893, 26776, 18726, 12071, 83478, 1680 and 107575. Similarly other contigs are segmented into small blocks.

Sequence Assembly and Integration into the Physical Map

Assemble the NGS sequence of each mixing pool by the short sequence assembly software velvet respectively, to get the sequence contig of each mixing pool. When assembling, the parameter value of Hash length is 31, the other parameters are default, so as to obtain the initial assembly sequence of the 96 mixing pools which is about 3.4 Gb, the smallest sequence length is 62 bp. Then, filter the sequences after the initial assembly, remove the sequences less than 100 bp, combine the rest of the sequences together, so as to get a total of 1.59 Gb "fasta" format sequence, and compressed into a "gzip" format. According to the combined sequence, result in the corresponding "fasta" format quality file. All the base quality values are taken 20, and then compress the quality file generated into "gzip" format.

Reassemble the sequences after combination by the use of long sequence assembly software PCAP. The assembly parameters are all default parameters, to obtain about 270 Mb sequences after assembly.

Decompose each sequence after PCAP assembly to k-mer sets, then compute intersection sets with the k-mer sets of blocks after the clonal sequence contig segmentation, to find the one with the most intersection elements, then position the sequence to the location of this block. Through the analysis of the sequence positioned to the same clonal sequence contig, it is easy to find out which contains more overlapping sequences, so it is necessary to reassemble and combine the sequences and position it again. Reassemble the sequences positioned to the same clone contig with the sequence assembly software Phrap, and the parameter is the default parameter. Then decompose the sequences after assembly into k-mer sets, and position the sequences to the blocks of contig. After this step, there are a total of 103.1 Mb positioned sequences.

Use the double end comparison software Bowtie2 to carry out double end comparison for the NGS sequences of all the mixing pools and the positioned sequences. If two sequences are highly matching to the double end of one sequence (examples selected identity value≥97%), and the two sequences are positioned in the same clone contig, where the contig block is in a certain range, it is considered the two sequences can be connected together. According to the sequencing library fragment length and double end comparison results, calculate the length of the gap between them and fill the gap with "N". At the same time, according to the relative position of the blocks where the two sequences are located, determine the direction of the sequence. If a sequence has no double end sequence connection with other sequences, then compare its decomposed k-mer set and the k-mer sets of the adjacent blocks. If it has intersection with the k-mer sets of the adjacent blocks, then it can position the junction of the two blocks and determine its direction. For the sequences positioned in the block but not able to determine the direction, randomly select its direction. Finally according to the relative position of the blocks where these sequences are located, connect all the positioned sequences through double end connection into the sequences of all the clone contig. If several sequences after double end connection are positioned in the same block, then their relative position and direction can be randomly selected.

For the NGS sequence of mixing pools of 500 bp long sequencing library fragments, when carry out double end comparison to the positioned sequences, the identity is required to be ≥97%, and the relative position of two sequences in the contig blocks is in the range of 10 (the relative position range is called block range. If start from the left end of the contig, the relative position of the first block at the left end is 1, the second is 2, followed by analogy). If not the same, just according to the matching position of the two sequence and the double end, as well as the default length of 500, calculate the length of the gap between them. If the length of the gap between them is less than 100 bp (the length is referred to as the minimum gap length), and then compare 13 bases at the adjacent ends of two sequences. If the 13 bases are the same, directly connect the two sequences into one sequence, otherwise fill the gap with the corresponding number of "N". The NGS sequences of other sequencing libraries are similar to that, but the block range (500 bp sequencing library is 10) and the minimum gap length are not the same. The block range of 800 bp, 1200 bp and 1800 bp sequencing library are respectively 17, 22, 31, and the minimum gap length is 120 bp, 150 bp, 180 bp, respectively. Through the connection of the sequence double end and filling the gap between sequences, obtain 220 contig sequence, a total of 109.9 Mb.

The Contig is Positioned and Connected to the Chromosome

If there are molecular markers, decompose the sequence of each marker into k-mer set, and compute the intersection of the k-mer set of each mixing pool (delete the k-mer sets which only appear once). If the k-mer set of the mixing pool contains the k-mer set of the marker sequence, assign the sequence to the mixing pool, so as to get the marker sequence of the mixing pool. Use the algorithm for analyzing the clone feature sequence set to analyze the market set of the clone. If by Southern blot hybridization or PCR, it can directly determine the marker of the clone in the BAC library. In this way, the chromosomes and the relative positions of the clones containing the markers can be determined. According to all the clone contig and the chromosomes of the clone containing the mark, assign the clone contig to the chromosome. According to the relative position of the clones in the contig and the relative position of the markers on the chromosomes, determine the direction of the contig. Finally, connect the sequences of the clone contig positioned on the same chromosome to the whole chromosome.

In the embodiment, use a total of 2072 known molecular markers (from http://www.arabidopsis.org/), filter out the markers with sequence less than 100 bp, remaining 1515 markers. If the k-mer set of a mixing pool (delete the k-mer which only appears once) contains 90% of the elements of the k-mer set of one marker sequence, assign the marker into the mixing pool, then analyze the marker set of the clone, use PCR to verify if each clone contains the analyzed molecular markers, among which 2953 clones contain one or more molecular markers. Through the marker sets of the clones, position 211 clone contig on the chromosome, then connect the clone contig sequences on the same chromosome, fill up 50 kb long "N" between the adjacent contig. Finally obtain 5 chromosome sequences, a total of 118.4 Mb.

The above embodiment adopts *arabidopsis thaliana* as experimental model. In the actual process, according to the complete genome of different species, construct BAC library, establish mixing pools is not less than 3 dimensions. Through the above calculation method obtain the complete genome sequence.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A whole-genome sequencing method based on clone DNA mixing pool, the method comprising:
  1) extracting a whole-genome DNA from cells of a species, using a restriction endonuclease to digest the whole-genome DNA, constructing a bacterial artificial chromosome (BAC) library, and preserving the BAC library in a plurality of multi-well plates;
  2) constructing BAC clone mixing pools;
  3) extracting a plurality of DNA clones from the BAC clone mixing pools, inoculating and culturing the plurality of DNA clones in culture plates, mixing the plurality of DNA clones to obtain sequencing samples according to the BAC clone mixing pools of 2), and extracting plasmids from the sequencing samples;
  4) performing pair-end sequencing for the plasmids of 3) by next-generation sequencing (NGS) sequences to obtain sequences of each of the mixing pools;
  5) scanning sequences of each of the mixing pools to obtain a feature sequence set and a k-mer set of each mixing pool;
  6) inputting the feature sequence set and the k-mer set of each mixing pool of 5) into a computer to analyze a corresponding feature sequence set and a corresponding k-mer set of each clone according to the feature sequence set and the k-mer set of each mixing pool;
  7) activating the computer to construct clone contigs according to feature sequence sets of clones;
  8) activating the computer to divide the k-mer sets of the clones into small k-mer sets by the clone contigs and to position the small k-mer sets onto the clone contigs;
  9) activating the computer to assemble the NGS sequences in the mixing pool of 3) to yield sequence contigs;
  10) activating the computer to position the sequence contigs onto the clone contigs, to use sequenced paired-end information to connect the sequence contigs, and to determine directions thereof, to obtain sequences of the clone contigs; and
  11) using Southern blot hybridization or PCR to determine positions and directions of molecular markers on the plurality of DNA clones, inputting the positions and the directions of the molecular markers into the computer to determine relative positions and directions of the clone contigs and to connect the sequences of clone contigs as whole stripe of chromosome sequences to obtain whole-genome sequences; wherein
algorithms for analyzing the feature sequence sets and the k-mer sets of the clones are as follows:
  a total number of clones of the BAC library of a certain species is defined as a, and a total number of the constructed mixing pools is defined x, then:
  the k-mer set of the mixing pool at a κ-th dimension and having an index of λ is expressed as: $P_{(\kappa,\lambda)}$;
  the k-mer sets of the mixing pools comprising a given clone are expressed as: $\{P_{(\delta)}|\delta<m, P_{(\delta)}\in P\}$;
  an intersection set of k-mer sets of the mixing pools comprising the given clone, namely an initial k-mer set of the given clone, is expressed as: $C_\tau = \cap_{\delta=1}^{x} P_{(\delta)}$;
  an excluded union k-mer set (EUKS) of the given clone in the mixing pools is expressed as: $CU_{(\kappa,\tau)} = \cup_{\nu=0}^{a} C_\nu$ ($\nu \neq \tau$, $0<\nu<a$);
  an intersection set of all excluded union k-mer sets (EUKS) of the given clone is expressed as: $CI_\tau = \cap_{\kappa=0}^{x} CU_{(\kappa,\tau)}$; and
  a final k-mer set (FKS) of the given clone is: $CF = C_\tau - CI_\tau$.

2. The method of claim 1, wherein
an algorithm for division of the clone contigs is as follows: the k-mer sets of the clones are segmented into blocks according to relative positions of the clones in the clone contigs; assuming that two clones belong to a same contig and overlap with each other, set A represents the k-mer set of one clone, and set B represents the k-mer set of the other clone, then the two k-mer sets are divided into three sub sets, that is, a common k-mer set (A∩B), a specific k-mer set of A (A−B), and a specific k-mer of B (B−A); the relative position of the three k-mer sets are determined wherein the common k-mer set is located between the two specific k-mer sets; and an algorithm for positioning and integration of sequences is as follows: NGS sequences of the mixing pools are respectively assembled by a short sequence assembly software, assembly results are then merged and further assembled by a long sequence assembly software to get sequence contigs; each sequence contig is divided into k-mer sets, intersection between the k-mer sets divided from the sequence contigs and the k-mer sets of all the blocks are computed, and blocks with a maximum number of intersection elements are obtained thereby locating the sequence contigs onto the blocks of the clone overlapping area; in case the sequence located onto the same clone contig comprises multiple of overlapped regions, the overlapped sequences are required to be assembled and merged again, and a resulting sequence is then re-positioned.

\* \* \* \* \*